United States Patent
Welch et al.

(10) Patent No.: US 6,541,195 B2
(45) Date of Patent: *Apr. 1, 2003

(54) CORRECTION OF GENETIC DEFECTS USING CHEMICAL CHAPERONES

(75) Inventors: William J. Welch, San Francisco, CA (US); C. Randell Brown, San Francisco, CA (US); Jörg Tatzelt, München (DE)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/823,657

(22) Filed: Mar. 30, 2001

(65) Prior Publication Data

US 2001/0021500 A1 Sep. 13, 2001

Related U.S. Application Data

(63) Continuation of application No. 09/291,406, filed on Apr. 13, 1999, now Pat. No. 6,270,954, which is a continuation-in-part of application No. 08/838,691, filed on Apr. 9, 1997, now Pat. No. 5,900,360.
(60) Provisional application No. 60/015,155, filed on Apr. 10, 1996.

(51) Int. Cl.[7] .......................... C12Q 1/00; C12Q 1/32; C12Q 1/37
(52) U.S. Cl. .................. 435/4; 435/26; 435/23; 435/24; 435/963
(58) Field of Search ................... 435/4, 26, 23, 435/24, 963

(56) References Cited

U.S. PATENT DOCUMENTS 5,276,059 A 1/1994 Caughey et al.
5,900,360 A * 5/1999 Welch et al. ................ 435/29
6,270,954 B1 * 8/2001 Welch et al. ................ 435/4

OTHER PUBLICATIONS

Back, et al., Increased Thermal Stability of Proteins in the Presence of Sugars and Polyols, *Biochemistry*, 18:5191–5196 (1979).
Bilsky, et al., Osmotic Reversal of Temperature Sensitivity in *Escherichia coli*, *Journal of Bacteriology* 113:76–81 (1973).
Brown, et al., Correcting Temperature–sensitive Protein Folding Defects, *J. Clin. Invest.*, 99:1432–1444 (1997).
Brown, et al., Chemical chaperones correct the mutant phenotype of the ΔF508 cystic fibrosis transmembrane conductance regulator protein, *Cell Stress & Chaperones*, 1 (2), 117–125 (1996).
Burg, Molecular basis of osmotic regulation, Walter B. Cannon Lecture, *American Physiological Society* F983–F996, (1995).
Bychkova, et al., Folding intermediates are involved in genetic diseases?, *Federation of European Biochemical Societies*, 359:6–8 (1995).

(List continued on next page.)

*Primary Examiner*—Louise N. Leary
(74) *Attorney, Agent, or Firm*—Townsend and Townsend and Crew LLP

(57) ABSTRACT

A method of improving a phenotypic defect in a cell that contains a conformationally defective target protein wherein the conformational defect causes the phenotype defect, comprising contacting a first cell that expresses said conformationally defective target protein with an amount of a protein stabilizing agent that is effective to improve the conformational defect, thereby improving the phenotypic defect of the first cell in comparison with a second cell having the same conformationally defective target protein and phenotypic defect, wherein the second cell is not contacted with the protein stabilizing agent.

12 Claims, 34 Drawing Sheets

OTHER PUBLICATIONS

Cheng, et al., Functional activation of the cystic fibrosis trafficking mutant ΔF508–CFTR by overexpression, *American Physiological Society*, L615–L624 (1995).

Chowdary, et al., Accumulation of p53 in a Mutant Cell Line Defective in the Ubiquitin Pathway, *Molecular and Cellular Biology*, 14:1997–2003 (1994).

Denning, et al., Processing of mutant cystic fibrosis transmembrane conductance regulator is temperature–sensitive, *Nature*, 358:761–764 (1992).

Edington, et al., Inhibition of Heat Shock (Stress) Protein Induction by Deuterium Oxide and Glycerol: Additional Support for the Abnormal Protein Hypothesis of Induction, *Journal of Cellular Phsiology*, 139:219–228, (1989).

Egan, et al., Differential expression of ORCC and CFTR induced by low temperature in CF airway epithelial cells, *American Physiological Society*, C243–C251 (1995).

Finley, et al., Thermolability of Ubiquitin–Activating Enzyme from the Mammalian Cell Cycle Mutant ts85, *Cell*, 37:43–55 (1984).

Gekko, et al., Mechanism of Protein Stabilization by Glycerol: Preferential Hydration in Glycerol–Water Mixtures, *Biochemistry*, 20:4667–4676 (1981).

Gekko, et al., Thermodynamic and Kinetic Examination of Protein Stabilization by Glycerol, *Biochemistry*, 20:4677–4686 (1981).

Gerlsma, et al., The Effect of Polyhydric and Monohydric Alcohols on the Heat–Induced Reversible Denaturation of Lysozyme and Ribonuclease, *Int. J. Peptide Protein Res.*, 4:377–383 (1972).

Ginsberg, et al., Induction of Growth Arrest by a Temperature–Sensitive p53 Mutant Is Correlated with Increased Nuclear Localization and Decreased Stability of the Protein, *Molecular and Cellular Biology*, 582–585 (1991).

Gordon, et al., Temperature–sensitive Mutations in the Phage P22 Coat Protein Which Interfere with Polypeptide Chain folding, *The Journal of Biological Chemistry*, 268:9358–9368 (1993).

Hawthorne, et al., Osmotic–Remedial Mutants. A New Classification for Nutritional Mutants in Yeast, *Genetics*, 50:892–839 (1964).

Henle, et al., Protection against Heat–induced Cell Killing by Polyols in Vitro, *Cancer Research*, 43:1624–1627 (1983).

Lin, et al., Modification of Membrane Function, Protein Synthesis, and Heat Killing Effect in Cultured Chinese Hamster Cells by Glycerol and $D_2O$, *Cancer Research*, 44:5776–5784 (1984).

Lin, et al., Why do Some Organisms Use a Urea–Methylamine Mixture as Osmolyte? Thermodynamic Compensation of Urea and Trimethylamine N–Oxide Interactions with Protein, *Biochemistry*, 33:12695–12701 (1994).

Maroney, et al., Cloning and characterization of a thermolabile v–src gene for use in reversible transformation of mammalian cells, *Onocogene*, 7:1207–1214 (1992).

Martinez, et al., Cellular localization and cell cycle regulation by a temperature–sensitive p53 protein, *Genes & Development*, 5:151–159 (1991).

Mitraki, et al., Global Suppression of Protein Folding Defects and Inclusion Body Formation, *Science*, 253:54–58 (1991).

Russell, Temperature–Sensitive Osmotic Remedial Mutants of *Escherichia coli*, *Journal of Bacteriology*, 112:661–665 (1972).

Ryan, et al., Alteration of p53 Conformation and Induction of Apoptosis in a Murine Erythroleukemia Cell Line By Dimethylsulfoxide, *Leukemia Research*, 18:617–621 (1994).

Santoro, et al., Increased Thermal Stability of Proteins in the Presence of Naturally Occuring Osmolytes, *Biochemistry* 31:5278–5283 (1992).

Sato, et al., Glycerol Reverses the Misfolding Phenotype of the Most Common Cystic Fibrosis Mutation, *Journal of Biological Chemistry*, 271:635–638 (1996).

Schein, Solubility as a Function of Protein Structure and Solvent Components, *Bio/Technology*, 8:308–317 (1990).

Somero, Protons, osmolytes, and fitness of internal milieu for protein function, *American Physiological Society*, R197–R213 (1986).

Tatzelt, et al., Chemical chaperones interfere with the formation of scrapie prion protein, *The EMBO Journal*, 15:6363–6373 (1996).

Th'ng, et al., The FT210 Cell Line Is a Mouse G2 Phase Mutant with a Temperature–Sensitive CDC2 Gene Product, *Cell*, 63:313–324 (1990).

Thomas, et al., Defective protein folding as a basis of human disease, *TIBS* 20:456–459 (1995).

Welch, et al., Influence of molecular and chemical chaperones on protein folding, *Cell Stress & Chaperones*, 1 (2), 109–115 (1996).

Yancey, et al., Living with Water Stress: Evolution of Osmolyte Systems, *Science*, 217:1214–1222 (1982).

* cited by examiner

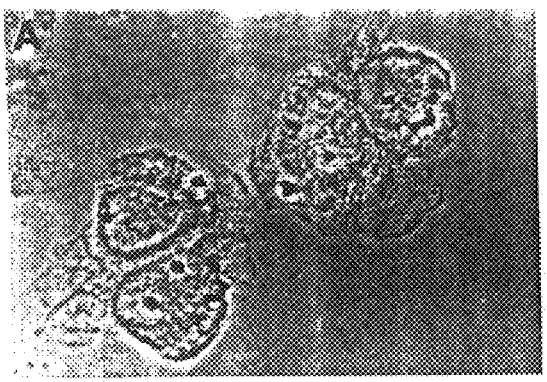
FIG. IIA.
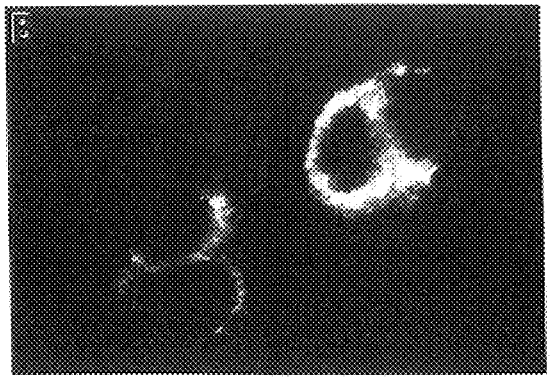
FIG. IIB.
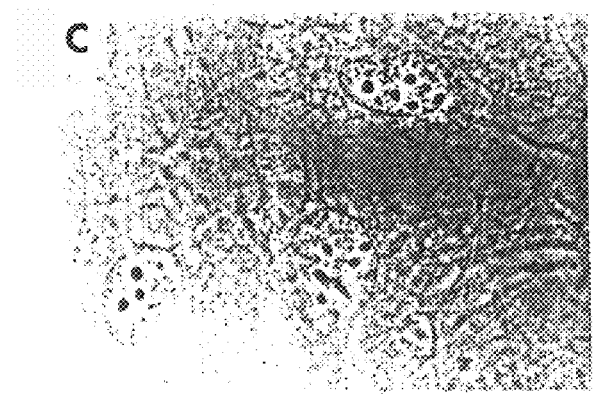
FIG. IIC.
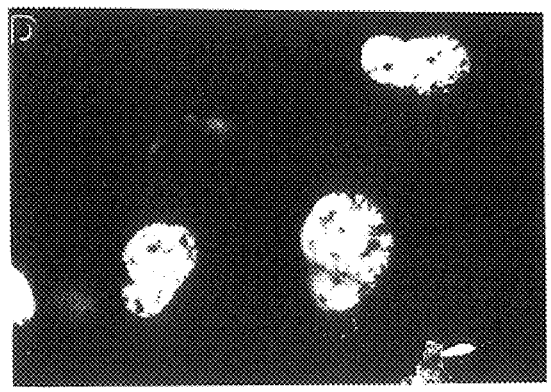
FIG. IID.

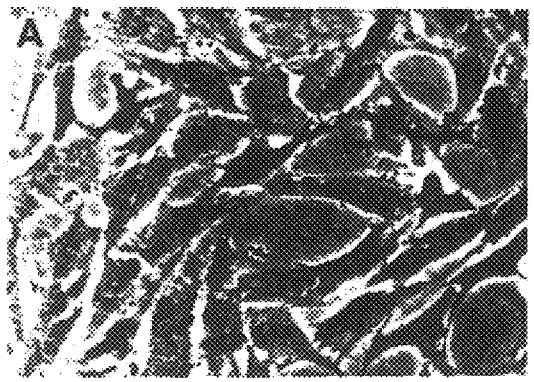
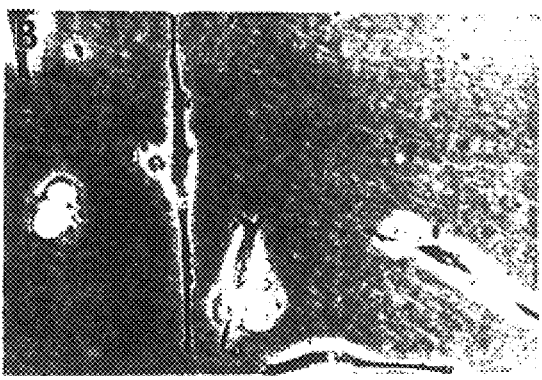
FIG. 16A.  FIG. 16B.
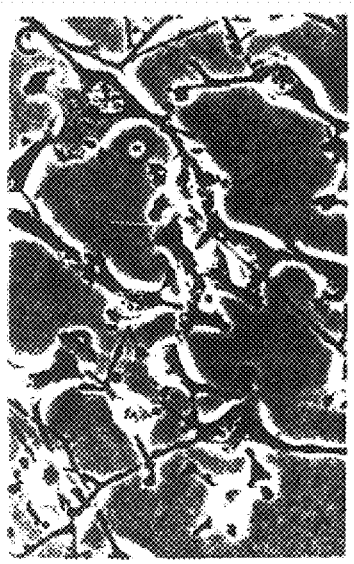
FIG. 16C.  FIG. 16D.  FIG. 16E.

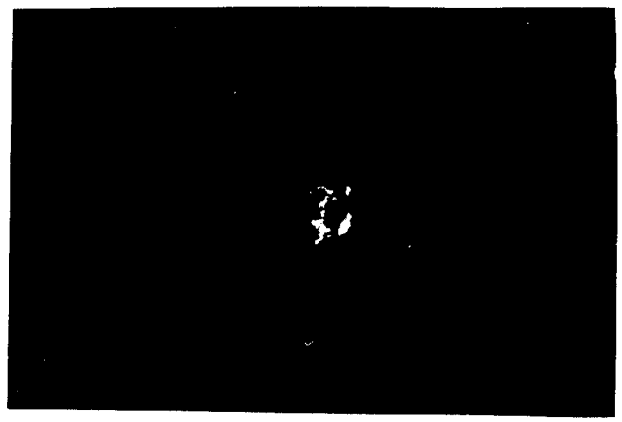
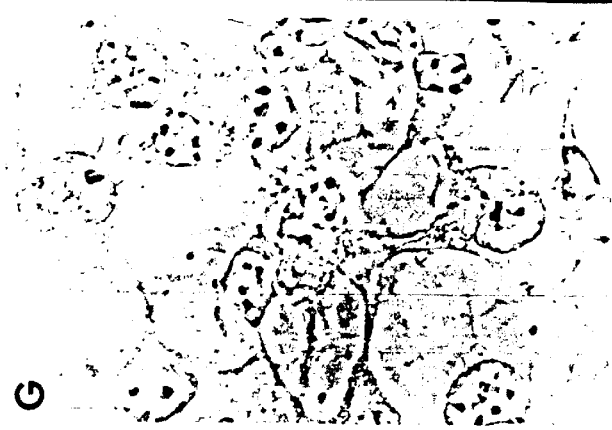
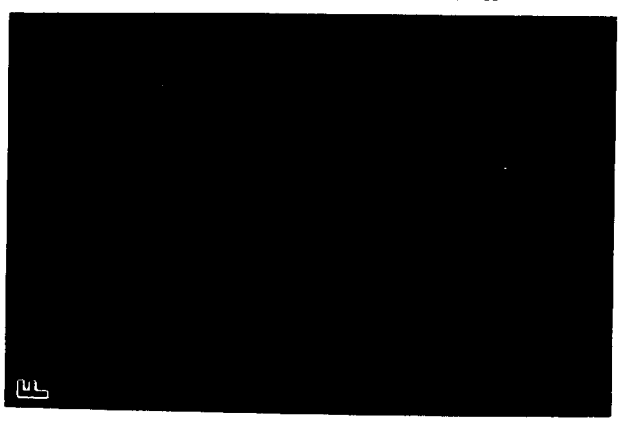
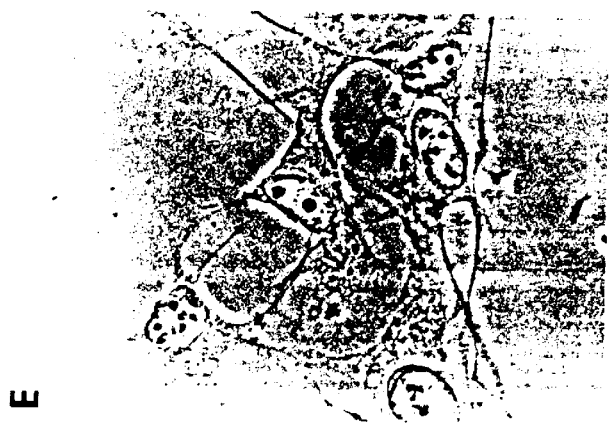
FIG. 18H.
FIG. 18G.
FIG. 18F.
FIG. 18E.

B = betaine  G = glucose  T = taurine

S = sorbitol  M = myo-inositol

CORRECTION OF GENETIC DEFECTS USING CHEMICAL CHAPERONES

This application is a continuation of U.S. Ser. No. 09/291,406, filed Apr. 13, 1999, now U.S. Pat. No. 6,270,954 B1, which is a continuation in part of U.S. Ser. No. 08/838,691, filed Apr. 9, 1997, now U.S. Pat. No. 5,900,360, which claims priority to U.S. provisional application No. 60/015,155, filed Apr. 10, 1996 all of which are incorporated by reference for all purposes.

The government may own certain rights in the present invention pursuant to grants from the Cystic Fibrosis Foundation (R613) and NIH (AG-10770).

BACKGROUND OF THE INVENTION

The present invention relates to the treatment of phenotypic defects that are caused by improper protein folding and processing.

When a protein is synthesized, its amino acid side chains interact, causing the polypeptide backbone to fold into thermodynamically preferred three dimensional structures or "conformations." The biological properties and proper localization (either within the cell or secreted out of the cell) of proteins are contingent on assuming certain biologically significant conformations. Proteins that for whatever reason do not assume "correct" biologically active conformations are inactive and/or misprocessed and/or mislocalized and/or degraded. Failure to assume a proper conformation can lead to disease, and can be fatal. Reviewed in Thomas, P. J. et al., *TIBS*, 20:456–459 (1995).

Abnormalities in protein folding constitute the molecular basis for a number of diseases. Thomas, P. J., et al., 1995, *TIBS* 20:456–459; Welch, W. J. et al., 1996, *Cell Stress & Chap.* 1:109–115. Oftentimes single point or deletion mutations give rise to subtle folding defects that result in either a loss of protein function, or a failure of the protein to be correctly localized. A number of pathological conditions are reportedly the result of improper folding. For example, in cystic fibrosis, a mutation (e.g., ΔF508) which results in improper folding leads to improper targeting of the cystic fibrosis transmembrane conductance regulator; mutant proteins are retained in the endoplasmic reticulum and not delivered to their normal site of action at the plasma membrane. Cheng, S. H. et al., *Cell*, 63:827 (1990); Denning, G. M. et al., *Nature*, 358:761 (1992); Gregory et al., *Mol. Cell. Biol.*, 11:3886 (1991); Kartner et al., *Nature Genet.*, 1:321 (1992); G. M. Denning, G. M. et al., *J. Cell Biol.*, 118:551 (1992). In emphysema and chronic liver diseases, conformational defects result in the failure to secrete alpha-1 antitrypsin inhibitor, leading to tissue damage. Lomas, D. A. et al., *Nature*, 357:605–607 (1992); Lomas, D. A. et al., *Am. J. Physiol.*, 265:L211–219 (1993). In familial hypercholesterolemia, a mutation within the coding region of low density lipoprotein (LDL) receptor results in a failure of the protein to localize to the plasma membrane, leading to abnormal levels of serum cholesterol and heart disease. Amara, J. F. et al., *Trends Cell Biol.*, 2:145–149 (1992); Hobbs, H. H. et al., *Annu. Rev. Genet.*, 24:133–170 (1990); Yamamoto, T. et al., *Science*, 232:1230–1237 (1986). In Tay Sachs disease, a mutation within the coding region of the alpha subunit of beta-hexosaminidase is not delivered to its normal lysosomal location; the mutant protein is instead retained in the endoplasmic reticulum. Amara, J. F. et al., supra; Lau, M. M. H. et al., *J. Biol. Chem.*, 264:21376–21380 (1989). Other diseased states that are due to improperly folded protein are known in the art. Bychkova, V. E. et al., *FEBS Let.*, 359:6–8 (1995); Thomas, P. J. et al., *Trends Biol. Sci.*, 20:456–459 (1995).

Factors which influence a protein's preferred conformation include amino acid sequence, intra- and intermolecular charge interactions, hydrophobic interactions, steric interactions, Van der Waals forces, and disulphide bond linkages; reversible and irreversible post-translational modification (e.g., phosphorylation or glycosylation); degree of hydration; and nature and composition of the solvent medium.

The primary driving force for assuming a biologically active conformation in vivo is thought to be the amino acid sequence. Certain proteins have been shown to spontaneously fold to assume their proper conformation, even after repeated cycles of denaturation and renaturation. Changes in sequence (e.g., mutations) may result in dramatic conformational alterations.

A number of low molecular weight compounds are reportedly effective in stabilizing proteins in vitro against thermally induced denaturation. Germsla, et al., 1972, *Int. J. Pept. Proteins Res.* 4:372–378; Back, J. F., et al., 1979, *Biochem.* 18:5191–5199; Gekko, K. et al., 1983, *J. Biochem.* 94:199–208. Representative compounds include polyols such as glycerol, solvents such as DMSO, and deuterated water ($D_2O$). In addition to their effects in vitro some of these compounds appear to influence protein folding and/or stability in vivo. Lin, P. S. et al., 1981, *J. Cell. Physiol.* 108:439–448; Henle, K. J. et al., 1983, *Cancer Res.* 43:1624–1633; Edington, B. V. et al., 1989, *J. Cell. Physiol.* 139:219–228. For example, animal cells incubated in the presence of either deuterated water or glycerol can withstand severe heat shock treatments that would otherwise be lethal to the cells. Here addition of the compounds to the cells helps to reduce the overall extent of thermal denaturation of intracellular proteins. In yeast and bacteria, the addition of glycerol into the growth medium not only protects the cells against thermal treatments, but in some cases also is effective in correcting protein folding abnormalities due to specific mutations. Hawthorne, D. C. et al., 1964, *Genetics* 50:829–839. This type of "osmotic remediation" has been shown to be the most effective for those mutant proteins which exhibit a temperature sensitive protein folding defect.

Some proteins appear to require interaction with other molecules in order to fold properly. Substances that aid proteins to assume their biologically active conformations have been identified in a variety of cell types and cell compartments. Fischer, G. et al., *Biochemistry*, 29:2206–2212 (1990); Freedman, R. B., *Cell*, 57:1069–1072 (1989); Ellis et al., *Annu. Rev. Biochem.*, 60:337–347 (1991). Among the best known are a class of proteins called "molecular chaperones" (Dingwall, C. K. et al., *Seminars in Cell Biol.*, 1:11–17 (1990)); (Hemmingsen, S. M. et al., *Nature*, 333:330–334 (1988)), or "polypeptide chain binding proteins" (Rothman, J. E., *Cell*, 59:591–601 (1989)). Chaperones stabilize newly synthesized polypeptides until they are assembled into their proper native structure or until they are transported to another cellular compartment, i.e., for secretion. Sambrook et al., *Nature*, 342:224–225 (1989); U.S. Pat. No. 5,474,914, which issued to R. Spaete on Dec. 12, 1995. They reportedly prevent the formation of undesirable protein aggregates by binding to unfolded or partially denatured polypeptides.

The heat-shock proteins of the hsp70 and hsp60 families are examples of chaperones. Langer, T. et al., *Curr. Topics in Microbiol. and Immun.*, 167:3–30 (1991); Pelham, H. R. B., *Nature*, 332:776–777 (1988); and Hartl, F., *Seminars in*

Immunol. 3, (1991). U.S. Ser. No. 07/261,573, filed Oct. 24, 1988, described the folding function of hsp60, isolated from yeast mitochondria. See also McMullin, T. W. et al., *Molec. Cell. Biol.* 8:371–380 (1988); Reading, D. S. et al., *Nature,* 337:655–659 (1989); Cheng, M. Y. et al., *Nature,* 337:620–625 (1989); Ostermann, J. et al., *Nature,* 341:125–130 (1989); and Cheng, M. Y. et al., *Nature,* 348:455–458 (1990)). The essential role in protein folding of the members of the hsp60 family has since been demonstrated in vivo and in vitro. Other chaperones include the rubisco binding protein of chloroplasts, reviewed by Barraclough, R. et al., *Biochim. Biophys. Acta,* 608:19–31 (1980); Musgrove, J. E. et al., *Eur. J. Biochem.,* 163:529–534 (1987); and Gatenby, A. A. et al., *Rev. Cell Biol.,* 6:125–149 (1990), and proteins such as GroEL, isolated from *E. coli* (Georgopoulos, C. et al., *J. Molec. Biol.,* 76:45–60 (1973); Stomborg, N. J., *Molec. Biol.,* 76:25–44 (1973); Hendrix, R. W. J.,*Molec. Biol,* 129:375–392 (1979); Bochkareva, E. S. et al., *Nature,* 336:254–257 (1988); Goloubinoff, P. et al., *Nature,* 342:884–889 (1989); Van Dyk, T. K. et al., *Nature,* 342:451–453; Lecker, S. et al., *EMBO J.,* 8:2703–2709 (1989); Laminet, A. A. et al.,*EMBO J.,* 9:2315–2319 (1990); Buchner, J. et al., *Biochemistry,* 30:1586–1591 (1991)). U.S. Ser. No. 07/721,974 entitled "Chaperonin-Mediated Protein Folding" and filed on Jun. 27, 1991 by Pranz-Ulrich Hartl and Arthur L. Horwich, described mechanisms and components required for chaperonin-dependent folding of proteins, using the groEL and groES proteins of *E. coli* to reconstitute dihydrofolate reductase (DHFR) and rhodanese. The folding reaction required Mg-ATP and the chaperonin proteins.

SUMMARY OF THE INVENTION

The present invention provides methods of improving phenotypic defects that are caused by conformationally defective target proteins. The methods of the invention comprise exposing a cell that expresses a conformationally defective target protein with an amount of a protein stabilizing agent that is effective to improve the phenotypic defect. The improvement in the phenotypic defect of treated cells is assessed by comparing them with cells having the same conformationally defective target protein and phenotypic defect that are not exposed to the protein stabilizing agent.

Nonlimiting examples of "protein stabilizing agents" include dimethylsulfoxide (DMSO), deuterated water, trimethylamine N-oxide (TMAO), polyols and sugars such as glycerol, erythritol, trehalose (used by plants as an osmolyte) isofluoroside; inositol and sorbitol and polymers such as polyethylene glycol; amino acids and derivatives thereof such as glycine, alanine, proline, taurine, betaine, octopine, glutamate, sarcosine, and gamma-aminobutyric acid.

Nonlimiting examples of defective target proteins to be treated (and, in parenthesis, their associated diseases) include the cystic fibrosis transmembrane conductance regulator ("CFTR") protein (cystic fibrosis), α-1 anti-trypsin inhibitor (emphysema and chronic liver disease), LDL receptor (familial hypercholesterolinemia), β-hexylaminidase (Tay-sachs), fibrillin (Martan syndrome), superoxide dismutase (amyotropic lateral sclerosis), collagen (scurvy) α-ketoacid dehydrogenase complex (maple syrup urine disease), p53 (cancer), type I procollagen pro-α (osteogenesis imperfecta), crystallins (cataracts), rhodopsin (retinitis pigmentosa), insulin receptor (leprechaunism and/or insulin resistance), and prion proteins (e.g., kuru, Creutzfeld-Jakob disease, Gerstmann-Straussler Scheinker Syndrome, fatal family insomnia in humans, scrapie and bovine spongiform encephaly in animals). The cells used in the invention are selected from bacterial, yeast, insect and in particular animal or manunalian cells, including cells engineered to express a mutated form of CFTR called ΔF508.

In one embodiment, treatment of cells expressing the ΔF508 CFTR mutant with glycerol causes the ΔF508 gene product to fold properly, and results in restoring wild-type CFTR activity to cells that express ΔF508. A variety of other chemicals propitiate proper folding, including dimethylsulfoxide (DMSO), deuterated water, and the naturally occurring osmolyte, trimethylamine N-oxide. All of these result in a restoration of normal chloride transport in mutant cells comparable to that of wild type cells.

In another embodiment, we provide an assay for quantifying the conversion of the prion protein PrP from the cellular conformation $PrP^C$ to the pathogenic scrapie form $PrP^{Sc}$. We demonstrate that glycerol, DMSO and TMAO interfere with the conversion of $PrP^C$ to $PrP^{Sc}$.

Cell lines expressing temperature sensitive mutants of: the tumor suppressor protein p53; the viral oncogene protein $pp60^{src}$; or a ubiquitin activating enzyme E1, were incubated at the nonpermissive temperature (39.5° C.) in the presence of glycerol, trimethylamine N-oxide or deuterated water. In each case, the cells now exhibited phenotypes similar to that observed when the cells were incubated at the permissive temperature (32.5° C.), indicative that the particular protein folding defect had been corrected. See also Brown et al., 1997, *J. Clin. Invest.* 99:1432–1444. Thus, protein stabilizing agents are effective in vivo for correcting protein folding abnormalities.

In summary, the use of "chemical chaperones" is effective for the treatment of cystic fibrosis and other genetic diseases which involve defective protein folding and/or a failure in normal protein trafficking and maturation events.

BRIEF DESCRIPTION OF THE FIGURES

FIG. 11. The intracellular localization of temperature sensitive p53 in A1–5 cells incubated at the permissive (32.5° C.) and non-permissive (39.5° C.) temperatures.

FIG. 16. Effects of protein stabilizers on the morphology of ts 20 cells expressing a temperature sensitive enzyme involved in protein ubiquitination.

FIG. 22. Treatment with mammalian cellular osmolytes promotes the proper processing and function of the F508 CFTR protein.

FIG. 23. The effects of osmolytes on the processing of the F508 CFTR protein are concentration and time dependent.

FIG. 25A shows that when cells expressing the mutant DF508 CFTR protein are incubated under hyperosmotic conditions (high salt) the cells begin to accumulate different osmolytes and to different levels.

DEFINITIONS

Figure 1A:
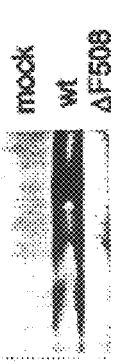
FIG. 1. Effect of incubation with glycerol on the processing and maturation of the ΔF508 CFTR protein.

The term "wild type," when applied to a protein, protein sequence conformation, and/or biological property, denotes a protein, protein sequence, conformation, or biological property predominantly found in nature. Mutant proteins occur less frequently and are often associated with a diseased state.

"Biologically active conformation" denotes a conformation that enables a protein to perform a biological function (e.g., bind ligands, especially with characteristic binding parameters such as binding capacity or binding affinity; enzymatic activity) normally performed by corresponding wild type proteins.

A "conformationally defective target protein" is a protein that is improperly folded in whole or in part at any point during its synthesis or post-translational modification, wherein the improper folding results in: improper targeting, and/or improper post-translational modification, and/or protein aggregation, and/or a detectable phenotypic defect, and/or an inability to perform biological activities performed by wild type proteins. The improper folding may take place within any region of the pre-sequence, pre-protein, pro-sequence, pro-protein or the mature protein. Defective target proteins include the cystic fibrosis transmembrane conductance regulator (CTFR) protein, α-1 anti-trypsin inhibitor (emphysema and chronic liver disease), LDL receptor (familial hypercholesterolinemia), β-hexylaminidase (Tay-sachs), prion protein (scrapies), etc. While any mutation may alter conformation to a degree, this term is specifically directed to mutations that are correctable by the addition of a protein stabilizing agent.

"Phenotypic defect" denotes an observable and preferably readily quantifiable trait in a cell or organism, wherein the defect is caused by a "conformationally defective target protein," that results in a medical condition or diseased state, as compared to wild type individuals whose protein is not conformationally defective.

"Improving a phenotypic defect" denotes causing a phenotypic defect in a cell or organism to observably or measurably become more like the wild type.

"Protein stabilizing agent" is a substance that stabilizes a protein in a biologically active conformation. For most proteins, it acts to stabilize the protein under conditions that can cause denaturation or aggregation. It stabilizes or induces a conformationally defective target protein to assume a biologically active conformation or compensates for its inability to assume a biologically active conformation, and causes a conformationally defective target protein to be processed properly, and/or to be targeted properly, and/or to acquire or retain a biological activity similar to that of the wild-type protein.

An amount of a "protein stabilizing agent" that is effective to improve a phenotypic defect is an amount that, when administered to a cell or individual having a conformationally defective target protein that results in a phenotypic defect, causes the phenotypic defect that is caused by conformationally defective target protein to become more like the phenotypic trait of cells or individuals that express the wild type protein. Protein stabilizing agents usually are administered at concentrations wherein a defective target protein is induced to behave like the wild-type protein, usually 1 μM to 1 M. The precise quantity may vary as a function of the relative potency of the protein stabilizing agent.

"Pre-sequence" refers to an amino acid sequence in a newly synthesized protein which serves as an identification, addressing and sorting "tag" for determining the subcellular destination of the tagged protein, and also as a handle for transporting the protein. This pre-sequence is usually removed as the protein matures. In addition, many proteins are synthesized as relatively inactive "pro-proteins." Pro-proteins can also undergo proteolytic processing, usually involving the removal of a peptide sequence, to yield the mature protein. The "mature protein sequence" is the sequence of the protein after pre- and pro-sequences have been removed or modified.

"Co-translational modification" and "post-translational modification" of a given immature protein to the mature protein includes covalent attachment of sugars, lipids or other functional groups (e.g., phosphate) and chemical modification of amino acid residues.

The term "nucleic acid" refers to a deoxyribonucleotide or ribonucleotide polymer in either single- or double-stranded form, and unless specifically limited, encompasses known analogues of natural nucleotides that hybridize to nucleic acids in manner similar to naturally occurring nucleotides. Unless otherwise indicated, a particular nucleic acid sequence implicitly provides the complementary sequence thereof, as well as the sequence explicitly indicated. The term nucleic acid is used interchangeably with gene and cDNA.

The phrase "heterologous nucleic acid" generally denotes a nucleic acid that has been isolated, cloned and introduced into and/or expressed in a cell or cellular environment other than the cell or cellular environment in which said nucleic acid or protein may be found in nature. The term encompasses both nucleic acids originally obtained from a different organism or cell type than the cell type in which it is expressed, and also nucleic acids that are obtained from the same cell line as the cell line in which it is expressed. Where two nucleic acid sequences not normally combined in nature are ligated together, each is heterologous to the other.

The phrase "a nucleic acid sequence encoding" refers to a nucleic acid which contains sequence information that, if translated, yields the primary amino acid sequence of a specific protein or peptide. This phrase specifically encompasses degenerate codons (i.e., different codons which encode a single amino acid) of the native sequence or sequences which may be introduced to conform with codon preference in a specific host cell.

The term "recombinant" or "engineered" when used with reference to a cell indicates that the cell replicates or expresses a nucleic acid or expresses a peptide or protein encoded by a nucleic acid, whose origin is exogenous to the cell. Recombinant cells can express nucleic acids that are not found within the native (nonrecombinant) form of the cell. Recombinant cells can also express nucleic acids found in the native form of the cell wherein the nucleic acids are re-introduced into the cell by artificial means.

A "composition comprising prion proteins" denotes an organ, tissue, cell, subcellular preparation, or solution that contains either $PrP^C$ or a mixture of $PrP^C$ and $PrP^{Sc}$.

DETAILED DESCRIPTION

The present invention is directed to "chemical chaperones" that improve a broad range of phenotypic defects which are the result of improper conformation, improper cotranslational or post-translational modification, inability to bind biological ligands, improper protein targeting, and/or loss of biological activity relative to the wild type protein.

The chemical chaperones of the invention induce defective proteins to assume biologically active conformations, and/or exhibit correct subcellular targeting, and/or retain or acquire biological activity similar to that of the wild-type protein.

The prior art focuses mainly on the in situ effects of naturally occurring protein chaperones. Since these are nonpermeant intracellular proteins, they are unsuitable for administration to cells to remedy phenotypic defects, unless special steps are taken to ensure that they penetrate into the cell. The protein stabilizing agents provided herein are vastly easier to obtain, chemically more stable, and easier to administer than prior art chaperones which are produced endogenously. Specifically, the chemical chaperones of the invention are readily taken up by the cell.

In what follows, methods for identifying substances that function as protein stabilizing agents are discussed, using as the model a cell line expressing the mutant $\Delta F508$ CFTR or a cell line which expresses $PrP^{Sc}$. We then teach how to determine whether a given phenotypic defect is treatable with a protein stabilizing agent. Finally, the feasibility of practicing the invention is shown by providing specific examples of improving phenotypic defects using selected protein stabilizing agents and several conformationally defective target proteins: $\Delta F508$ CFTR, prion proteins, the tumor suppressor protein p53; $pp60^{src}$, the transforming protein encoded by Rous sarcoma; and an enzyme, E1 which catalyzes the first step in the pathway of protein ubiquitination.

A. Protein Stabilizing Agents

Specific protein stabilizing agents encompassed by the invention include dimethylsulfoxide (DMSO), deuterated water, trimethylamine N-oxide (TMAO), polyols and sugars such as glycerol, erythritol, inositol, trehalose (used by yeast as an osmolyte) isofluoroside; polymers such as polyethylene glycol; amino acids and derivatives thereof, such as glycine, alanine, proline, taurine, betaine, octopine, glutamate, sarcosine, gamma-aminobutyric acid, and trimethylamine N-oxide (TMAO). The invention is not limited to any specific agents. Indeed, any relatively nontoxic substance that functions as a protein stabilizing agent will do. This includes agents such as cellular osmolytes.

B. Assays to Identify Protein Stabilizing Agents

Protein stabilizing agents that are not specifically disclosed herein may be routinely identified by any of the following model methods. As a threshold test, candidate protein stabilizing agents can be identified by their ability to stabilize in vitro certain physical (e.g., reduce aggregation in response to chemical or thermal treatment) and functional (e.g., retain enzymatic activity in response to chemical or thermal treatment) properties of either wild type or conformationally defective proteins. Candidate agents can then be tested in cellular systems such as the mutant CFTR and prion protein expressing cell lines described below. These assays are also useful to determine the relative potency of different protein stabilizing agents, by comparing the ability of a putative protein stabilizing agent to stabilize a biologically active conformation or to induce a conformationally defective protein to become more like the wild type protein, relative to a known well characterized standard protein stabilizing agent (e.g., glycerol).

1. Physical property assays

One method of defining whether a test substance is a "protein stabilizing agent" is to determine its ability to stabilize a protein in vitro to aggregation induced by thermal treatment, changes in pH, or the addition of protein chaotropes (e.g., urea, guanidinium chloride). The assay is performed, for example, by (1) incubating 0.1 to 10 mg/ml of a test wild type protein in the presence or absence of preselected concentrations (ranging from about 0.1 μM to about 1 M) of a test compound, (2) subjecting the test protein to denaturing conditions, (3) measuring the alterations, if any, in the test protein's physical properties (e.g., light absorbance, aggregation, solubility in a specific solvent, α-helix or β sheet content, shape) in the presence or absence of the test compound, and (4) assessing the ability of the test protein to retain wild type behavior and physical properties in the presence and absence of the test substance. For example, the physical property may be a tendency to aggregate in a given solution. Aggregation may be measured by light scattering, velocity sedimentation, or other known techniques. Conditions which cause aggregation include thermal treatment (incubation at 10–70° C.), pH treatment (e.g., incubation at a pH selected from pH 2–10), or the addition of protein chaotropes (e.g., 1–8 M urea or guanidinium chloride). Many others are known in the art and are encompassed by the invention. Protein stabilizing agents are those test substances which reverse, reduce, or prevent the effects (e.g., denaturation, aggregation) of the protein denaturing agent (e.g., acid, detergent) or treatment (pH, temperature).

Another method of testing whether a test substance is a "protein stabilizing agent" is to determine the ability of a specific concentration (or range of concentrations) of a test substance to cause a conformationally defective target protein having a physical property that is measurably different from that of the wild type protein to become more like the wild type. For example, the test protein may tend to aggregate under conditions in which the wild type protein does not aggregate. Aggregation is measured as described above. Test substances which reverse, reduce, or prevent the aggregation of the test protein and thus cause it to behave more like the wild type protein are protein stabilizing agents.

2. Biological activity assays

Another method of determining whether a test substance is a "protein stabilizing agent" is to measure the biological activity of a particular test protein (e.g., enzymatic activity of an enzyme such as β-galactosidase, luciferase, ribonuclease, lysozyme, etc.) in response to protein destabilizing conditions in the presence and absence of test substances.

For example, a test wild type enzyme is exposed to protein destabilizing conditions as described in the previous section (thermal treatment, pH treatment, chaotrope or detergent treatment) in the presence and absence of a defined range of concentrations of a test substance, and the enzymatic activity of the test enzyme under either set of conditions is determined using methods known in the art. A protein stabilizing agent is a test substance that, when present in a defined concentration, results in at least 10% higher activity in the presence of the putative protein stabilizing agent as compared to the same protein exposed to the same destabilizing conditions in the absence of the putative agent.

As a further example, cells expressing a test wild type enzyme are exposed to protein destabilizing conditions as described above, in the presence and absence of a defined range of concentrations of a test substance, and the enzymatic activity of the test enzyme at each concentration of the test substance is determined using methods known in the art. A protein stabilizing agent is a test substance that, when present in a defined concentration, results in at least 10% higher activity in the presence of the putative protein stabilizing agent as compared to the same test performed in the absence of said agent.

As still another example, a cell line that expresses a phenotypic defect associated with the gene product of a homologous or heterologous gene is tested for the presence of a measurable biological activity, such as enzymatic activity, normally associated with the wild type protein but not with the conformationally defective target protein. For example, this activity may be temperature-sensitive. A temperature-sensitive protein or activity is one that is less active than the wild type protein or activity at a particular defined ("non-permissive") range of temperatures, but behaves more like the wild type at a second defined ("permissive") range of temperatures. For example, temperature-sensitive proteins in mammalian cells are often active under 30° C. the "permissive"temperature), but are relatively inactive at 37° C. (the "non-permissive" temperature). A protein stabilizing agent is a test substance that, when present in a defined concentration, causes the enzyme to retain or acquire at least 10% of the wild type activity at the non-permissive temperature.

3. Assays utilizing ΔF508 CFTR-expressing cell lines

Still another method of identifying a protein stabilizing agent involves the use of mutant ΔF508 CFTR-expressing cell lines as described below in greater detail in Example 1. Briefly, a ΔF508 CFTR-expressing line is produced by introducing either the wild type CFTR or a mutant ΔF508 CFTR-encoding nucleic acid (e.g., ΔF508 ) into a cell type which does not normally express the CFTR protein (e.g., NIH 3T3 fibroblasts). Different concentrations of a test substance, generally ranging from 0.1 μM to about 1 M, are dissolved in tissue culture medium. Equal numbers (about $10^5$ or more) of mutant ΔF508 CFTR-expressing cells and control (wild-type CFTR-expressing) cells are incubated at the selected concentration for about 1 hour to about several days, preferably 12–72 hours. The effects of the chemical chaperones are then examined by the biochemical methods described below. For example, the subcellular distribution of ΔF508 CFTR is determined using biochemical assays as described below, and/or immunofluorescent localization. In addition, the cultured cells are optionally analyzed for forskolin-dependent chloride efflux. A test substance that results in the proper folding and modification of the mutant ΔF508 CFTR protein, and its movement to the plasma membrane, which results in the appearance of functional forskolin sensitive chloride channels, and/or forskolin-dependent chloride effluxes that are at least 20% (and preferably at least 50%) of that observed for cells expressing wild type CFTR is a "protein stabilizing agent."

By way of background, mature CFTR is an approximately 160 kDa glycoprotein present in epithelial cells, where it functions as a forskolin dependent chloride channel. 20–25% of newly synthesized wild type CFTR protein exits from the ER and moves to the plasma membrane. The remainder is retained at the ER and eventually is targeted for degradation.

A large number of mutations within the coding region of the gene encoding the CFTR protein have been described, many of which result in a failure of the newly synthesized protein to move out of the endoplasmic reticulum (ER) to the plasma membrane. Rommens, J. M. et al., *Science,* 245:1059 (1989); Riordan, J. R. et al., *Science,* 245:1066 (1989); Kerem, B. S. et al., *Science,* 245:1073 (1989). Defective intracellular transport and processing of the CFTR protein appears to constitute the primary lesion associated with patients having cystic fibrosis. Cheng, S. H. et al., *Cell,* 63:827 (1990); Denning, G. M. et al., *Nature,* 358:761 (1992); Gregory et al., *Mol. Cell. Biol.,* 11:3886 (1991); Kartner et al., *Nature Genet.,* 1:321 (1992); G. M. Denning, G. M. et al., *J. Cell Biol.*, 118:551 (1992). The ΔF508 mutant is but one example of mutations that are useful in the assays described below.

In the mutant ΔF508 CFTR, a phenylalanine normally present at position 508 of the wild type CFTR is deleted. This deletion results in abnormal folding of the protein and retention at the ER. The vast majority (>99%) of the newly synthesized ΔF508 mutant CFTR appears never to leave the ER and is degraded. Yang, Y., et al., *Proc. Natl. Acad. Sci.*, 90:9480 (1993); Pind, S., et al., *J. Biol. Chem.*, 269:12784 (1994).

The folding defect associated with the mutant ΔF508 CFTR is temperature-sensitive. The defect is manifested in cells incubated at about 32–37° C. Cells expressing the ΔF508 mutant that are incubated at lower growth temperatures (e.g., below 30° C.) properly process at least a portion of the mutant protein and now exhibit forskolin stimulated chloride transport. Denning, G. M. et al., *Nature*, 358:761 (1992).

Figure 1B:

The wild type ΔF508 CFTR protein is normally core-glycosylated in the endoplasmic reticulum, and terminally glycosylated in the Golgi and the plasma membrane. The mature wild type CFTR has a molecular weight of about 160 kDa. Newly synthesized ΔF508 CFTR is retained at the level of the endoplasmic reticulum, and, therefore, is not terminally glycosylated. Accordingly, only core glycosylated, immature forms of the ΔF508 CFTR protein having a molecular weight of about 140 kDa are observed at the nonpermissive temperature (e.g., 37° C.) in NIH 3T3 cells transfected with the ΔF508 mutant (FIG. 1). The presence of terminally glycosylated 160 kDa forms of the ΔF508 CFTR is indicative that the endoplasmic reticulum block of the mutant ΔF508 CFTR has been overcome.

Nucleic acids encoding ΔF508 CFTR protein or other selected genes are introduced intocells by methods known in the art. (Although the following discussion focuses on ΔF508, it is applicable to any other gene introduced into and expressed in engineered cells.) Standard eukaryotic transduction methods are used to produce cell lines which express ΔF508 CFTR protein. It is expected that those of skill in the art are knowledgeable in the numerous systems available for cloning and expressing nucleic acids.

The expression of natural or synthetic nucleic acids is typically achieved by operably linking a nucleic acid of interest (e.g., one encoding ΔF508) to a promoter (which is either constitutive or inducible) and incorporating the construct into an expression vector. The vectors are suitable for replication and integration in prokaryotes, eukaryotes, or preferably both. Typical cloning vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See, Giliman, *Gene*, 8:81–97 (1979); Roberts et al., *Nature*, 328:731–734 (1987); Berger et al., *Guide to Molecular Cloning Techniques, Methods in Enzymology*, volume 152, Academic Press, Inc., San Diego, Calif. (Berger); Sambrook et al. (1989), Molecular Cloning—a Laboratory Manual (2nd ed.) Vol. 1–3, Cold Spring Harbor Laboratory, Cold Spring Harbor Press, New York, (Sambrook); and F. M. et al., Current Protocols in Molecular Biology, eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill.

Once a nucleic acid is synthesized or isolated and inserted into a vector and cloned, one may express the nucleic acid in a variety of recombinantly engineered cells known to those of skill in the art. Expression of an exogenous nucleic acid can be enhanced by including multiple copies of, for example, a ΔF508 CFTR-encoding nucleic acid in an engineered cell, by selecting a vector known to reproduce in the host, thereby producing large quantities of protein from exogenous inserted DNA (such as pUC8, ptac12, or pIN-III-ompA1, 2, or 3), or by any other known means of enhancing protein expression. ΔF508 CFTR molecules will be expressed when the DNA sequence is functionally inserted into a vector. "Functionally inserted" means that it is inserted in proper reading frame and orientation and operably linked to proper regulatory elements. Typically, a ΔF508 CFTR gene will be inserted downstream from a promoter and will be followed by a stop codon (although production as a hybrid protein followed by cleavage may be used, if desired).

A number of cell types are useful for the practice of this invention and are readily available. These include cells of fibroblastic or epithelial origin which do not express endogenous CFTR. These cells may be of rodent, feline, canine, bovine, equine, ovine, nonhuman primate, or human origin. The cells may be primary isolates, immortalized, or genetically modified using techniques known to those of skill in the art.

The culture of cells is well known in the art. Freshney (1994) (*Culture of Animal Cells, a Manual of Basic Technique*, third edition Wiley-Liss, New York), Kuchler et al. (1977) *Biochemical Methods in Cell Culture and Virology*, Kuchler, R. J., Dowden, Hutchinson and Ross, Inc., and the references cited therein provides a general guide to the culture of cells. Cultured cell systems often will be in the form of monolayers of cells, although cell suspensions are also used.

There are several well-known methods of introducing nucleic acids into animal cells, any of which may be used in the present invention. These include: calcium phosphate precipitation, fusion of the recipient cells with bacterial protoplasts containing the DNA, treatment of the recipient cells with liposomes containing the DNA, DEAE dextran, receptor-mediated endocytosis, electroporation, microinjection of the DNA directly into the cells, infection with viral vectors, etc.

In example 1 below, we have identified chemical compounds which elicit the proper folding and maturation of the ΔF508 CFTR mutant. These include low molecular weight compounds such as glycerol, dimethylsulfoxide (DMSO) and deuterated water, all of which stabilize proteins against thermal denaturation, both in vitro (Kresheck, G. C. et al., *J. Phys. Chem.*, 69:3132 (1965); Back, J. F. et al., *Biochem.*, 18:5191 (1979); Gerlsma, S. Y. et al., *Int. J. Pept. Proteins Res.*, 4:372 (1972); Gekko, K. et al., *J. Biochem.*, 94:199

(1983)) as well as in vivo (Lin, P. S. et al., *J. Cell. Physiol.*, 108:439 (1981); Henle, K. J. et al., *Cancer Res.*, 43:1624 (1983); McIver, D. J. L. et al., *Physiol. Chem. Phys.*, 12:369 (1980); Edington, B. V. et al., *J. Cell. Physiol.*, 139:219 (1989)). Likewise, methylamines such as trimethylamine N-oxide (TMAO) protect proteins from denaturation by urea and high salt. Somero, G. N., *Am. J. Physiol.*, 251:197 (1986).

4. Assays utilizing ts20 cells ts20 cells express a temperature sensitive mutant of the E1 enzyme, a component of the ubiquitin pathway. The E1 enzyme is rendered inactive at the non-permissive temperature (39.5° C.). As a consequence, these cells are unable to carry out ubiquitin-dependent protein degradation events when maintained at 39.5° C. (Kulka, R. G., et al., 1988, *J. Biol. Chem.* 263:15726–15731; Chowdary, D. R., et al., 1994, *Mol. Cell. Biol.* 14:1997–2003). ts20 cells do not proliferate when exposed to the non-permissive temperature.

As demonstrated in Example 5 below, contact with chemical chaperones causes non-proliferating ts20 cells to proliferate. In example 5, ts20 cells growing at 32.5° C. were plated on 60 mm dishes and maintained at this temperature for 16 h. Cells expressing the ts E1 enzyme were then incubated at either 32.5° C. (the permissive temperature) or at 39.5° C. (the non-permissive temperature) in the presence or absence of protein stabilization agents. Cells incubated at 32.5° C. in regular culture medium displayed an exponential rate of growth, while those maintained at 39.5° C. failed to grow.

Because the measure of effectiveness of a given test substance is the proliferation of ts20 cells, the ts20 system not only identifies substances that act as chemical chaperones, but it simultaneously screens out non-toxic compounds. Even if a test substance stabilizes favorable E1 conformations, if the test substance is otherwise toxic, the ts20 cell will not proliferate.

Proliferation can be measured in a number of ways known in the art: rate of degree of thymidine incorporation, direct cell counts, mitotic indices, etc. Generally, test substances that, at 39.5° C. and a given concentration of the test substance, result in a rate of thymidine incorporation, a cell count, or a mitotic index that is at least 2 times higher, preferably at least ten times higher, and most preferably at least fifty times higher than that of ts20 cells maintained at 39.5° C. are classified as possible protein stabilization agents. Their ability to stabilize proteins can be directly tested as described above.

5. Assays for detecting conformational variants of prion proteins

Another method for assessing conformational changes is useful to detect an interference in the conversion of prion proteins to pathogenic forms. The available evidence indicates that prion diseases (e.g., kuru, Creutzfeld-Jakob disease, Gerstmann-Straussler Scheinker Syndrome, fatal family insomnia in humans, scrapie and spongiform encephaly in animals) arise from a conformationally abnormal form of the prion protein ($PrP^C$). Converging lines of evidence indicate that the conformational abnormality involves a transition of the α-helical form of $PrP^C$ into one predominantly consisting of a β-sheet, thereby giving rise to the pathogenic scrapie isoform ($PrP^{Sc}$). Prion-like proteins have been detected in yeast. Wickner, *Science* 264:566 (1994).

Conversion of $PrP^C$ to $PrP^{Sc}$ is reportedly accomplished in at least two ways. In infectious prion diseases, exogenously introduced $PrP^{Sc}$ is reported to interact with and convert cellular $PrP^C$ into the scrapie isoform. In inherited or familial cases, a mutation in the PrP gene likely causes a destabilization of $PrP^C$ which causes some of it to spontaneously convert into $PrP^{Sc}$.

In either case, conversion of $prP^C$ to $PrP^{Sc}$ is accompanied by biochemical changes. For example, $PrP^C$ is soluble in buffers containing nonionic detergents and is sensitive to digestion by added proteases. In contrast, the majority of $PrP^{Sc}$ appears detergent soluble and is relatively more protease resistant.

In Example 2 below, we have devised an assay for rapidly assessing the relative proportion of $PrP^C$ and $PrP^{Sc}$ within a cell or tissue lysate, and have used this assay to identify protein stabilizing agents that interfere with or prevent the conversion of $PrP^C$ to $PrP^{Sc}$. In general, the method comprises (1) incubating a cell line or tissue capable of converting $PrP^C$ to $PrP^{Sc}$ for between one hour to several days in the presence and absence of a defined concentration (0.1–1 M) of a protein stabilizing agent; (2) mixing the cell line or tissue with a solution wherein only one form of PrP, either $PrP^C$ or $PrP^{Sc}$, is soluble; (3) separating the form of PrP that is soluble from the form that is insoluble; (4) determining the relative amounts of each form of PrP; and (5) determining whether the test substance prevents the conversion of $PrP^C$ to $PrP^{Sc}$. One example of a solution that solubilizes preferentially only one form of PrP is a cold (e.g., about 4° C.) solution that comprises about 1% Triton X-100 and about 1% DOC. The soluble and insoluble forms of PrP may be separated by a separation method, such as centrifugation at 15,000–50,000×g for 10–30 min. at 4° C. The PrP in each fraction (supernatant and pellet) may then be quantitated by methods known in the art, such as immunoblotting, ELISA, protein assays, etc. In the above example, most of $PrP^C$ partitions into the soluble phase, while most of the $PrP^{Sc}$ partitions into the insoluble phase.

C. Methods for the Identification and Correction of Diseases Involving Improper Folding and Processing Cystic fibrosis is but one of a number of genetic diseases which arise due to specific mutations that ultimately lead to protein folding errors (reviewed in Thomas, P. J., et al., 1995, *TIBS* 20:456–459; Welch, W. J. et al., 1996, *Cell Stress & Chap.* 1:109–115.); Brown et al., 1996, *Cell Stress & Chap.* 1:117–125.). In addition to demonstrating the feasibility of practicing the invention to treat CFTR and diagnose the presence and severity of prion disease, the present invention also provides methods for identifying and correcting phenotypic defects and medical conditions that are not specifically disclosed herein that are the result of improper protein folding and processing.

In brief, a cell line that is believed to harbor an improperly folded and processed protein that results in a phenotypic defect is exposed to a defined range of concentrations of a known protein stabilizing agent. Candidate cells often (but not always) are cells that express a temperature-sensitive defect, many examples of which have been reported in the literature (e.g., the tumor suppressor gene p53, Martinez et al., *Genes and Development* 5: 151–159 (1991); the G2 phase mutant CDC2, Th'ng et al., *Cell* 63: 313–324 (1990); mutants of the low density lipoprotein (LDL) receptor, Hobbie et al., *J. Biol. Chem.* 269: 20958–20970 (1994); the gene product of the v-src oncogene, Maroney et al., *Oncogene* 7: 1207–1214 (1992); mutants of human P glycoprotein, Loo et al., *J. Biol. Chem.* 269: 28683–28689 (1994); the oncogene protein $pp60^{src}$; an enzyme involved in ubiquitination, etc.). The phenotypic trait is measured before and after exposure to the protein stabilizing agent. The goal of the treatment is to induce the cells to adopt a wild type phenotype for the trait in question. The degree to which the cells attain or approximate a wild type phenotype is a measure of the success of the treatment.

How the phenotypic trait is measured varies as a function of the trait. Where the phenotypic defect results in a protein that retains biological activity (e.g., ability to bind a ligand with similar binding parameters as a wild type protein; enzymatic activity) but is not properly compartmentalized, the appropriate measurement is the extent to which the protein is correctly localized after exposure to a protein stabilizing agent. Where the phenotypic defect involves incorrect post-translational modification or loss of biological activity, a proper measure is, respectively, ability to be correctly processed, or recovery of wild type biological activity. Where the phenotypic defect involves a primarily visual trait (e.g, color, shape, size, cellular morphology, etc.), the appropriate measure is the degree to which the defective cell attains a wild-type color, shape, size or cellular morphology.

For example, Alzheimer's disease involves the proteolytic cleavage of a ~140 kDa amyloid precursor protein into a 40–43 kDA β-amyloid protein, and the subsequent deposition of β-amyloid protein into amyloid plaques. It is reported that plaque formation involves aggregation of the β-amyloid protein. (Kischner, D. A. et al., *PNAS*, 83:503 (1986)). Other diseases involving deposition of "amyloid" proteins are known. It is expected that amyloid deposition is prevented by exposure to chemical chaperones. We note that U.S. Pat. No. 5,276,059 to Caughey et al. reported that Congo Red was useful to treat conditions involving amyloid deposition. We have been unable to repeat this observation.

Protein stabilizing agents used to remedy phenotypic defect that result from folding include glycerol, DMSO, sorbitol and other "protein stabilizing agents" detected as described in the preceding section.

EXAMPLES

Examples 1 and 2 below demonstrate that protein stabilizing agents counter defects caused by certain folding variants of the CFTR gene product and the scrapies protein, without destroying the cells exposed to the agent. Examples 3–5 show that protein stabilizing agents also are effective for correcting other temperature sensitive protein folding mutants. For these studies, cell lines expressing 3 different temperature sensitive folding mutants were examined: the tumor suppressor protein p53; pp60$^{src}$, the transforming protein encoded by Rous sarcoma; and an enzyme, E1, which catalyzes the first step in the pathway of protein ubiquitination. Treatment with the different protein stabilizing ageits resulted in the cells adopting a wild type phenotype at the nonpermissive temperature, indicative that the particular protein folding defect had been corrected. Thus, mutations which result in temperature sensitive protein folding defects are amenable to correction in vivo via the use of protein stabilizing agents. These results have broad implications as they relate to the correction of protein folding defects associated with certain genetic diseases.

Example 1
Correction of ΔF508 CFTR Mutants with Chemical Chaperones

Example 1 demonstrates the feasibility of practicing the invention, using as a model system a cell line genetically engineered to express a cystic fibrosis transmembrane chloride regulator protein (CFTR) mutant that exhibits folding defects. We provide four specific examples of protein stabilizing agents that improve phenotypic defects associated with the ΔF508 mutant.

Example 1A
ΔF508 CFTR and Glycerol

Example 1A demonstrates that incubation of cells with protein stabilizing agent glycerol promotes the maturation and transport to the plasma membrane of the ΔF508 CFTR protein. The first part of this example is a description of the CFTR system, in particular the ΔF508 mutant. The second part relates to the effect of glycerol on the ΔF508 CFTR.

The effect of glycerol was measured by detecting either (1) the maturation of immature core-glycosylated endoplasmic reticulum forms of the ΔF508 CFTR to mature terminally glycosylated forms, or (2) the presence of forskolin-dependent chloride transport.

To study glycosylation patterns, a rabbit polyclonal antibody specific for the R domain of the CFTR protein was produced. A GST fusion protein containing the R domain (amino acids 590–830) of CFTR was prepared by (1) excising from a full length CFTR cDNA sequence a BamH1-HindIII fragment encoding amino acids 590–830; and then (2) ligating this restriction fragment into plasmid pGEX-KG (Stratagene, San Diego) which, when expressed, produces a glutathione S transferase. The resulting ligated plasmid, when expressed in bacteria, yields a CFTR-GST fusion protein which contains a thrombin cleavage site between the GST affinity tag and the CFTR R domain.

To purify the fusion protein, the cells were lysed in buffer containing lysozyme. Inclusion bodies enriched in the recombinant protein were separated via centrifugation at 6500×g for 10 min. at 4° C. The pellet containing inclusion bodies was washed with a buffer containing 0.5 M NaCl, 0.5% Triton X-100, 0.5% sodium deoxycholate, and 10 mM dithiotreitol. The material was repelleted via centrifugation and resuspended in 8 M urea. After dialysis to remove the bulk of the urea, the protein was partially purified by affinity chromatography using a glutathione column, followed by preparative SDS polyacrylamide electrophoresis.

The protein was then eluted out of the gel, mixed with Freund's complete adjuvant, and injected into rabbits. After two subsequent boosts of the antigen (using Freund's incomplete adjuvant), serum was obtained, characterized, and shown to be specific for the CFTR protein or CFTR domain containing amino acids 590–830.

The polyclonal antibody was initially characterized by its ability to immunoblot the GST-R fusion antigen, as well as immunoprecipitate the full length CFTR protein synthesized in vitro. The polyclonal antibody also immunoblotted CFTR expressed in various cell lines (T84, CaCo), in stable transfectants, or in transiently transfected SF9 cells. (Data not shown) For comparative purposes, a mouse monoclonal specific for the C terminus of the CFTR protein was purchased from Genzyme.

Western blotting using a commercially available anti-CFTR monoclonal antibody (panel 1A) or our polyclonal anti-CFTR antibody (Panel 1B) was performed using cell lysates from NIH 3T3 cells transfected with either the wild type or ΔF508 forms of CFTR. Andersen, M. P. et al., *Science*, 253:202 (1991). Both the polyclonal and monoclonal antibodies recognized the 140 kDa (core glycosylated, or B form) and 160 kDa (fully glycosylated, C form) forms of CFTR in lysates from wild type CFTR expressing cells. In contrast, only the 140 kDa core glycosylated CFTR was detected by the two antibodies in the lysates from cells transfected with the ΔF508 CFTR mutant.

In panel 1C, cells expressing the ΔF508 mutant were examined by Western blotting using the rabbit polyclonal antibody following their treatment at 37° C. with 1 M glycerol for 3 days. As a positive control, the ΔF508 CFTR expressing cells were incubated at 26° C. for 3 days.

Figure 1C:
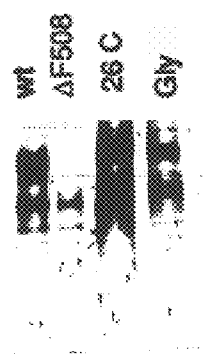

As shown in FIG. 1, incubation of the ΔF508 mutant expressing cells at 26° C. resulted in the appearance of the mature form of the CFTR protein. Similar to the effects of lower temperature, cells incubated at 37° C. in the presence of 1 M glycerol for a period of 3 days now contained significant amounts of the mature ΔF508 CFTR protein (FIG. 1C).

Figure 2A:
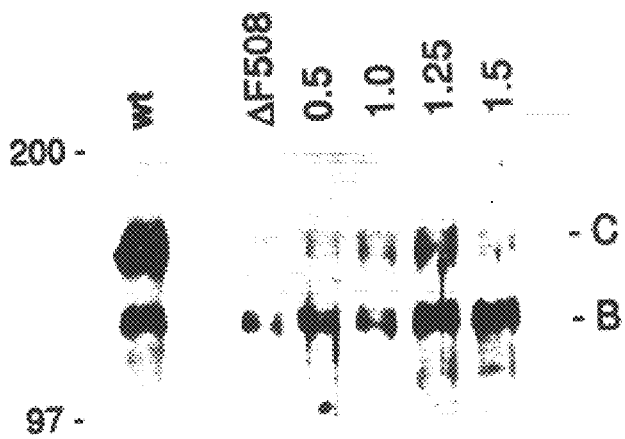
FIG. 2. Concentration and time dependence of the effect of glycerol on ΔF508 CFTR processing.
Figure 2B:
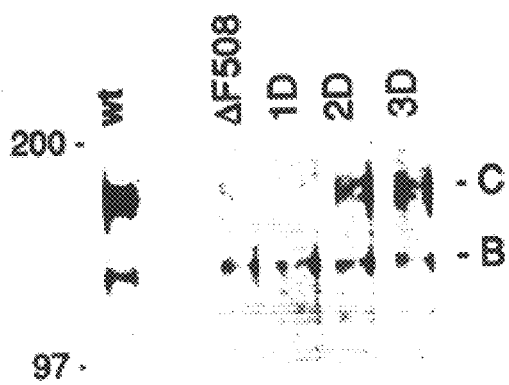

The results of experiments to determine the optimal concentration of glycerol and the duration of glycerol treatment needed to elicit the highest levels of mutant ΔF508 CFTR maturation are summarized in FIG. 2. In panel 2A, cells expressing ΔF508 CFTR were incubated at 37° C. for 3 days in culture medium containing various concentrations of glycerol. The cells were harvested and then analyzed by Western blotting using the rabbit polyclonal anti-CFTR antibody. In panel 2B, cells expressing ΔF508 CFTR were incubated with 1.25 M glycerol at 37° C. for 1, 2 or 3 days and then analyzed by Western blotting as described in A. Glycerol concentrations of 1–1.25 M gave the maximal amount of mutant protein which was properly processed. Lower doses resulted in less of the fully glycosylated protein and higher doses were inhibitory, perhaps due to adverse effects on the cells. At 1.25 M glycerol, a time course study showed maximal amounts of the fully glycosylated ΔF508 CFTR protein after 3 days of treatment.

Figure 3A:
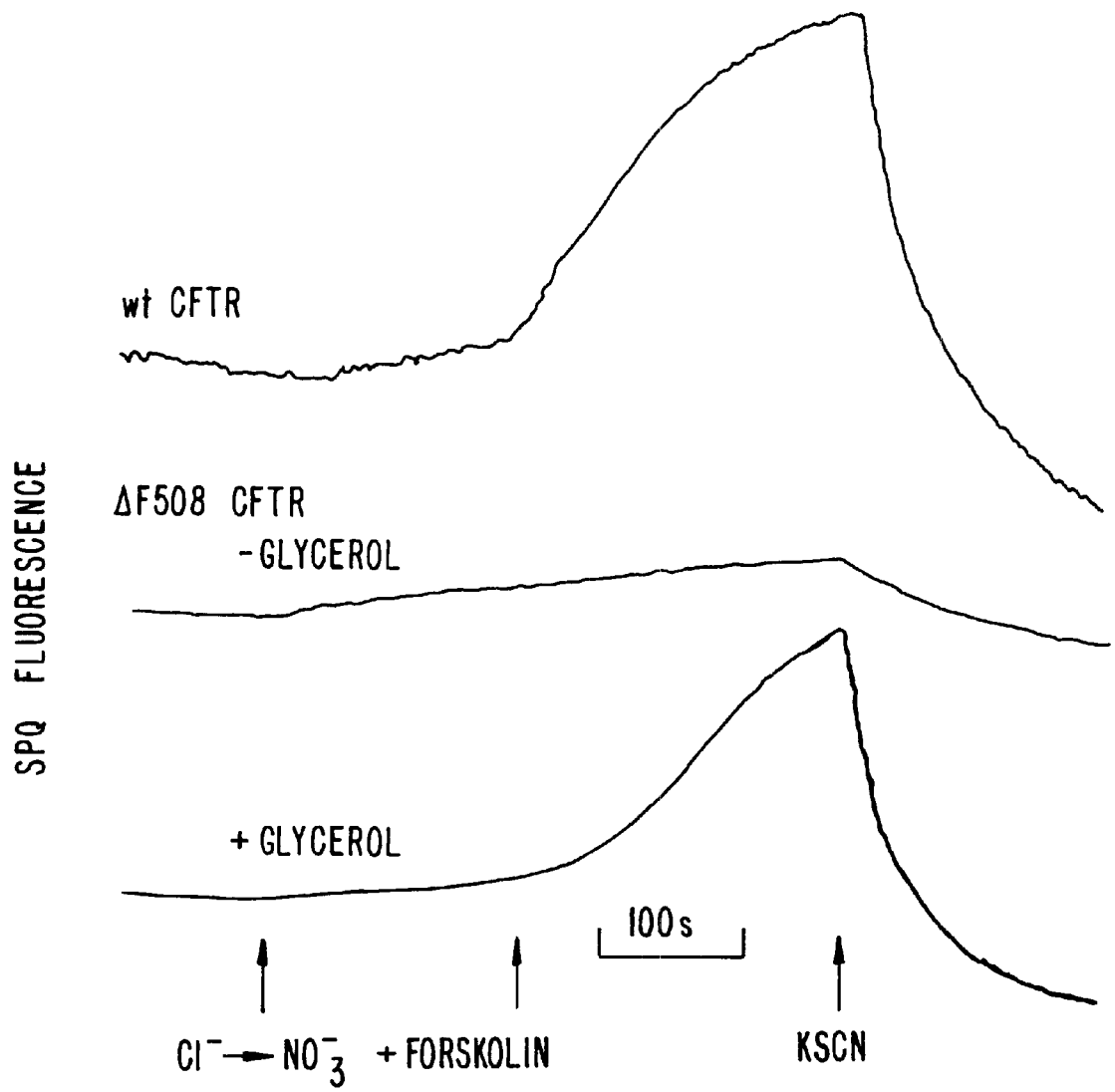
FIG. 3. Effect of glycerol on forskolin dependent chloride transport in ΔF508 CFTR expressing cells.

Forskolin-sensitive chloride transport was measured by the fluorescence assays method (FIG. 3). Briefly, ΔF508-CFTR expressing cells were grown on glass coverslips at 37° C. in the absence or presence of 1.25 M glycerol for 3 days. These cells, along with cells expressing wild type CFTR, then were examined for forskolin stimulated chloride transport using SPQ fluorescence assays, as described in: Verkman, A. S., *Am. J. Physiol.*, 259:C375 (1990); Verkman, A. S. et al., in *Methods in Neurosciences*, Kraicer, J. et al., Eds. (Academic Press, 1995) vol. 27, 328. Plasma membrane chloride efflux was measured from the time course of increase in SPQ fluorescence in response to replacement of intracellular chloride by nitrate. Cells in the presence or absence of a protein stabilizing agent were incubated with 2 mM SPQ for 12–18 hrs. prior to measurements. The rate of chloride efflux was measured before and after stimulation of cAMP with forskolin. The reaction was quenched by the addition of 150 mM KSCN.

In the absence of glycerol, ΔF508 CFTR-expressing cells showed little or no chloride transport. In contrast, after one day of incubation in the presence of 1.25 M glycerol, forskolin stimulated chloride transport was observed. Thus, despite an inability to observe, via Western blotting, any significant levels of the mature ΔF508 CFTR protein in the cells following 1 day of glycerol treatment, the more sensitive fluorescence assay indicated a partial restoration of chloride conductance after one day of glycerol treatment.

Figure 3B:
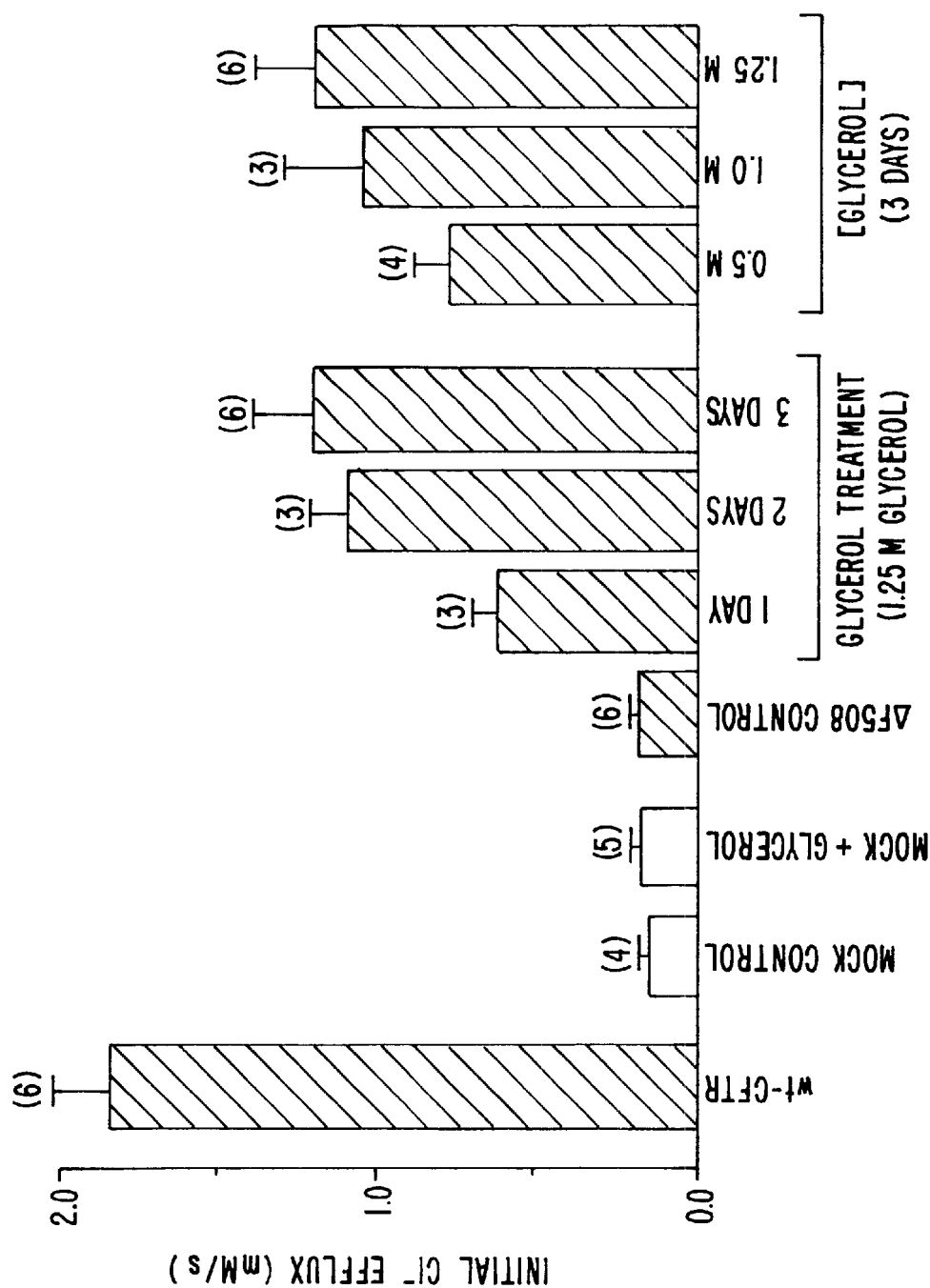

The positive effect of glycerol treatment on chloride conductance was concentration and time dependent (FIG. 3B). ΔF508 CFTR-expressing cells growing on glass coverslips were incubated with various concentrations of glycerol for 3 days and then examined for forskolin stimulated chloride transport. Alternatively, cells were incubated with 1.25 M glycerol for varying times (1, 2 or 3 days) and then analyzed for chloride transport following stimulation by forskolin. Increased chloride transport was observed for cells exposed to as little as 0.5 M glycerol for 3 days. Maximal rates of chloride efflux was observed in those cells incubated in 1.25 M glycerol for a period of 3 days, consistent with the results obtained using Western blotting. Glycerol exposure of the cells expressing the wild type CFTR protein had little or no effect on the amount of the mature protein (via Western blotting) or their forskolin dependent chloride conductance (data not shown). Mock-transfected 3T3 cells, either in the absence or presence of glycerol, did not display significant cAMP stimulated chloride movement (FIG. 3B).

Example 1B
ΔF508 CFTR and Deuterated Water

Applying essentially the same procedures as those used in Example 1A, we demonstrated that deuterated water was a protein stabilizing agent, and that it was competent to induce CFTR processing and forskolin dependent chloride transport in ΔF508 CFTR-expressing cells.

Figure 4:
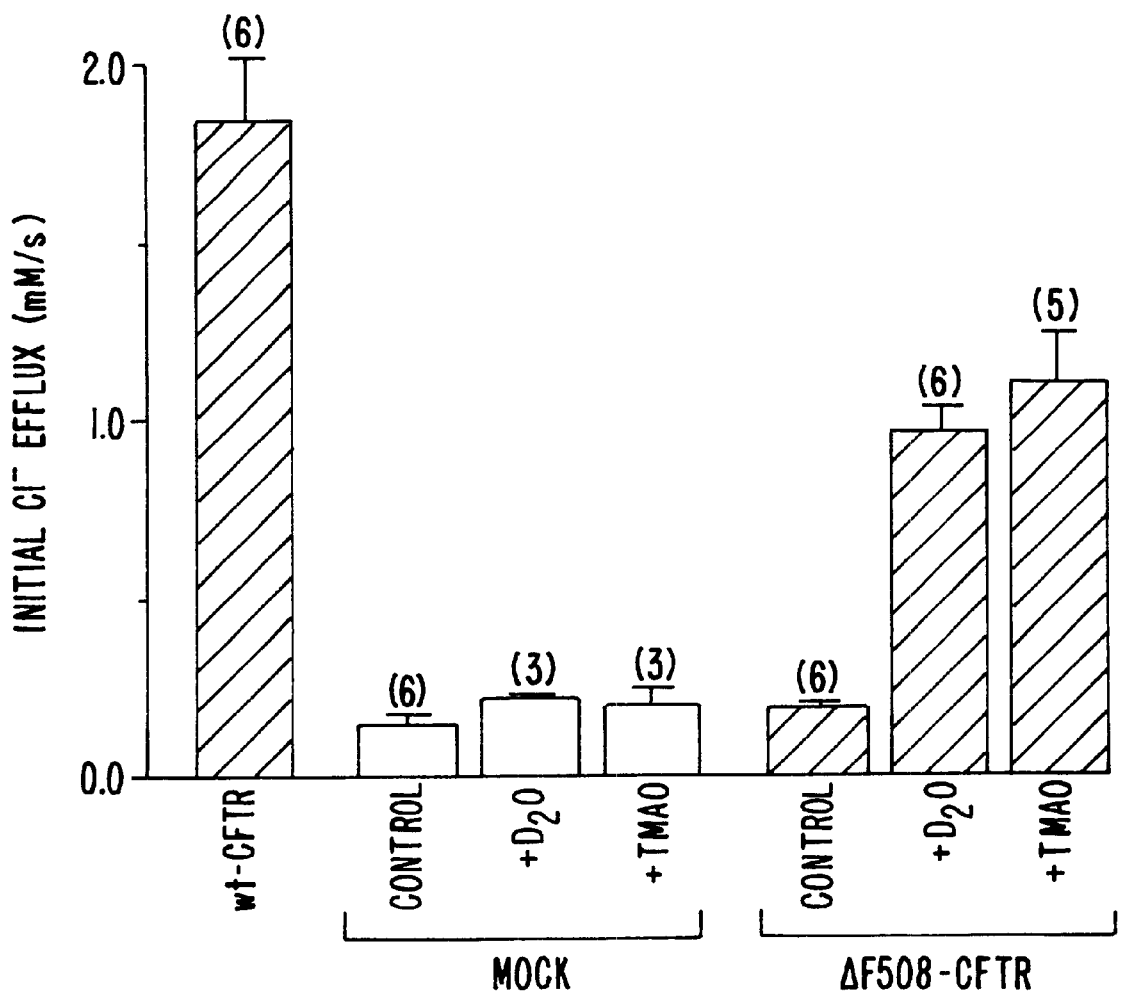
FIG. 4. Effect of deuterated water (dH2O) or trimethylamine N-oxide (TMAO) on forskolin dependent chloride transport in ΔF508 CFTR expressing cells.

Powdered DMEM medium (Gibco) was reconstituted in 100% distilled water or in 100% dH$_2$O (Sigma). Cells transfected with ΔF508 CFTR or mock transfected cells were incubated in either the distilled water or the dH$_2$O containing culture medium for two days at 37° C., and then analyzed for forskolin dependent chloride efflux. As shown in FIG. 4, ΔF508 CFTR expressing cells incubated in the presence of deuterated water (dH$_2$O) exhibited forskolin-dependent chloride transport.

Example 1C
ΔF508 CFTR and TMAO

Trimethylamine N-oxide (TMAO) is a naturally occurring cellular osmolyte which accumulates in the cells of cartilaginous fish (e.g., sharks) in response to high concentrations of the protein chaotrope urea. Methylamines like TMAO are commonly used by a variety of organisms to withstand the protein denaturing effects of high concentrations of urea and/or salt. For example, elasmobrachs (sharks, rays) accumulate significant amounts of TMAO in their tissues (~200 mM), to counteract the denaturing effects of high intracellular concentrations (~400 mM) of urea (Somero, G. N., *Am. J. Physiol.*, 251:R197 (1986)). Thus, it appears that this class of compounds stabilizes proteins.

Both mock transfected cells and the cells transfected with ΔF508 CFTR were incubated in regular DMEM culture medium containing 100 mM TMAO for two days at 37° C. and then analyzed for forskolin dependent chloride efflux. Forskolin dependent chloride transport was observed for the mutant cells treated with 100 mM TMAO for a period of 2 days (FIG. 5).

Example 1D
ΔF508 CFTR and DMSO

Similar results as those shown in FIGS. 1–3 were obtained when the cells were exposed for two days to DMEM medium supplemented with 2% dimethylsulfoxide (data not shown).

Example 1E
Further Confirmation that Treatment with Mammalian Cellular Osmolytes Promotes the Proper Processing and Function of the ΔF508 CFTR Protein In Panel A of FIG. 22, 3T3 cells expressing the ΔF508 CFTR protein (via stable transfection) were treated with either 100 or 200 mM of the specified cellular osmolytes for 2 days. Cells were then lysed and examined by Western blot analysis. Wt represents cells expressing the wild type CFTR protein. B, G, T, S and M indicated cells treated with betaine, glucose, taurine, sorbitol and myoinositol, respectively.

Figure 22A:
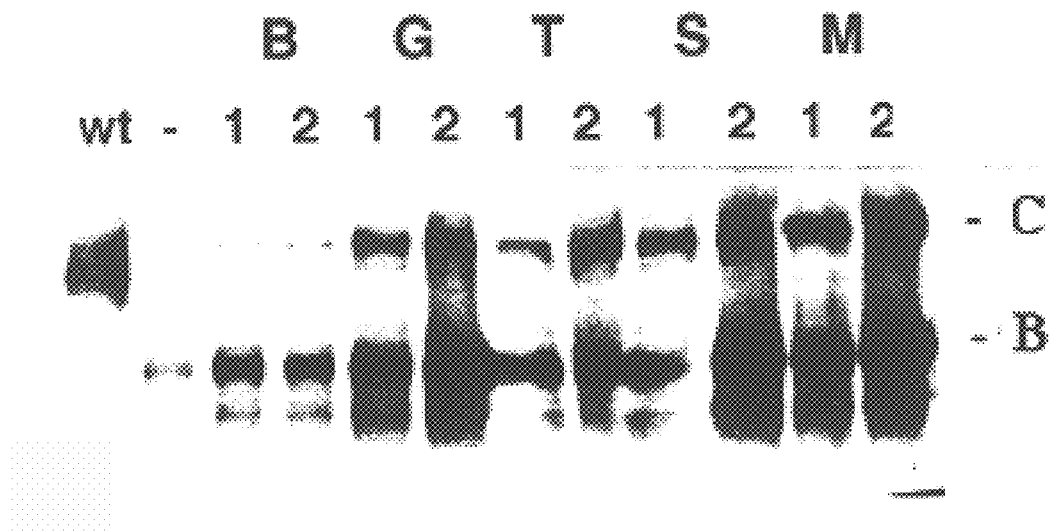
FIG. 22A shows that cells expressing the DF508 mutant protein, when exposed to the different cellular osmolytes, now contain some of the mature protein (band C), similar to the wild type cells.

FIG. 22A shows that cells expressing the ΔF508 mutant protein, when exposed to the different cellular osmolytes, now contain some of the mature protein (band C), similar to the wild type cells. Note the C band in the wild type cells (wt), no C band in the mutants (indicated with a—over the lane), but now with the different osmolyte treatments we see some C band in the cells expressing the mutant protein.

Figure 22B:
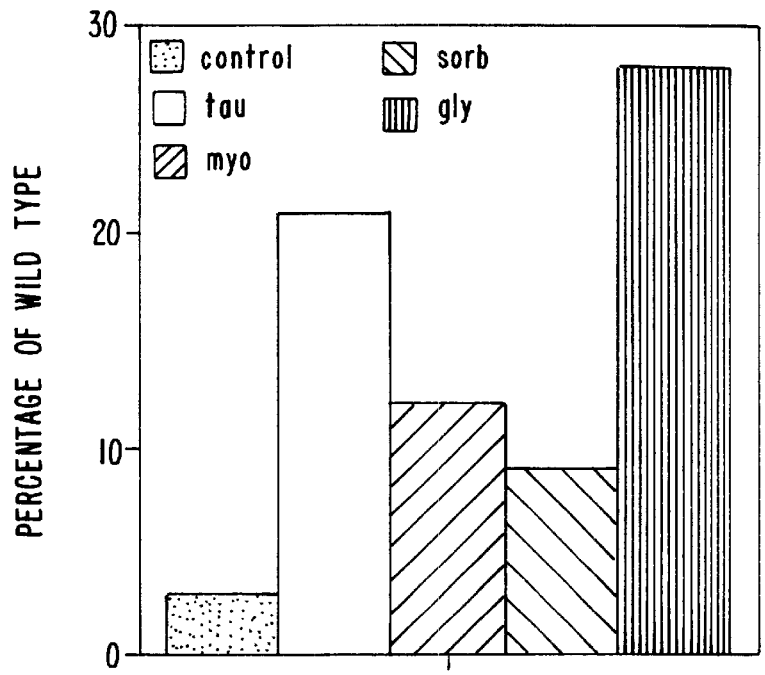
FIG. 22B shows that DF508 cells (control) fail to transport any appreciable chloride ions in response to stimulation with forskolin (plotted as a percentage of chloride transport relative to cells expressing wild type protein). In contrast, cells treated with 4 different osmolytes now show partial chloride transport (note however that it never reaches the wild type levels, rather only about 10–30% of wild type).

In FIG. 22B, the effects of osmolyte treatment on chloride conductance were determined following similar osmolyte treatments as described in panel A. FIG. 22B shows that ΔF508 cells (control) fail to transport any appreciable chloride ions in response to stimulation with forskolin (plotted as a percentage of chloride transport relative to cells expressing wild type protein). In contrast, cells treated with 4 different osmolytes now show partial chloride transport (note however that it never reaches the wild type levels, rather only about 10–30% of wild type).

Figure 22C:
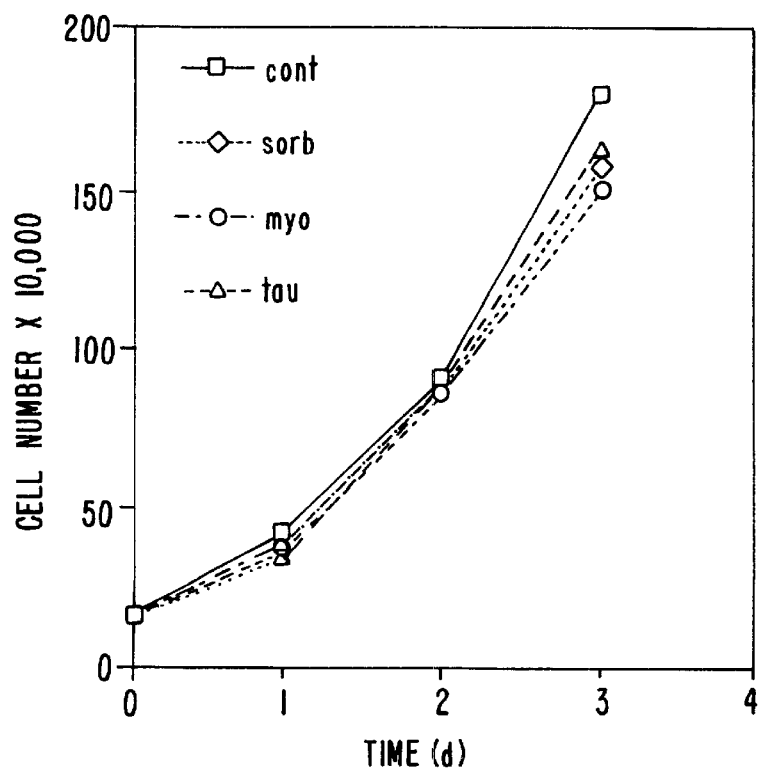
FIG. 22C. Shows that the different treatments are not deleterious to the cells as indicated by continued cell proliferation.

To determine the effects of osmotic treatment on cellular growth, cells growing on 60 mM dishes were maintained in the presence of absence of 200 mM taurine, sorbitol or myo-inositol. Some plates were counted prior to the addition of osmolytes, while the remainder were counted on a daily basis. FIG. 22C shows that the different treatments are not deleterious to the cells as indicated by continued cell proliferation.

Figure 23A:
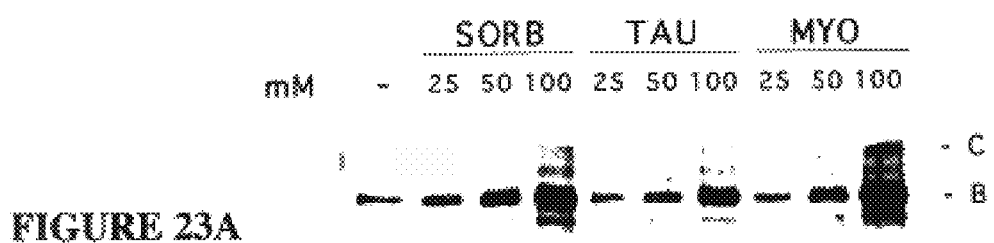
FIG. 23A shows a concentration curve of osmolyte treatment of the cells expressing the mutant protein-note that only the higher concentration (100 mM) appeared effective to elicit the appearance of the mature (band C) form of the CFTR protein.
Figure 23B:
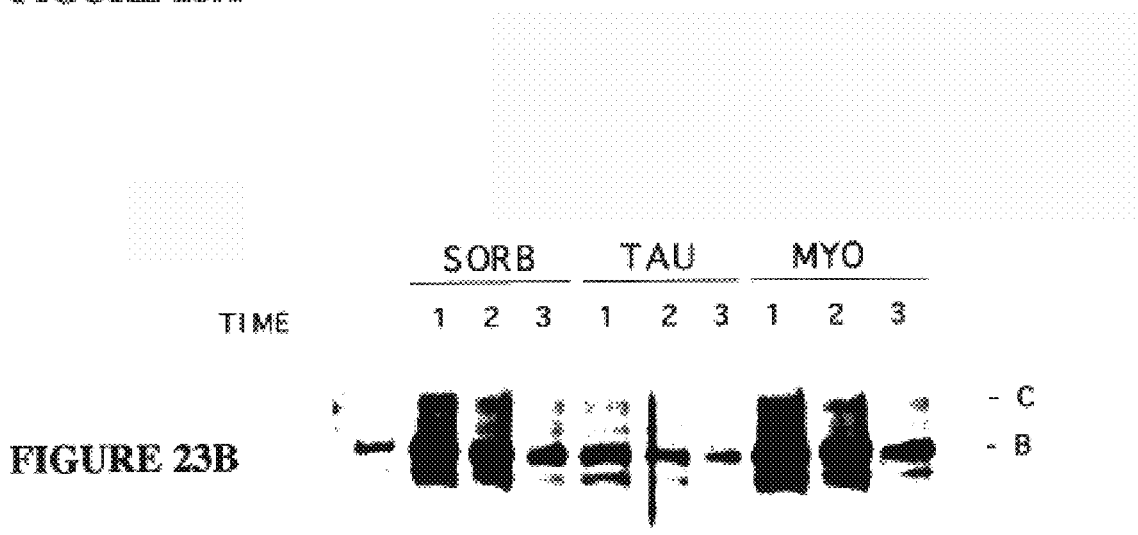
FIG. 23B shows that the positive effects of the osmolytes diminished over time.

FIG. 23 shows that the effects of osmolytes on the processing of the ΔF508 CFTR protein are concentration and time dependent. In Panel A, cells expressing ΔF508 CFTR were incubated in the presence or absence of varying concentrations (25, 50, 100 mM) of osmolyte. After 2 days of growth, the cells were harvested and analyzed for their content of immature (band B) and mature (band C) forms of the CFTR protein by Western blotting. Cells expressing wild type CFTR (wt) were included as a positive control. In Panel B, cells expressing ΔF508 CFTR were incubated for 1 (1D), 2(2D) or 3 (3D) days in growth medium containing 150 mM of the indicated osmolyte. As a control, the same cells were incubated in normal growth medium. FIG. 23A shows a concentration curve of osmolyte treatment of the cells expressing the mutant protein-note that only the higher concentration (100 mM) appeared effective to elicit the appearance of the mature (band C) form of the CFTR protein. FIG. 23B shows that over time in the cells expressing the mutant protein that the positive effects of the osmolytes diminishes. After 3 days of continuous treatment with 150 mM osmolyte there is see a "drop-off" of the amount of the C band.

Figure 24:
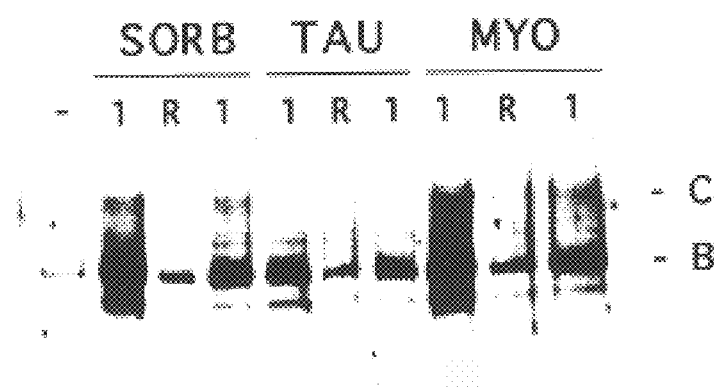
FIG. 24. The effects of osmolyte treatment are reversible but can be reinitiated by a subsequent treatment.

In FIG. 24, cells expressing the ΔF508 CFTR protein were treated with the specified osmolyte for 1 D. At the end of this period, some cells were harvested (1), while others were washed and further incubated for 1 D in normal growth media (R). A third group of cells was treated for 1 day, washed and recovered for 1D and then given another 1D treatment with the specified osmolyte. FIG. 24A shows that the effects of the osmolytes are reversible.

Figure 25:
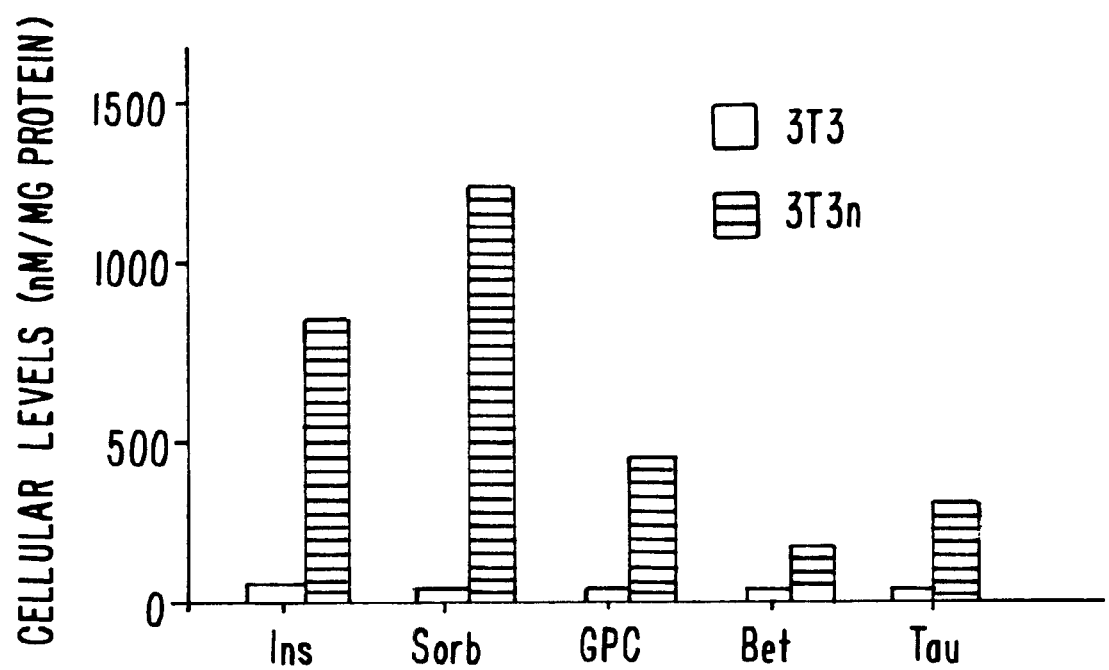
FIG. 25. 3T3 cells stably expressing the delta F508 CFTR protein can adapt to hyperosmotic conditions and accumulate cellular osmolytes.

FIG. 25 shows that 3T3 cells stably expressing the delta ΔF508 CFTR protein can adapt to hyperosmotic conditions and accumulate cellular osmolytes. 3T3 cells were gradually adapted over a period of weeks to growth in hyperosmotic media (DMEM containing an additional 250 mM NaCl and 250 mM urea). Adapted cells (3T3a) and cells maintained at isosmotic conditions (3T3) were acid extracted and the extracts were examined by HPLC to determine intracellular osmolyte accumulation. FIG. 25A shows that when cells expressing the mutant ΔF508 CFTR protein are incubated under hyperosmotic conditions (high salt) the cells begin to accumulate different osmolytes and to different levels. This effect is not unique to the cells expressing the mutant protein but also occurs in those cells expressing the wild type protein (data not shown).

FIG. 26 shows that osmotic adaptation results in a partial correction of ΔF508 CFTR processing and function In Panel A, 3T3 cells stably expressing the ΔF508 CFTR protein were osmotically adapted as described above. Both adapted and non-adapted control cells were lysed and examined by Western blot analysis to determine the processing status and content of immature (band B) and mature (band C) forms of the CFTR protein. As a positive control, cells expressing the wild type CFTR were also examined. In Panel B, chloride conductance analysis were conducted on control (cells maintained in isosmotic media) osmotically adapted cells, and cells treated for 2D with 1M glycerol. The results of these experiments are expressed as the percentage of forskolin stimulated chloride conductance as compared to cells expressing wild type CFTR.

Figure 26A:
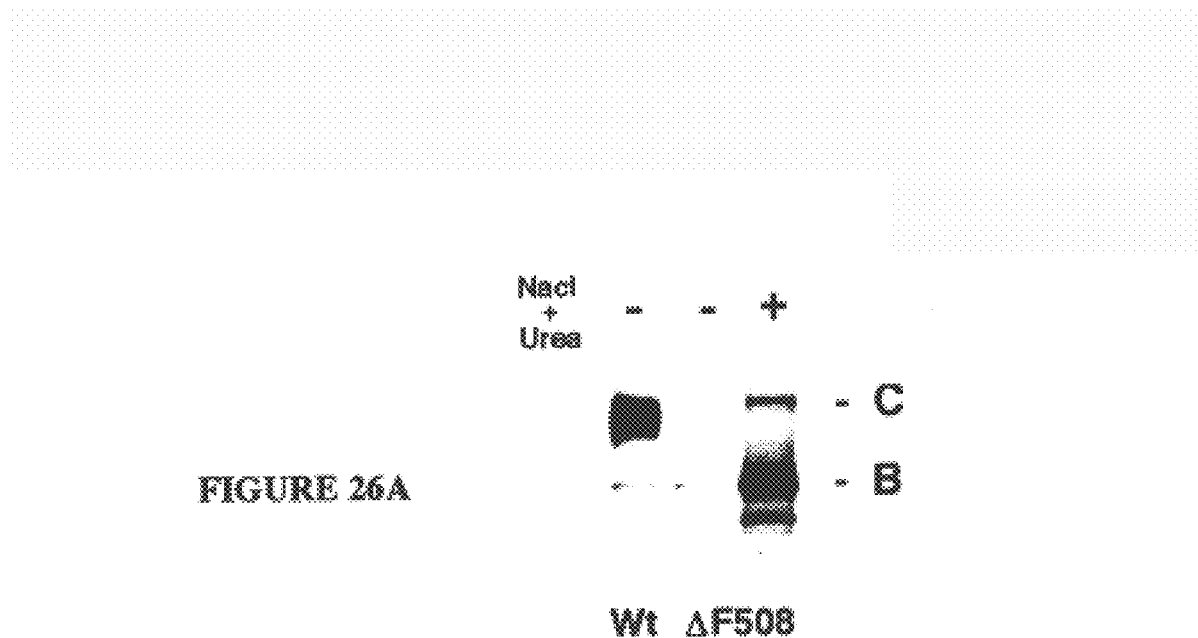
FIG. 26. Osmotic adaptation results in a partial correction of F508 CFTR processing and function.
Figure 26B:
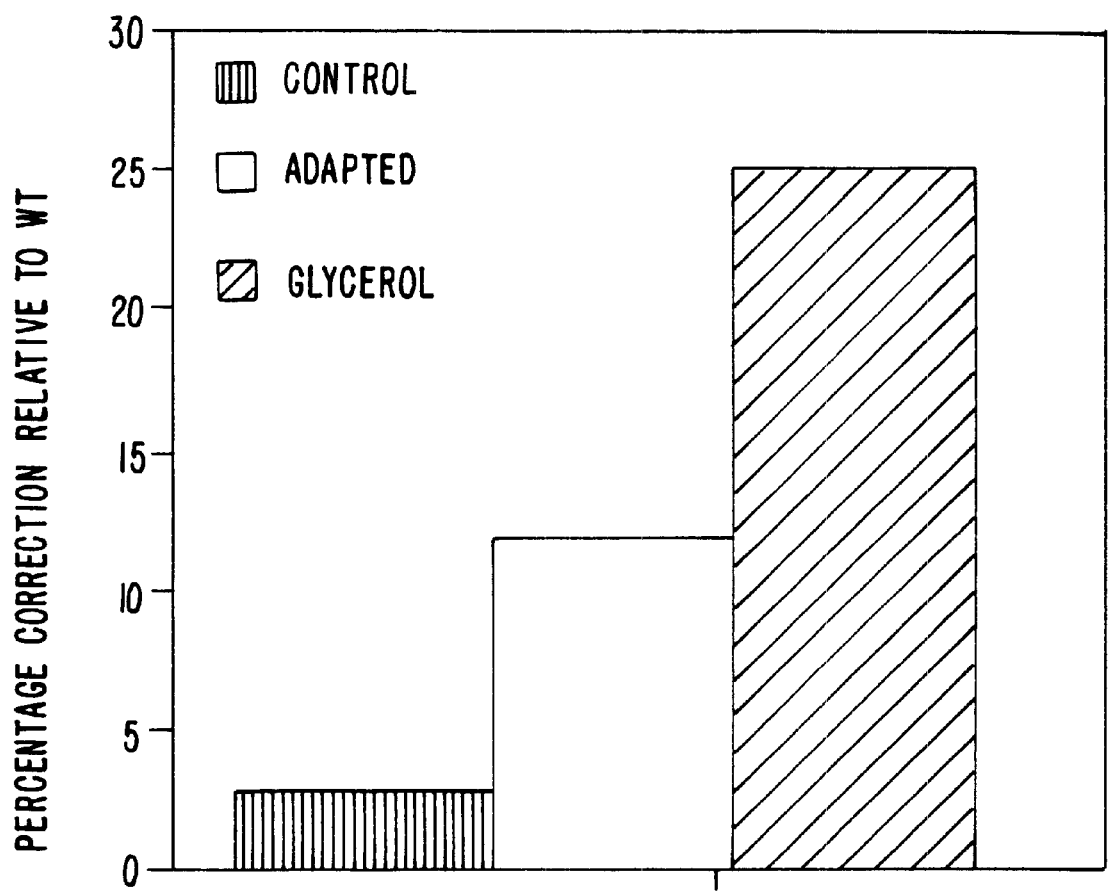

FIG. 26A shows that 3T3 cells expressing ΔF508 CFTR protein, when treated under hyperosmotic conditions as in FIG. 25A, now show some correct folding of the ΔF508 CFTR protein. Specifically, note that in the +NaCl and Urea the C band is seen (but only a fraction compared to the cells expressing the wild type protein). FIG. 26B shows that cells treated as described above in 26A now show some restoration of chloride transport (plotted again as % of that observed for wild type).

Figure 27A:
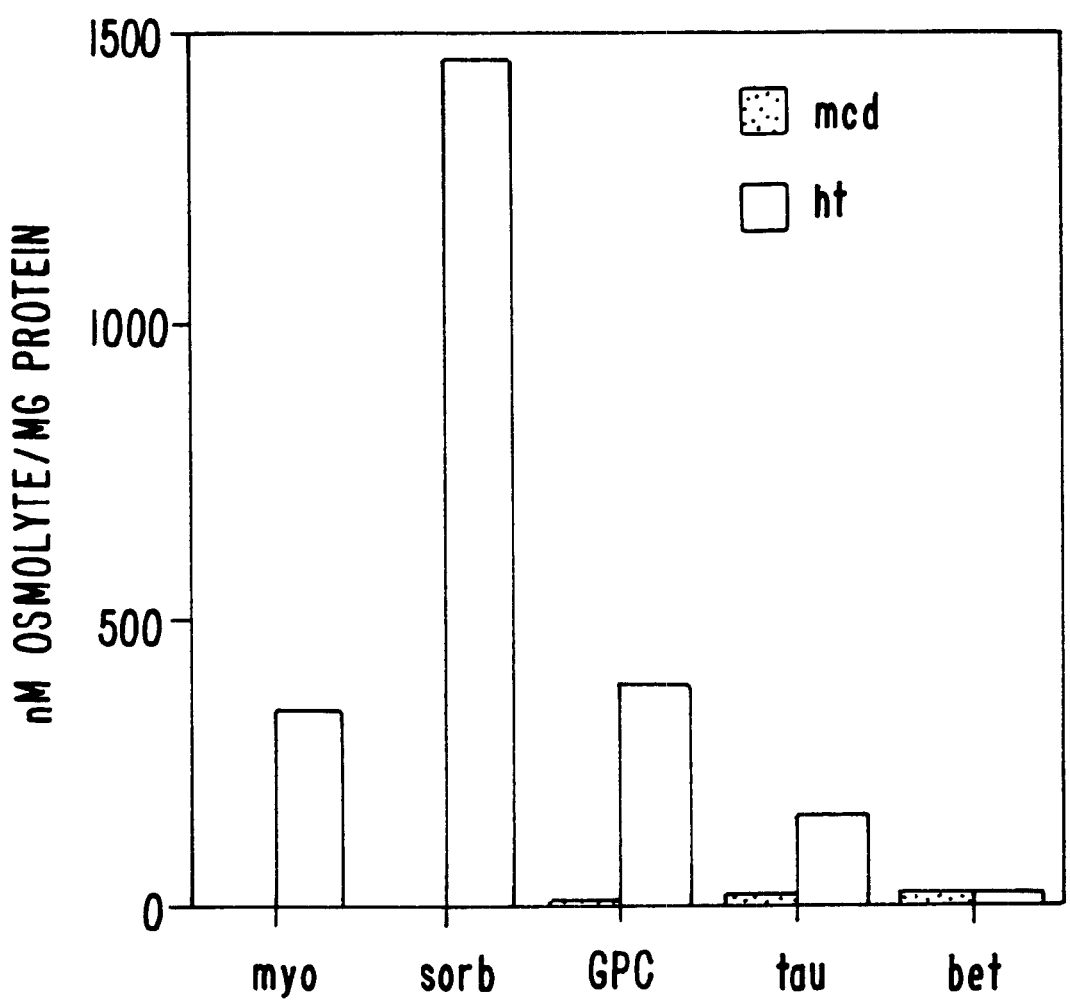
FIG. 27. Adaptation of kidney derived cells to high salt and urea conditions results in the accumulation of cellular osmolytes.
Figure 27B:
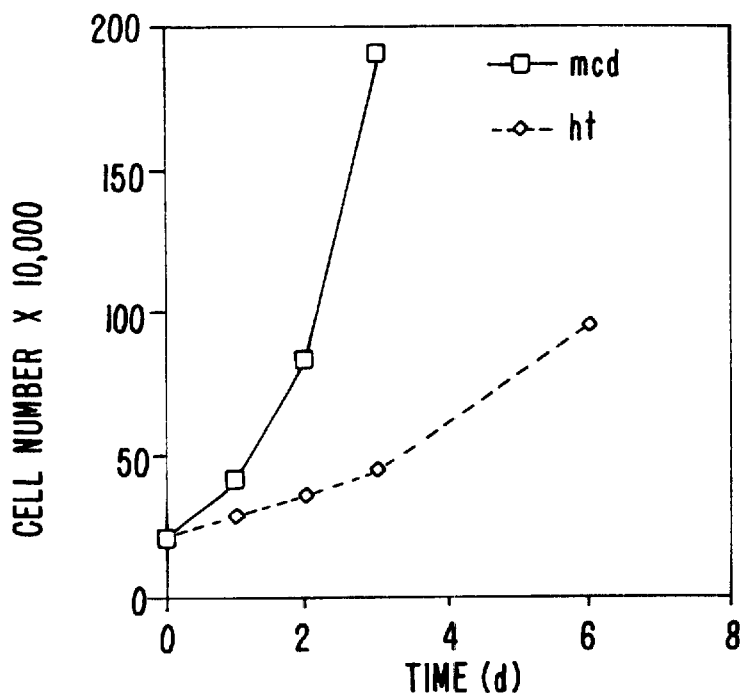
Figure 27C:
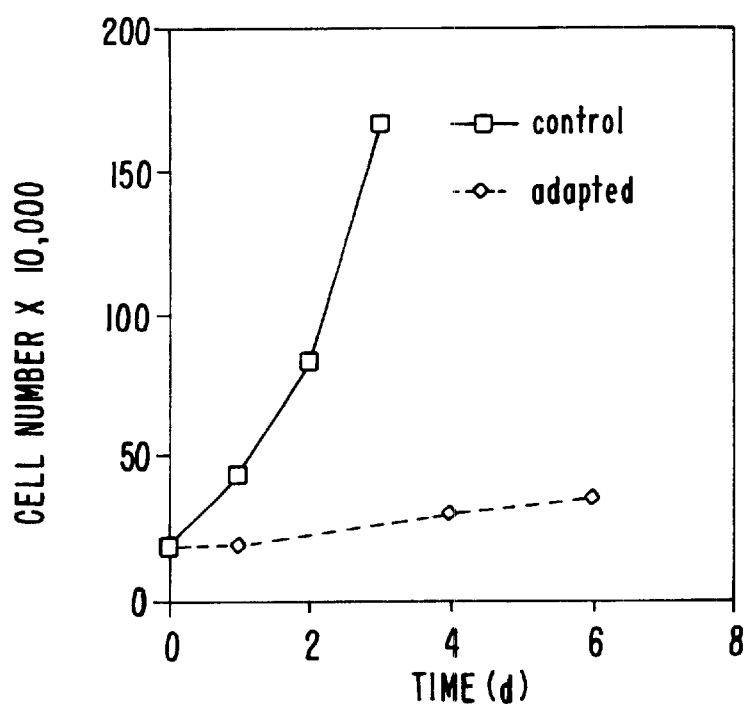

FIG. 27 shows the adaptation of kidney derived cells to high salt and urea conditions results in the accumulation of cellular osmolytes. In Panel A, mIMCD cells were gradually adapted over a period of weeks to growth in hyperosmotic media. These cells (designated Ht500) were lysed and processed as described above to determine intracellular osmolyte concentrations. In Panel B, the effects of osmotic stress on cellular growth rates were determined using mIMCD cells maintained in either isomotic (mcd) or hyperosmotic (ht) conditions. As a comparison, the growth rates of 3T3 cells and adapted 3T3 (3T3a) cells were also examined under the same conditions. Control cells maintained in isomotic media and adapted cells were plated on 60 mM dishes and counted at daily intervals. FIG. 27A shows that kidney cells subjected to high salt conditions (hyperosmotic) accumulate cellular osmolytes. Med refers to the cells grown under normal conditions (no osmotic shock) while the ht refers to the same kidney cells, but grown under high salt conditions. FIG. 27B (top panel) shows that the kidney cells exhibit slower rate of proliferation when subjected to hyperosmotic conditions. The (bottom panel) shows that 3T3 cells exhibit a significant drop in cellular proliferation when subjected to hyperosmotic conditions.

Figure 28A:
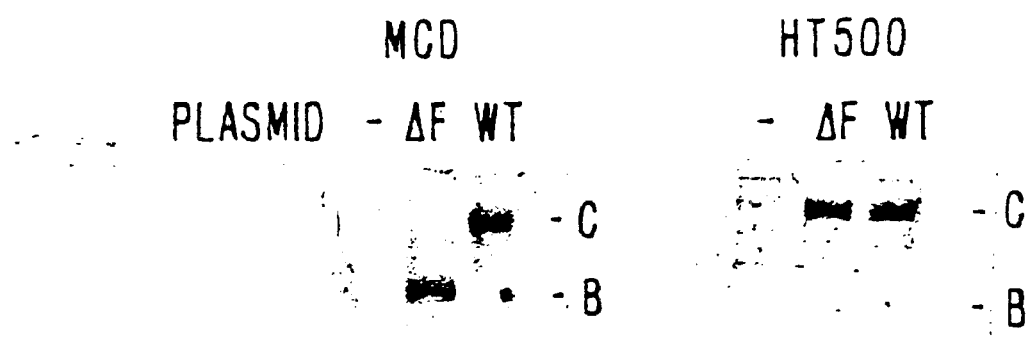
FIG. 28. Adaptation to high salt and urea conditions promotes the proper processing and function of the F508 CFTR protein.

FIG. 28 demonstrates that adaptation to high salt and urea conditions promotes the proper processing and function of the ΔF508 CFTR protein. mIMCD and Ht500 cells were transiently transfected with plasmids containing either the wild type or ΔF508 CFTR sequence. Following a 48 h recovery period, the cells were lysed and examined by Western blot analysis to determine the expression level and processing status of the CFTR protein. In Panel A, mIMCD cells and Ht500 cells that were either mock transfected, or transfected with the ΔF508 CFTR or wild type CFTR plasmid. In Panel B, chloride conductance rates of Ht500 cells that were mock transfected or transfected with the ΔF508 CFTR plasmid. In FIG. 28A, the kidney cells used above were maintained under normal conditions (MCD) or were adapted to high salt (HT500=hyperosmotic) conditions. Then the gene encoding, either the wild type or ΔF508 CFTR proteins, were transfected into the cells. Note that the ΔF508 protein expressed in the MCD cells is only the immature B band, while those cells expressing the wild type protein show the mature and functional C band. Now when adapted to high salt conditions,the cells transfected with the gene encoding ΔF508 CFTR now show the mature C band form of the protein, identical to that observed for the cells expressing the wild type protein. (This may explain why patients with the disease (ΔF508) show little or no abnormalities in the kidney. the natural high salt conditions found in the kidney may result in osmolyte accumulation and therefore correct folding of the mutant protein.

Figure 28B:
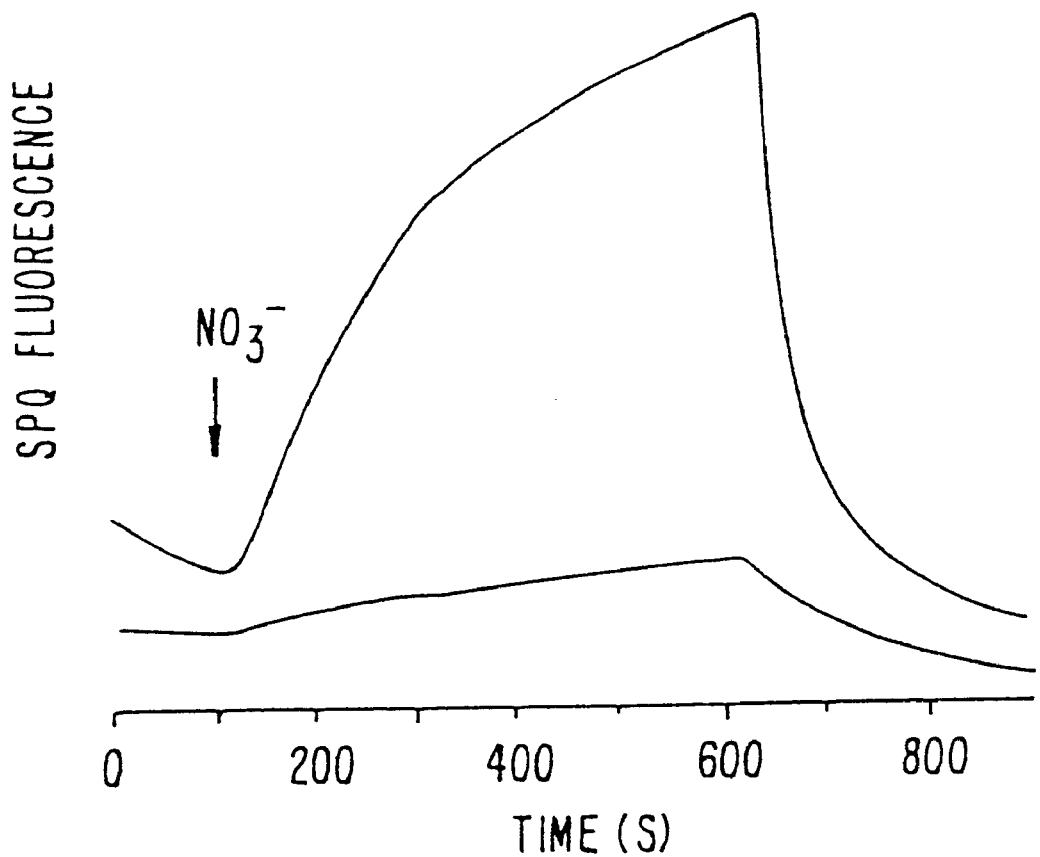

In FIG. 28B, the salt adapted kidney cells (above) expressing ΔF508 CFTR protein are able to transport chloride ions. An increase in chloride transport was observed only in the salt adapted kidney cells expressing the ΔF508 CFTR protein as compared to the mock transfected cells.

Example 2

Prions

This example illustrates that incubation of scrapie-infected mouse neuroblastoma cells with protein stabilizing agents used in Example 1 results in a significant reduction in the rate and extent of conversion of the prion protein to the infective scrapie form. See also, Tatzelt et al., 1996, *EMBO J.* 15: 6363–6373.)

Cell Culturing and Metabolic Labeling

N2a and ScN2a cells were grown in MEM Eagles medium containing 10% fetal calf serum. For steady state labeling, cells were incubated with 200 $\mu$Ci/ml [$^{35}$S]-methionine/cysteine (Amersham) for 12–15 hours in medium consisting of methionine and cysteine free DME supplemented with 5% fetal calf serum and 5% complete MEM Eagles medium. For pulse-chase experiments cells were labeled with 400 $\mu$Ci/ml [$^{35}$S]-methionine/cysteine in methionine and cysteine free DME for the time periods indicated in the figure legends.

Harvesting of the Cells and Detergent Fractionation

Cells were harvested by removing the culture medium and subsequent washing with cold phosphate buffered saline (PBS). The cells were lysed in cold (4° C.) buffer A (1% Triton X-100, and 1% sodium deoxycholate in PBS). Following scraping of the cells off the culture dish, the lysate was centrifuged at 15,000×g for 20 min. at 4° C. The supernatant was removed and adjusted to a final 1% Sarkosyl, while the pellet was solubilized in buffer A supplemented with 1% Sarkosyl (buffer B). To an equal percentage of the supernatant and pellet, protease K at the concentrations indicated in FIG. 1, was added and the reactions performed at 37° C. for 30 min. Reactions were terminated by the addition of concentrated Laemmli sample buffer (such that the final concentration of SDS was 1%) and the samples immediately heated at 100° C. for 5 minutes.

Antibodies Used

Rabbit anti-PrP antibody (R073) was raised against sodium dodecyl sulfate-polyacrylamide gel electrophoresis (SDS-PAGE)-purified Syrian hamster PrP 27–30. Serban et al., *Neurology*, 40:110–117 (1990). Mouse monoclonal anti PrP (3F4) is specific for hamster and human PrP. Kascsak et al., *J. Virol.*, 61:3688–3693 (1987). Although it does not recognize mouse PrP it does recognize the MHM2 chimeric form of PrP.

Immunoprecipitation and Analysis by SDS-PAGE

For immunoprecipitation, radiolabeled cells were lysed and fractionated as described above. The supernatants and pellets were adjusted to 1% Sarkosyl, and then incubated in the presence of immobilized Protein A for 30 min. After removal of the Protein A-sepharose, the primary antibody was added and the samples incubated for 1.5 hrs at 4° C. The antibody-antigen complexes were captured via the addition of immobilized Protein A and then washed 4 times with buffer B. The immunoprecipitated proteins were released from the Protein A-sepharose by the addition of Laemmli sample buffer containing 1% SDS and heating at 100° C. for 5 min.

Proteins present within whole cell lysates or detergent fractionated cell lysates, as well as immunoprecipitated proteins, were analyzed by SDS-PAGE. Gels were impregnated with Amplify (NEN DuPont) and exposed to film at −70° C.

Western Blotting

Following SDS-PAGE, proteins were transferred to nitrocellulose. The filters were blocked by incubation in PBS containing 5% nonfat dry milk and 0.1% Tween-20 for 1 hr at room temperature. The blots were incubated with primary antibody diluted in PBS containing 0.1% Tween-20 (PBS/Tween) for 12 h at 4° C. After extensive washing with PBS/Tween, the blots were incubated with horseradish peroxidase conjugated secondary antibody (Amersham) for 30 min. at room temperature. Following extensive washing with PBS/Tween, the blots were developed by using an enhanced chemiluminescence substrate (Amersham).

Preparation of Protein Extracts from Mice Brains and Inoculation of Cell Culture Brain homogenates (10% w/v) were prepared in ice cold PBS containing 1% Triton X-100 and centrifuged at 3000×g for 30 min. The pellet was dissolved in buffer A and the centrifugation step was repeated. Proteins present within the supernatant then were precipitated with cold methanol, resuspended in PBS containing 10% glycerol, quick frozen in liquid nitrogen and stored at −80° C. For inoculation experiments 50 $\mu$l MKM2 extract in 1 ml medium was added to a 25 cm$^2$ dish of 30–50% confluent N2a or ScN2a cells. After 12 hours the cells were washed twice and analyzed with the detergent assay after various time points as indicated in the figure legends.

Phospholipase Experiments

Cells were washed twice and subsequently incubated in serum free medium with 5 U/ml Phosphatidylinositol Phospholipase C (PIPLC, Boehringer Mannheim) for 4 hrs at 37° C. The cells were extensively washed with PBS, lysed with cold buffer A, and fractionated into a supernatant and pellet as described above. PrP present with the detergent soluble and insoluble fractions was analyzed by Western blotting.

Example 2A

Differential Detergent Solubility of PrP$^C$ and PrP$^{Sc}$ in Scrapie-Infected N2A Cells In ScN2a cells, approximately 10% of PrP$^C$ is converted into infectious PrP$^{Sc}$ as assayed by its relative resistance to protease K digestion and by bioassays. Borchelt, *J. Cell Biol.*, 110: 743–752 (1990). Owing to the potential variability of results using protease digestion assays, along with both the high costs and long times needed for scrapie bioassays, we developed a new assay for monitoring the extent of PrP$^{Sc}$ formation in ScN2a cells. Specifically, we wanted an assay which, unlike the protease digestion approach, would also allow for the determination of the relative amounts of PrP$^C$.

Figure 5A:
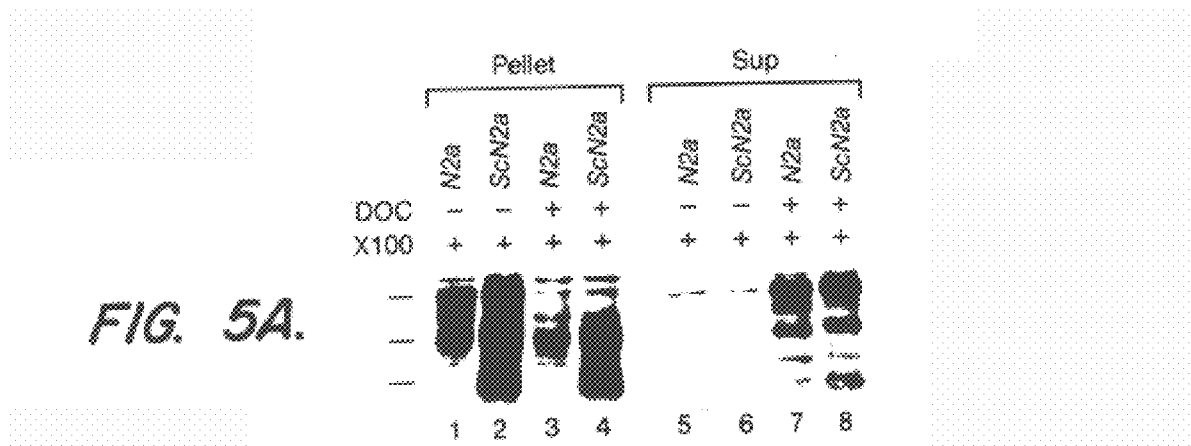
FIG. 5. Differential detergent solubility assay for quantifying the relative proportions of $PrP^C$ and $PrP^{Sc}$.

Many glycolipidated proteins are relatively insoluble in cold (i.e., about 4° C.) buffers containing 1% Triton X-100 or Triton X-114. Hooper and Bashir, *Biochem J.*, 280:745–751 (1991). This is also true for PrP$^C$, as illustrated in FIG. 5A: N2a and ScN2a cells were solubilized in cold (i.e., about 4° C.) phosphate buffered saline (PBS) containing either 1% Triton X-100 or 1% Triton X-100 plus 1% sodium deoxycholate (DOC). The cell lysates were incubated for 10 min on ice and then centrifuged at 15,000×g for 20 min. The supernatant was removed and adjusted to a final Sarkosyl concentration of 1%. The pellet was resuspended in PBS containing 1% Triton X-100, 1% DOC and 1% Sarkosyl. An equal percentage of both the pellet (Pellet, lanes 1–4) and supernatant (Sup, lanes 5–8) fractions were analyzed by Western blotting using the α-PrP antibody R073.

Analysis of the resultant supernatant and pellet revealed that the majority of PrP$^C$, be it from the N2a or ScN2a cells, partitioned into the detergent insoluble fraction when the cells were lysed in cold buffer containing 1% Triton X-100.

If, however, the cells were lysed at about 4° C. in PBS containing both 1% Triton X-100 and 1% sodium deoxycholate (DOC), markedly different results were obtained. Now the vast majority of PrP present within the N2a cells was observed to fractionate within the detergent soluble fraction. Relatively little PrP was found within the detergent insoluble pellet. In contrast, PrP from the ScN2a cells was observed to partition into both the detergent soluble and insoluble fractions. The faster migrating forms of PrP present were relatively enriched within the detergent insoluble fraction obtained from the ScN2a cells.

Figure 5B:
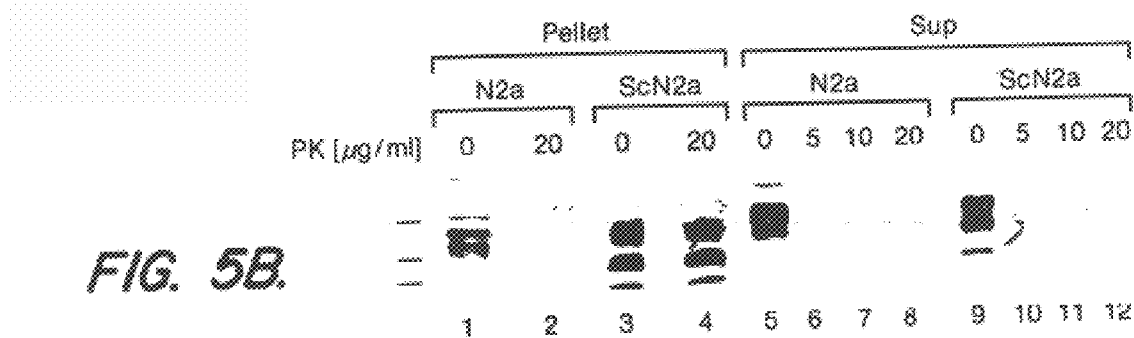

To determine whether these faster migrating forms of PrP which were relatively enriched within the detergent insoluble fraction of the ScN2a cells might represent the scrapie isoform, protease digestion of the material present within both fractions was performed (FIG. 5B). N2a and ScN2a cells were lysed in cold buffer A (PBS containing 1% Triton X-100 and 1% DOC) and centrifuged exactly as described above. The supernatant was removed and the pellet resuspended in buffer A containing 1% Sarkosyl. To the supernatant and pellet was added protease K (concentrations as indicated in the fig.). Following a 30 min. digestion at 37° C., the reactions were terminated via the addition of concentrated Laemmli sample buffer and immediate heating at 100° C. for 5 min. The samples then were examined for PrP via Western blotting using the R073 antibody. Varying amounts of PK were used to examine the supernatant (Sup) derived from either the N2a (lanes 1–4) and ScN2a cells (lanes 5–8), while only a single concentration of PK was used to examine the material present within the pellet (Pellet) of the N2a (lanes 9, 10) and ScN2a (lanes 11, 12) cells.

In ScN2a cells, the majority of PrP present within the detergent soluble fraction was degraded by added protease K while the majority of PrP present within the detergent insoluble pellet was relatively unaffected by the protease K treatment. In N2a cells, the PrP present in either the detergent soluble or insoluble fraction was completely degraded by added protease.

Owing to its relative resistance to protease K, we conclude that the detergent insoluble form of PrP present within the ScN2a cells represents primarily $PrP^{Sc}$. These results indicate that $PrP^{Sc}$, in contrast to $PrP^{C}$, preferentially partitions into the detergent insoluble fraction when the cells are lysed in a cold (about 4° C.) physiological buffer containing both 1% Triton X-100 and 1% sodium deoxycholate.

Figure 5C:
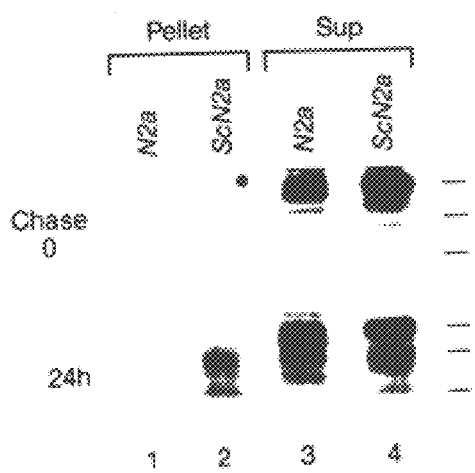

Using this detergent solubility assay, we examined the conversion of newly synthesized $PrP^{C}$ into $PrP^{Sc}$ in the ScN2a cells (FIG. 5C). N2A (lanes 1,3) and ScN2A cells (lanes 2,4) were labeled with [$^{35}$S]-methionine for 4 hrs. One plate of the radiolabeled cells was harvested immediately (chase 0). To the other radiolabeled cells, the medium was removed and the cells washed with and further incubated in fresh culture medium for 20 hrs (chase 24 h). Both the pulsed and pulsed-chased radiolabeled cells were harvested in buffer A, and the lysates centrifuged at 15,000×g for 20 min. PrP was immunoprecipitated from either the pellet (Pellet, lanes 1,2) or the supernatant (Sup, lanes 3,4) as described in the material and methods. The resultant immunoprecipitates were analyzed via SDS-PAGE and fluorography. Note that the exposure time of the films was 14 hrs for the pulse-labeled material, and 4 days for the pulsed and chased material. As a control in these experiments, the pulse and pulse-chase radiolabeling similarly was performed with the N2a cells. All of the radiolabeled cells then were lysed in PBS containing 1% Triton X-100 and 1% DOC and subjected to centrifugation as described above. An equal percentage of the resultant supernatants and pellets were analyzed for their distribution of PrP via immunoprecipitation.

In both the 4 hr pulse-labeled N2a and ScN2a cells, all of the newly synthesized PrP was found within the detergent soluble fraction. Similarly, in the N2a cells pulse-labeled and then chased for 20 yrs. the portion of radiolabeled PrP still remaining was found exclusively within the detergent soluble fraction. In contrast, the remaining radiolabeled PrP produced in the ScN2a cells after the 20 hr. chase period was found to partition into both the detergent soluble and insoluble fractions. Again note that the forms of PrP present within the detergent insoluble fraction of the ScN2a cells migrated with a faster mobility relative to that observed for PrP present within the detergent soluble fraction. Results from several experiments indicated that approximately 10–20% of the PrP synthesized in the ScN2a cells was converted into the detergent insoluble $PrP^{Sc}$-like isoform over the course of the 20 hr. chase period.

Example 2B

Glycerol Interferes with the Conversion of $PrP^{C}$ to $PrP^{Sc}$ in ScN2a Cells Using the simple, rapid assay for monitoring the in vivo conversion of $PrP^{C}$ to $PrP^{Sc}$ described in Example 2A, we set out to identify agents that interfere with the conversion event. The following demonstrates that glycerol is one such agent.

Figure 6A:
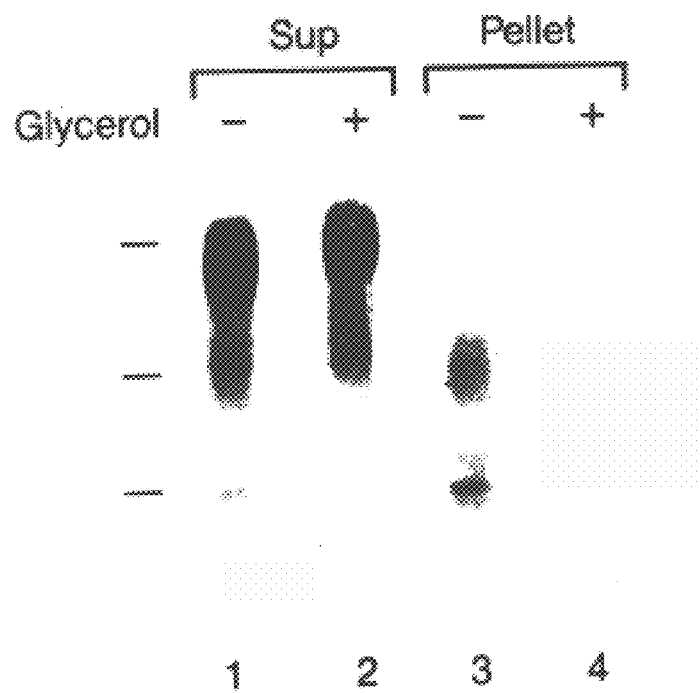
FIG. 6. Demonstration that glycerol treatment of ScN2a cells results in reduced levels of $prP^{Sc}$.

A pulse-chase experiment similar to the one shown in FIG. 5 above was performed with the ScN2a cells, except that the cells first were incubated culture medium either lacking or supplemented with 1 M glycerol for 18 hrs. The cells were labeled with [$^{35}$S]-methionine for 4 hrs, either in the presence or absence of glycerol. The medium containing the radiolabel was removed, and the cells then further incubated in complete medium (plus or minus glycerol) for an additional 20 hrs. The cells were harvested in Buffer A and fractionated into a supernatant and pellet, and analyzed for their distribution of radiolabeled PrP using the detergent solubility assay (FIG. 6A). The distribution of PrP within each fraction was determined via immunoprecipitation using the R073 antibody.

Shown in FIG. 6A is a fluorograph of the gel analyzing the resultant PrP immunoprecipitates. Again, in the absence of glycerol, in the ScN2a cells the $PrP^{C}$ was converted into $PrP^{Sc}$, as evidenced by the presence of the radiolabeled protein within the detergent insoluble fraction. In contrast, relatively little of the radiolabeled PrP synthesized in the glycerol treated ScN2a cells was found within the detergent insoluble fraction. Instead, almost all of the remaining radiolabeled PrP now was observed within the detergent soluble fraction.

Figure 6B:
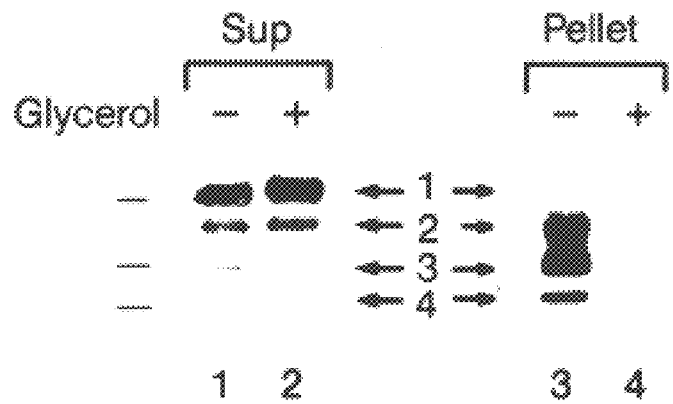

We next incubated ScN2a cells in either the absence or presence of 1 M glycerol for a period of 3 days, and then analyzed the cells for their distribution of detergent soluble and insoluble PrP via Western blotting (FIG. 6B). In those cells maintained in the presence of glycerol for 3 days, little or no detergent insoluble PrP was observed.

Figure 7A:
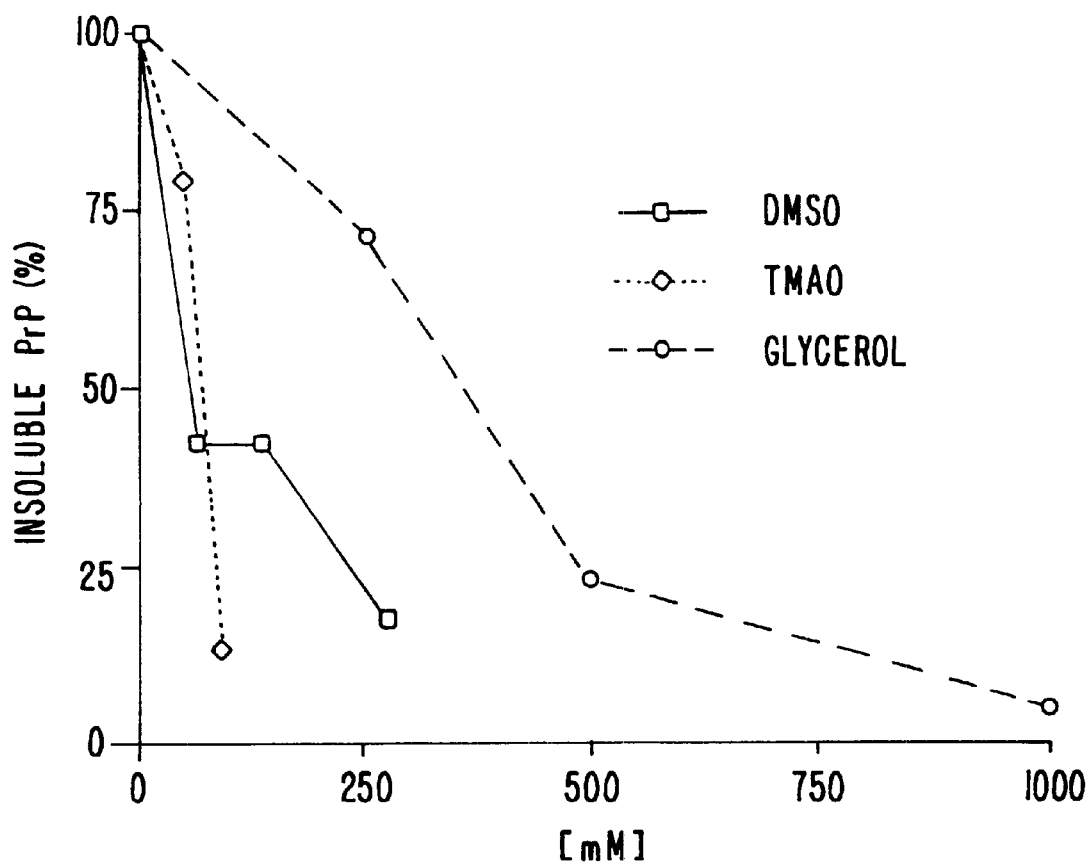
FIG. 7. Effect of different concentrations of glycerol, TMAO and DMSO on the conversion of $PrP^C$ to $PrP^{Sc}$: demonstrating that glycerol, DMSO and TMAO interfere with the accumulation of insoluble $PrP^{Sc}$ in both a dose dependent and time dependent manner.

Both the concentration of glycerol, as well as the duration of glycerol treatment needed to interfere with the conversion of $PrP^{C}$ to $PrP^{Sc}$ was examined (FIG. 7). ScN2a were incubated for 3 days in medium containing differing concentrations (0, 250, 500, 750 and 1,000 mM) of glycerol. As a control, ScN2a cells, plated at the same density, were incubated for 3 days in culture medium not containing any additional components. The cells were harvested in cold buffer A and fractionated into a supernatant and pellet exactly as described earlier. The amount of detergent insoluble PrP was determined by comparative Western blotting using the R073 antibody. Results are expressed relative to the amount of PrP present within the detergent insoluble fraction of the ScN2a cells not exposed to glycerol (i.e., 100%). All values for insoluble $PrP^{Sc}$ were normalized to the expression of soluble $PrP^C$. Shown are representative data from multiple experiments. (FIG. 7A, round symbols). While 1 M glycerol appeared to be the most effective, a significant reduction in the conversation of $PrP^C$ to $PrP^{Sc}$ also was observed at glycerol concentrations between 0.25–0.5 M.

Figure 7B:
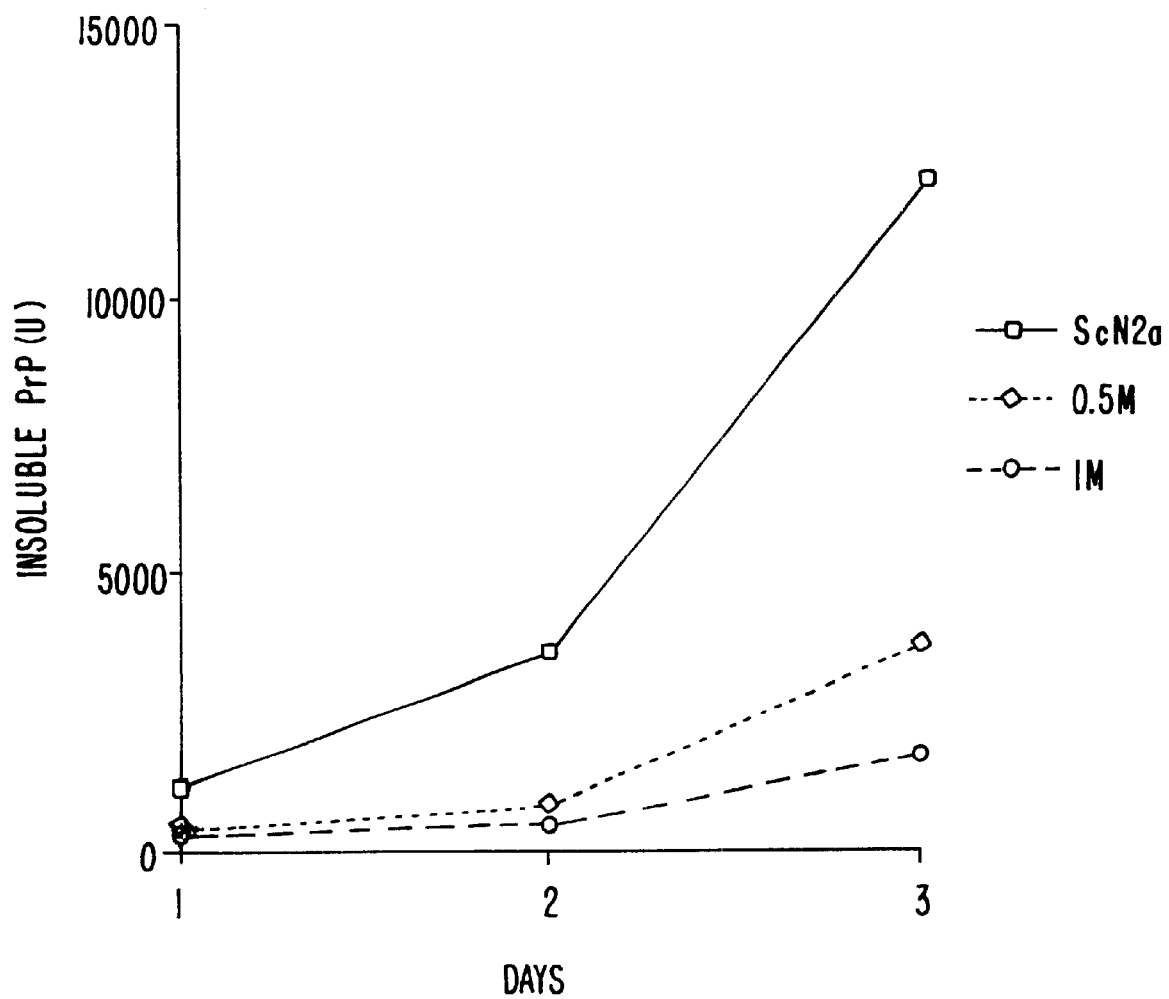

Analysis of the optimal time of glycerol treatment to reduce the extent of detergent insoluble PrP in the ScN2a cells is presented in FIG. 7B. Here, the ScN2a cells were plated at approximately 10–20% confluency and then incubated in the presence or absence of two different concentrations of glycerol over a period of 1 to 3 days. After only 1 day of treatment with 0.5 M or 1 M glycerol, a vast reduction in the amount of detergent insoluble PrP was observed. In the case of those cells incubated with 0.5 M glycerol, by days 2 and 3 the relative levels of detergent insoluble PrP was found to be slightly on the increase. In-contrast, the overall levels of detergent insoluble PrP observed within the ScN2a cells incubated with 1 M glycerol changed only little over the 3 day incubation period.

A number of control experiments were performed in order to confirm that glycerol was in fact interfering with the conversion of $PrP^C$ to $PrP^{Sc}$, rather than simply affecting some aspect of $PrP^C$ biogenesis. First, via metabolic labeling of the ScN2a cells in the presence and absence of glycerol, no significant differences were observed with respect to either the rate, or overall extent of $PrP^C$ synthesis.

Next, we examined whether $PrP^C$ which is synthesized in the presence of glycerol still moves to the plasma membrane and can be released from the cells via treatment with phospholipase. Both N2a and ScN2a cells were cultured in either the absence or presence of glycerol for 24 hrs. The cells then were either mock incubated, or incubated with phospholipase C (PIPLC) (5 U/ml) for 4 hrs. at 37° C. Following their extensive washing with PBS, the cells were collected and analyzed by the detergent solubility assay and Western blotting (FIG. 8).

Figure 8:
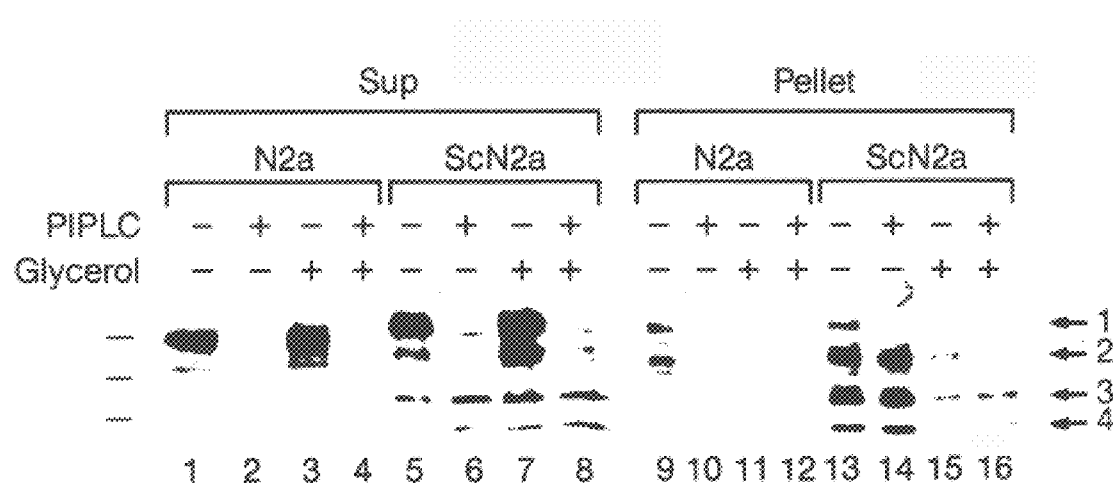
FIG. 8. Demonstration that glycerol treatment does not affect the cell surface localization of $PrP^C$.

In both the N2a and ScN2a cells incubated in the absence of glycerol, phospholipase treatment resulted in a significant reduction, or even the complete absence of detergent soluble PrP (FIG. 8, lanes 2 and 6, respectively). This observation, consistent with the results of other studies, indicates that the majority of detergent soluble PrP likely is derived from that portion of $PrP^C$ which is present at the plasma membrane. Phospholipase treatment of both the N2a and ScN2a cells grown in the presence of glycerol similarly resulted in the disappearance of detergent soluble PrP (FIG. 8, lanes 4 and 8, respectively). With respect to the detergent insoluble PrP, again the ScN2a cells incubated in the presence of glycerol showed a marked reduction in the overall levels of insoluble PrP as compared to the non-glycerol treated cells (FIG. 8, lanes 15 and 13, respectively). Here treatment of the cells with phospholipase had little or no effect on the amounts of detergent insoluble PrP, be it in those cells incubated in the presence or absence of glycerol. Finally, it is interesting to note that the low levels of detergent insoluble PrP observed in the N2a cells (FIG. 8, lane 9 and also see FIG. 5B, lane 10) no longer was observed when the cells had been incubated in the presence of glycerol (FIG. 8, lane 11) From these and a number of other control experiments, we conclude that the addition of glycerol to the ScN2a cells does not significantly affect either the overall rate or the absolute amounts of $PrP^C$ which is synthesized, nor the movement of the newly synthesized protein to the plasma membrane. Rather, we suspect that glycerol somehow is affecting directly the conversion process by which $PrP^C$ is driven into $PrP^{Sc}$.

Figure 9A:
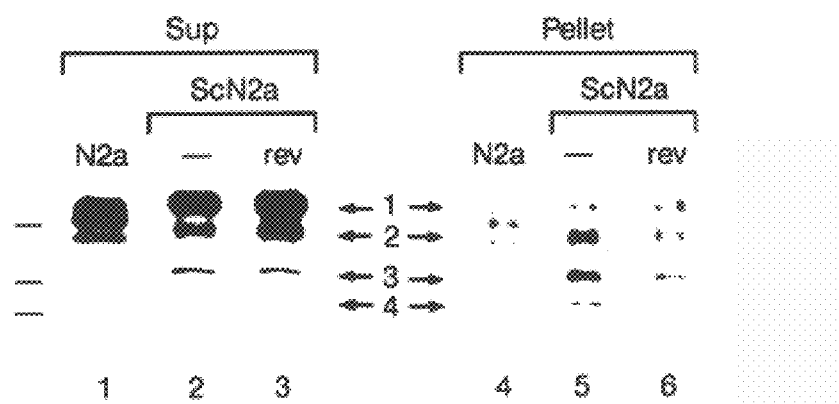
FIG. 9. Demonstration that the effect of glycerol on the interference of $PrP^C$ to $PrP^{Sc}$ conversion is reversible.

We next examined whether incubation of the cells in glycerol for a period of 3 days might effectively "cure" the ScN2a cells of their ability to carry out the conversion process. Following 3 days of incubation in the presence of 1 M glycerol, the culture medium was removed, the cells extensively washed with fresh culture medium, and then further incubated in the absence of glycerol for 5 days (glycerol treated and reversed). The cells were harvested and analyzed via the detergent solubility assay and subsequent Western blotting (FIG. 9A). As was shown in FIG. 6, we were unable to detect significant amounts of detergent insoluble PrP in the ScN2a cells incubated for 3 days in the presence of 1 M glycerol. However, when the 3 day glycerol treated ScN2a cells were subsequently incubated in the absence of glycerol for a period of 5 days, detergent insoluble PrP again was observed (FIG. 9A, lane 6). Note however, that relative to those ScN2a cells which never had been exposed to glycerol (FIG. 9A, lane 5), the amounts of detergent insoluble PrP still was markedly less in the glycerol treated and reversed ScN2a cells.

Figure 9B:
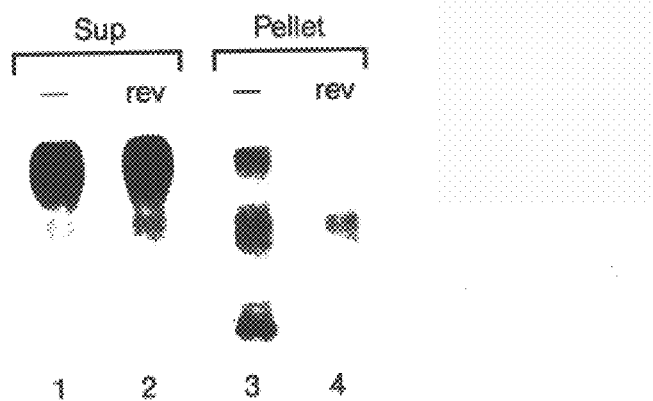
Figure 9C:
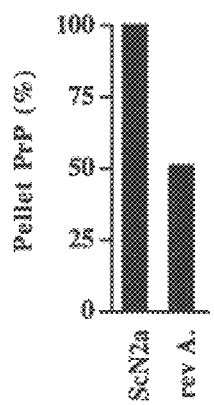

Similar results were observed when the experiment was performed using metabolic pulse-chase labeling (FIG. 9B). Utilizing a pulse-chase metabolic labeling protocol similar to that used earlier (i.e, the experiment presented in FIG. 6) the ScN2a cells first treated with glycerol for 3 days, and then incubated in the absence of the chemical for 5 days now had regained their ability to convert $PrP^C$ into $PrP^{Sc}$. Note that relative to the control untreated ScN2a cells, the glycerol treated and reversed cells again exhibited a marked reduction in the overall extent of $PrP^C$ to $PrP^{Sc}$ conversion (FIG. 9B).

Example 2C

Figure 10A:
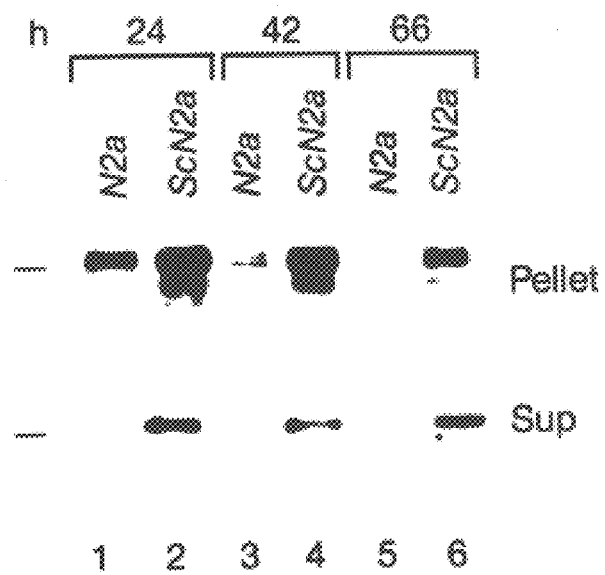
FIG. 10. Demonstration that detergent soluble $PrP^C$ added to ScN2a cells is converted to a detergent insoluble form in the absence, but not the presence of glycerol.

Glycerol Treatment Interferes with the Conversion of Exogenously Added $PrP^C$ to $PrP^{Sc}$ in ScN2a Cells We next examined whether glycerol treatment of the ScN2a cells also might interfere with the conversion of exogenously added $PrP^C$ into $PrP^{Sc}$. Brain extracts enriched in $PrP^C$ were prepared from transgenic mice expressing a chimeric mouse-hamster form of $PrP^C$ (MHM2, for Mouse-Syrian Hamster-Mouse chimera). Previous work has established that mice expressing this chimeric form of $PrP^C$ are susceptible to added mouse scrapie prions, and develop scrapie disease. Scott et al., Cell 73:979–988 (1993). In the first experiment, the chimeric $PrP^C$ was added to the culture medium of both N2a and ScN2a cells incubated in the absence of glycerol. After 12 hrs of incubation, the cells were washed extensively with fresh culture medium to remove any remaining exogenous $PrP^C$ and the cells then further incubated for an additional 24, 42, or 66 hrs. At each time point the cells were collected and analyzed for their distribution of the exogenously added PrP via the detergent solubility assay and Western blotting (FIG. 10A). To follow the distribution of only the exogenously added MHM2 form of PrP, we utilized the 3F4 monoclonal antibody which is specific for the Syrian hamster form of PrP, and does not cross-react with mouse PrP. Kascsak et al., J. Virol., 61:3688–3693 (1987).

After 24 hrs of incubation both the N2a and ScN2a cells had taken up the exogenously added MHM2 $PrP^C$. Via the detergent solubility assay, the majority of the chimeric $PrP^C$ was present within the detergent insoluble fraction in both cell types. A portion of the chimeric PrP also was found within the detergent soluble fraction, but only in the ScN2a cells (FIG. 10a).

In the N2a cells the relative amounts of chimeric PrP continued to decline over time and by 66 hrs 3F4 immunoreactive material no longer was observed. In contrast, a significant amount of the chimeric PrP was still present within the ScN2a cells incubated for an additional 42 or 66 hrs after their inoculation with the MHM2 PrP$^C$ (FIG. 10a). While the majority of the protein still was observed within the detergent insoluble fraction, a portion of the protein also was found within the detergent soluble fraction. We conclude that exogenously added PrP$^C$ can be taken up by both the N2a and ScN2a cells growing in culture, but that the fate of the internalized protein is somewhat different. Specifically, only in those cells already propagating the conversion of endogenously synthesized PrP$^C$ to PrP$^{Sc}$ (i.e., the ScN2a cells) was the exogenously added PrP$^C$ converted into a form which appeared similar to that of PrP$^{Sc}$.

Figure 10B:
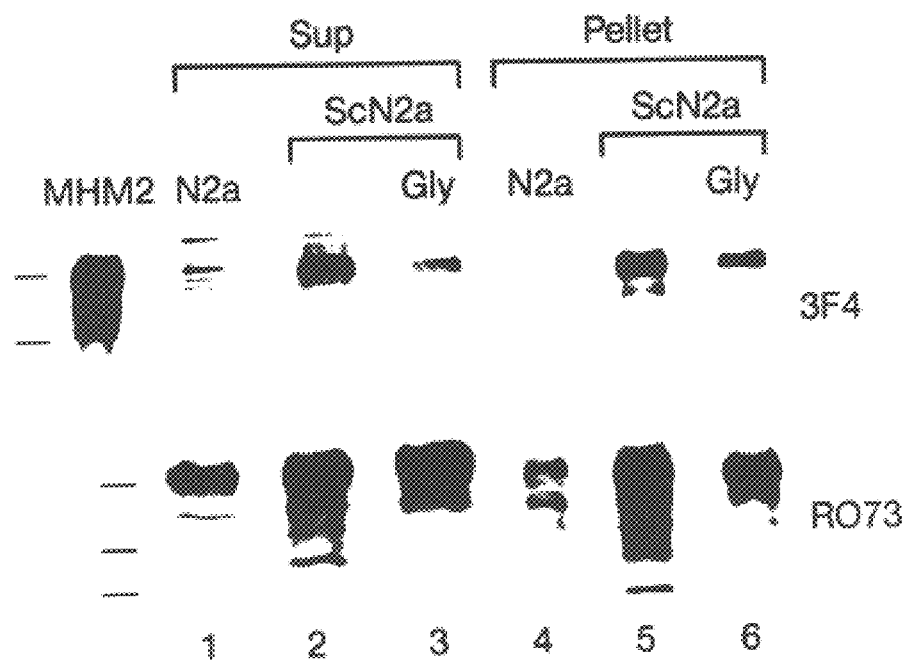

The effects of glycerol treatment on the ability of the ScN2a cells to convert the added MHM2 PrP$^C$ into a detergent insoluble form was examined (FIG. 10B). N2a (lanes 1,4), ScN2a (lanes 2,5), and ScN2a cells cultured in the presence of 1 M glycerol for 24 hrs (gly, lanes 3,6), were incubated with brain extracts prepared from MHM2-expressing transgenic mice. After 40 hrs of incubation the culture medium was removed, the cells extensively washed with PBS, and then harvested. Following fractionation of the cell lysates the distribution of detergent soluble (Sup) and detergent insoluble (Pellet,) MHM2 PrP was determined via Western blotting using the 3F4 antibody. In addition duplicate blots were prepared and probed with the R073 antibody which recognizes both MHM2 PrP as well as endogenous mouse PrP (FIG. 10B).

Similar to our earlier results, the ScN2a cells incubated in the presence of glycerol exhibited significantly less detergent insoluble endogenous PrP relative to that observed for the cells incubated in the absence of glycerol. In the case of the added MHM2 PrP$^C$, glycerol treatment also appeared to reduce the levels of the MHM2 protein in both the detergent soluble and insoluble fractions as compared to control, untreated ScN2a cells. Thus, similar to the situation with endogenously synthesized PrP, glycerol treatment appeared to effectively reduce the ability of the ScN2a cells to convert exogenously added PrP$^C$ into a form characteristic of PrP$^{Sc}$.

Example 2D

DMSO Interferes with the Conversion of PrP$^C$ to PrP$^{Sc}$ in ScN2a Cells

Using the methods discussed in Examples 2A and especially 2B, we demonstrated that DMSO was also very effective in reducing the extent of detergent insoluble PrP. 100 mM DMSO effectively reduced the amount of detergent insoluble PrP by over 50% (FIG. 7A). At 200 mM and higher, DMSO appeared to adversely affect the morphology and growth rates of the cells.

Example 2E

TMAO Interferes with the Conversion of PrP$^C$ to PrP$^{Sc}$ in ScN2a Cells

Using the methods discussed in Examples 2A and 2B, we demonstrated that TMAO also was very effective in reducing the extent of detergent insoluble PrP. 100 mM TMAO effectively reduced the amount of detergent insoluble PrP by over 50% (FIG. 7A). At 200 mM and higher, TMAO appeared to adversely affect the morphology and growth rates of the cells.

Example 3

Correction of p53 Mutants with Chemical Chaperones

A1–5 cells (a generous gift from A. Levine), a cell line expressing a temperature sensitive (ts) mutant p53 protein produced by transfection of primary rat fibroblasts with a p53 gene containing a missense mutation (ala to val at amino acid 135) (Finlay, C. A., et al., 1988, *Mol. Cell. Biol.* 8:531–539), were used to study the effects of protein stabilizing agents on p53. As was shown previously, this mutation results in a temperature sensitive protein folding defect. Michalovitz, D., et al., 1990, *Cell* 62:671–680; Martinez, J., et al., 1991, *Genes Dev.* 5:151–159; Gannon, J. V. et al., 1991, *Nature* 349:802–806.

Effects of Chemical Treatments on Cell Growth

A1–5 cells were plated in 60 mm dishes at an initial concentration of $5 \times 10^4$ cells/plate. After allowing them to attach at 37° C. for 16 h, the cells were shifted to the appropriate temperature in the presence or absence of the various protein stabilizing agents. A few plates of the cells were collected at the time of chemical addition and cell number determined using a hemocytometer. Thereafter, the cells were counted at daily intervals. All time points were examined in duplicate with the values given representing the mean for replicate counts.

Chemical Treatments

Various concentrations of protein stabilizing agents were added to DMEM supplemented with 10% fetal bovine serum. For $D_2O$ experiments, powdered DMEM was reconstituted using 100% $D_2O$ (Sigma Chemical Co.) and supplemented with 10% fetal bovine serum. For each experiment, the culture medium was removed and replaced with fresh medium containing the chemical of interest. For recovery experiments (e.g., FIG. 14) cells were incubated with the various chemicals for 2 days, the medium then removed, and the cells washed with and further incubated in normal growth medium not containing the particular protein stabilizing agent.

Western Blotting

Following the particular experimental treatment, cells were lysed in Laemmli sample buffer and heated at 100° C. for 5 min. Lysates were clarified and the proteins separated by SDS-PAGE. The resolved proteins were transferred to nitrocellulose and subsequently immunoblotted using the mouse monoclonal anti p53 antibody, 421 (Oncogene Science) or the hsp73/hsp 72 specific antibody, N27 (StressGen Biotechnologies).

A1–5 cells were grown on coverslips and incubated at either 32.5° C. or 39.5° C. for 2 days. The intracellular distribution of p53 was determined by indirect immunofluorescence using a monoclonal antibody which recognizes both the wild type and mutant forms of p53 (PAb 421). Shown in panels A & B are the cells maintained at 39.5° C., and in panels C & D the cells incubated at 32.5° C. Panels A & C are the phase contrast photographs, and panels B and D are the corresponding immunofluorescence photographs.

At temperatures around 32.5° C. (or less) the p53 protein adopts a wild type conformation and localizes within the cell nucleus (FIG. 11D). In contrast, at temperatures of 39.5° C. (or greater) the p53 protein fails to fold properly and does not accumulate within the nucleus. Instead, the vast majority of the mutant protein is found predominantly within the cytoplasm (FIG. 11B).

For indirect immunofluorescence, cells were grown on glass coverslips. Following the particular experimental treatment (described in the figure legend), cells were fixed with 100% methanol and then subsequently rehydrated in PBS. The intracellular localization of p53 was determined by incubation of the fixed cells with the antibody 421 (Oncogene Science) which recognizes both the mutant and wild type forms of p53. Primary antibody was visualized by subsequent staining with a rhodamine conjugated goat anti-mouse antibody. All antibodies were diluted in 5 mg/ml BSA in PBS.

We examined whether treatment of the A1–5 cells with different protein stabilizing agents would correct the temperature sensitive protein folding defect of mutant p53. Three different reagents were examined: the carbohydrate (or polyol) glycerol; a methylamine, trimethylamine N-oxide; and finally, deuterated water ($D_2O$). Cells were plated in normal culture medium and then incubated at 39.5° C. where the p53 protein adopts the mutant conformation. The next day the culture medium was removed, and the cells then incubated in medium supplemented with either 0.6 M glycerol, or 75 mM trimethylamine N-oxide (TMAO). In the case of the deuterated water, powdered DMEM was reconstituted with 100% $D_2O$, supplemented with serum, and added to the cells. After 2 days of incubation at 39.5° C., the cells were analyzed for their distribution of p53. The results are illustrated in FIG. 12. A1–5 cells were grown on glass coverslips and incubated for 1 D at 39.5° C. Some of the coverslips then were transferred into medium supplemented with either $D_2O$ (100%), TMAO (75 mM), or glycerol (0.6M) and the cells further incubated at 39.5° C. After 2 D of incubation at 39.5° C., the cells were analyzed for the intracellular distribution of p53 by indirect immunofluorescence as described in FIG. 11. Shown only are the immunofluorescent micrographs. Panel A, control cells incubated in normal medium. Panel B, cells incubated in medium prepared with 100% $D_2O$. Panel C, cells incubated in the presence of 75 mM TMAO. Panel D, cells treated with 0.6 M glycerol.

Figure 12A:
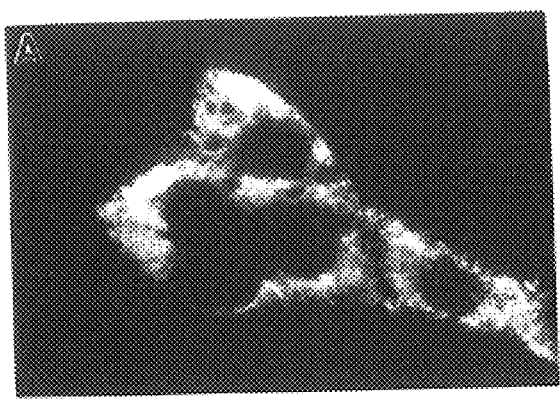
FIG. 12. A1–5 cells incubated at the non-permissive temperature in the presence of protein stabilizing agents exhibit nuclear p53 staining.
Figure 12B:
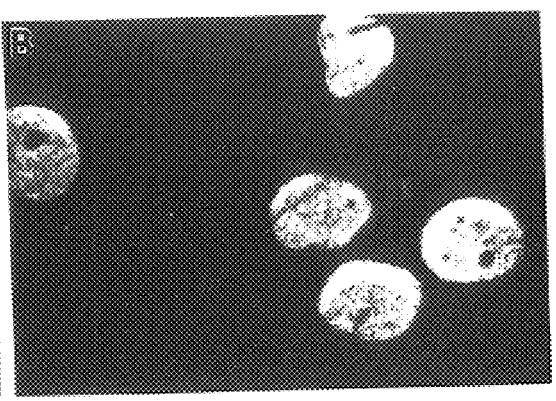
Figure 12C:
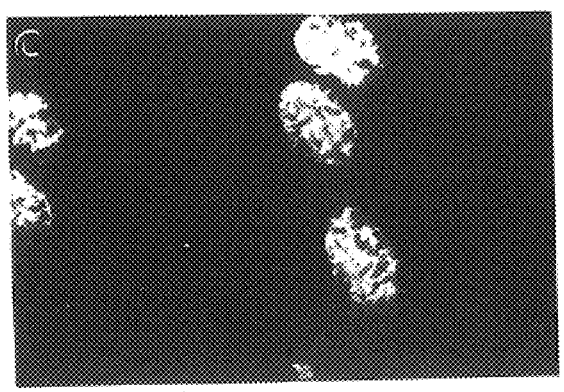
Figure 12D:
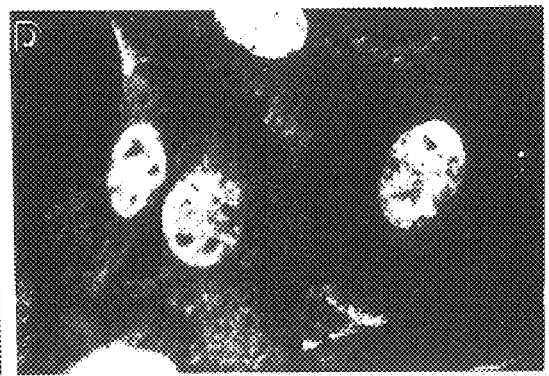

In the control cells maintained at 39.5° C. in normal growth medium, p53 was predominantly cytoplasmic (FIG. 12A). In contrast, cells incubated at 39.5° C. in the presence of $D_2O$ (FIG. 12B), TMAO (FIG. 12C), or glycerol (FIG. 12D) now exhibited a nuclear locale of p53. Thus, incubation of the cells in the presence of the different protein stabilizing agents appeared to result in the mutant p53 protein adopting a wild type conformation at 39.5° C.

Figure 13A:
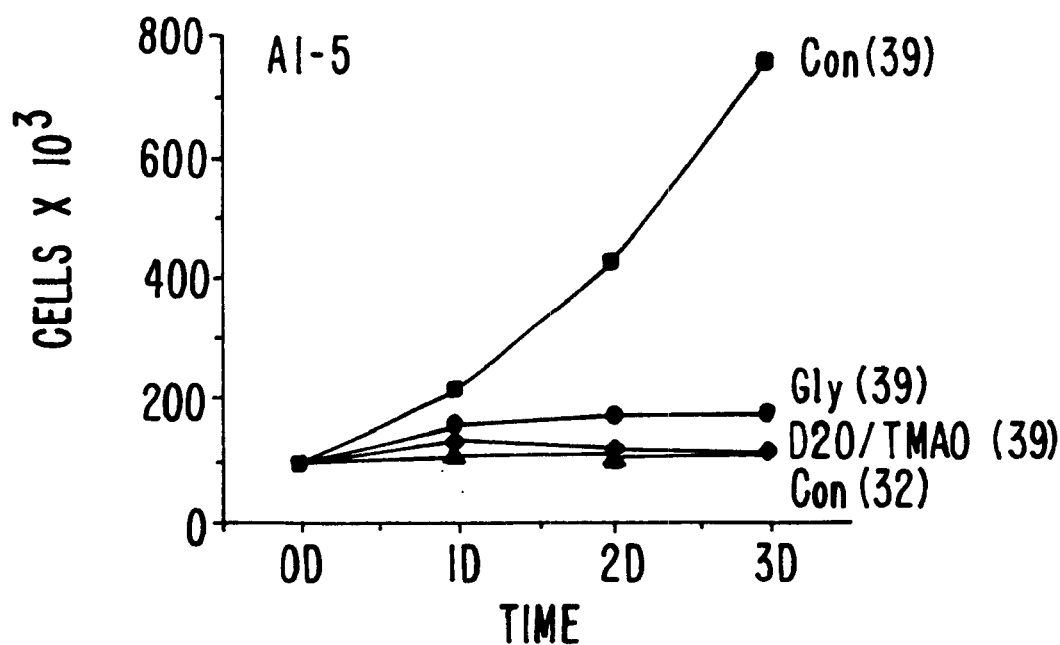
FIG. 13. A1–5 cells treated with protein stabilizers at the nonpermissive temperature exhibit a wild type phenotype as determined by cell proliferation rates.

As an alternative method to screen for the potential beneficial effects of these compounds on p53 function, the proliferative capacity of the A1–5 cells incubated at the nonpermissive temperature, in either the absence or presence of the different chemicals, was determined. As has been shown previously Martinez, J., et al., 1991, Genes Dev. 5:151–159, the A1–5 cells become growth arrested when maintained at the permissive temperature (32.5° C.), ostensibly due to the high levels of the wild type p53 tumor suppressor protein (FIG. 13A). In contrast, at 39.5° C. where the overexpressed p53 protein folds incorrectly and therefore is biologically inactive, the cells continue to proliferate normally. Hence, if treatment with the various protein stabilizing agents corrects the folding of the mutant p53 protein, the cells now should exhibit cell cycle arrest, even when incubated at the nonpermissive temperature. Indeed, treatment of the A1–5 cells maintained at 39.5° C. with any one of the 3 different compounds now resulted in a growth arrested phenotype, similar to that observed for the cells incubated at the permissive temperature where the p53 protein is functional (FIG. 13A).

In FIG. 13A, equal numbers of A1–5 cells, growing at 37° C., were plated on 60 mm dishes in DMEM containing 10% serum. After plating, the cells were moved to 39.5° C. The next day (day 0) the media was removed, and fresh medium supplemented with serum and containing either: nothing (con); 0.6 M glycerol (Gly); 100% $D_2O$ ($D_2O$); or 75 mM TMAO (TMAO), was added to the cells. The cells were further incubated at 39.5° C. for 1, 2 or 3 D. After each day, a plate of the cells was removed and cell number determined as described in the experimental methods. As a control [con (32)], one group of the cells were incubated at 32.5° C., the permissive temperature. In Panel B, equal numbers of cells were plated on 60 mm dishes and treated with the various chemicals as described above. Following 2 D of treatment, the culture medium was removed and the cells extensively washed with and further incubated at 39.5° C. in fresh DMEM containing only 10% FBS. Cell numbers then were determined on day 1 and 2 after the changeover back into normal growth medium.

The effects of the different protein stabilizing agents on the phenotype of the A1–5 cells were reversible (FIG. 14). A1–5 cells growing on coverslips at 39.5° C. were incubated in media supplemented with either; $D_2O$ (panels A–C); TMAO (panels D–F); or glycerol (panels G–I) {concentrations as described in FIG. 3}. After 2 D of incubation at 39.5° C. one coverslip from each group of cells was taken and processed for p53 indirect immunofluorescence. To the remaining coverslips, the media was removed, and the cells washed with and further incubated in fresh medium supplemented only with 10% serum. Following a further 1 D, or 2 D incubation at 39.5° C., the cells were examined for the distribution of p53. Panels A–C; cells after 0, 1 and 2 days respectively following removal of $D_2O$: Panels D–F; cells after 0, 1, and 2 days respectively following removal of TMAO containing media; Panels G–I; cells after 0, 1, and 2 days respectively following removal of glycerol.

Figure 13B:
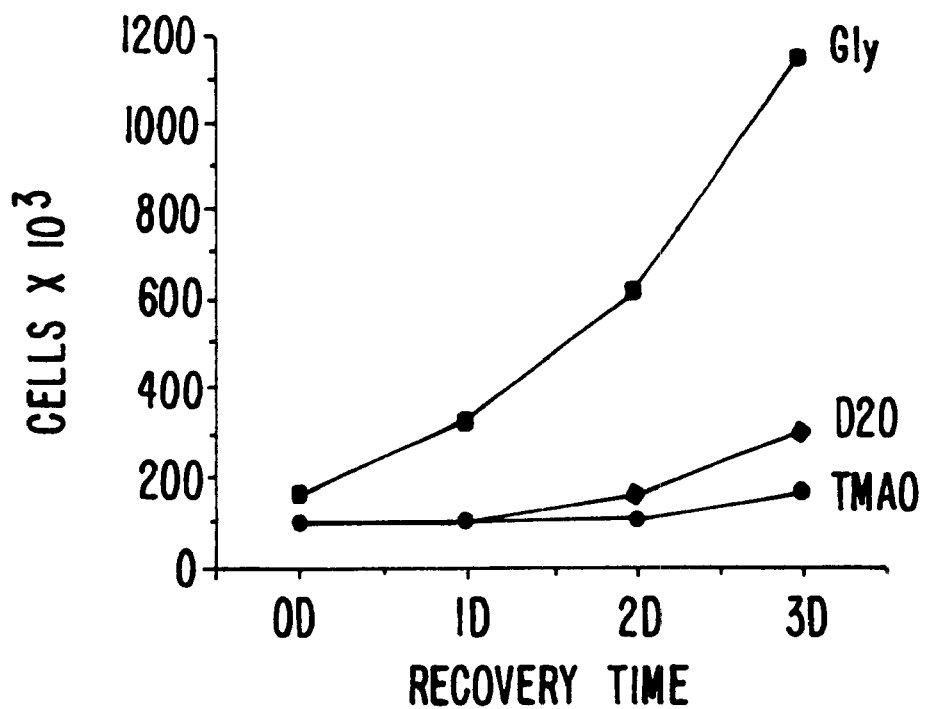
Figure 14A:
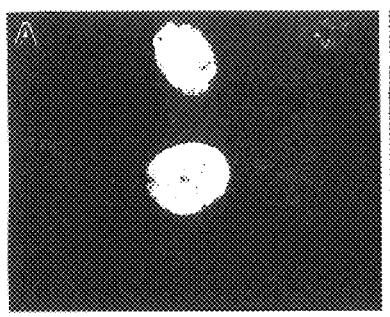
FIG. 14. The effects of the protein stabilizing agents on p53 protein folding are reversible.
Figure 14B:
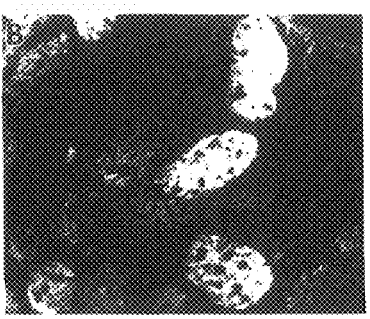
Figure 14C:
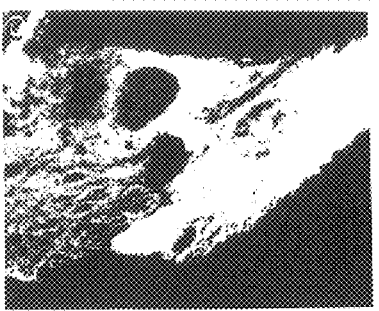
Figure 14D:
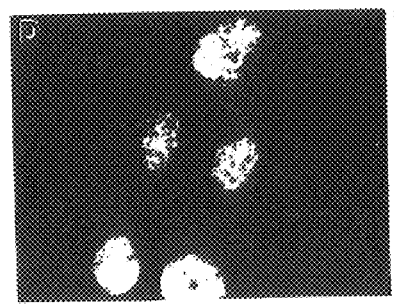
Figure 14E:
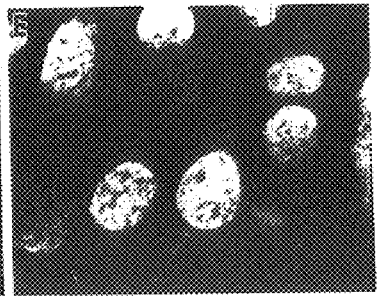
Figure 14F:
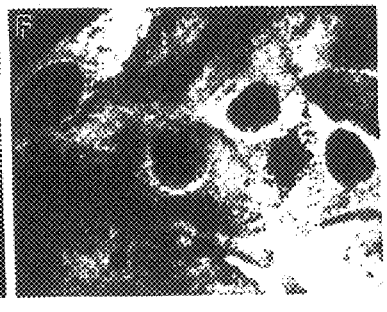
Figures 14G, 14H, 14I:

As was shown earlier, cells incubated in the presence of the different protein stabilizing agents for 2 D at 39.5° C. exhibited a nuclear locale of p53, indicative of the protein being in its wild type conformation. However, when the culture medium containing the protein stabilizing agents was removed and replaced with fresh culture medium, p53 again began to accumulate within the cytoplasm. For example, after only one day following the removal of glycerol, the cells maintained at 39.5° C. no longer displayed a nuclear p53 distribution. In the case of either $D_2O$ or TMAO, after 2 days following their removal all of p53 now was found within the cytoplasm. Similar results were obtained when the analysis was performed by cell counts. As was shown in FIG. 13A, cells incubated at 39.5° C. in the present of the 3 different protein stabilizing agents for 2 days exhibited a growth arrested phenotype, consistent with a functional p53 protein. However, upon removal of the compounds and further incubation of the cells at 39.5° C. in normal culture medium, the cells exhibited a slow resumption in their normal growth rates (FIG. 13B), indicative that p53 now was in the mutant conformation.

Example 4

Correction of pp60$^{src}$ Mutants with Chemical Chaperones

Cells expressing a ts pp60$^{src}$ protein (kindly provided by D. T. Aftab) were routinely maintained under the same conditions.

Rat fibroblasts transfected with a temperature sensitive form of pp60$^{src}$, the transforming protein encoded by Rous sarcoma virus, exhibit a transformed phenotype when incubated at the permissive temperature of 32.5° C. (21). FIG. 15 shows that cells expressing a ts form of pp60$^{src}$ were incubated at 32.5° C., or at 39.5° C. in the presence or absence of 1M glycerol. Following three days of treatment, the cells were examined by phase-contrast microscopy. Panel A, cells incubated at 32.5° C. for 3 days. Panel B, cells incubated at 39.5° C. for 3 days. Panel C, cells incubated at 39.5° C. for 3 days in the presence of 1M glycerol.

Figure 15A:
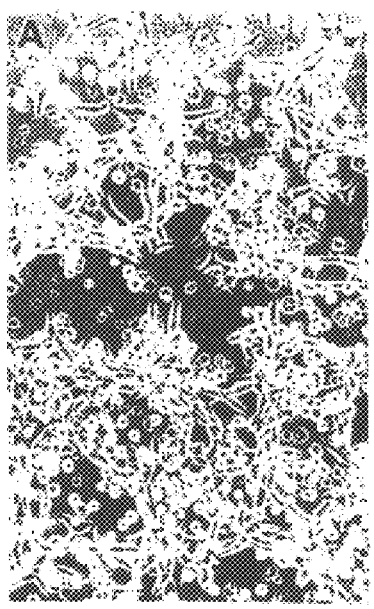
FIG. 15. The presence of glycerol corrects temperature sensitive (ts) pp60$^{src}$ activities at the nonpermissive temperature.
Figure 15B:
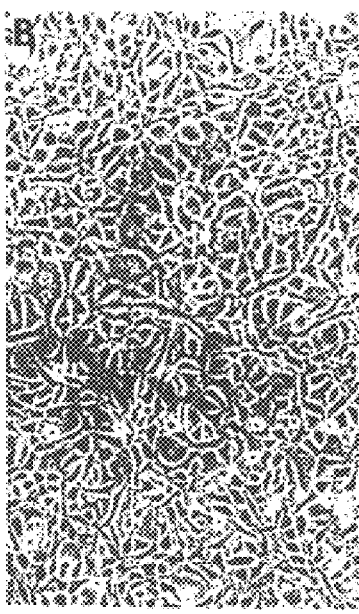
Figure 15C:
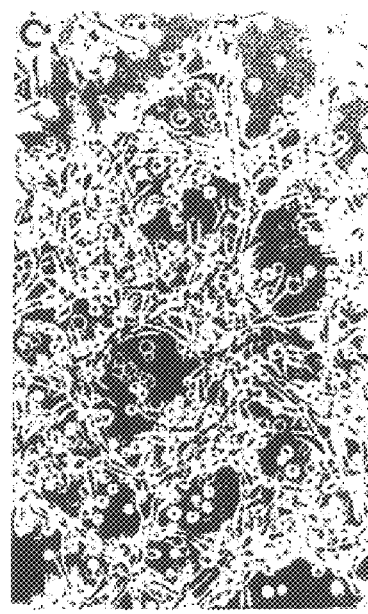

As shown in FIG. 15A, when incubated at 32.5° C. where pp60$^{src}$ is biologically active, the cells adhere weakly to the substratum. Instead, at this permissive temperature the cells grow on top of one another to form large foci. At 39.5° C.

where pp60$^{src}$ is biologically inactive, the cells display a well spread morphology and exhibit contact-dependent growth arrest (FIG. 15B). Inclusion of glycerol into the culture medium was sufficient to restore the transformed phenotype of the cells when incubated at the non-permissive temperature. For example, cells incubated at 39.5° C. in the presence of 1M glycerol for 3 days (FIG. 15C) now exhibited a morphology very similar to the control cells maintained at 32.5° C. where pp60$^{src}$ is active (FIG. 15A). Interestingly the 2 other compounds, TMAO and deuterated water, were much less effective in restoring wild type pp60$^{src}$ activity at the nonpermissive temperature (data not shown).

Example 5

Correction of ts20 Mutants with Chemical Chaperones ts20 cells (kindly provided by H. Ozer) were maintained at 32.5° C. (the permissive temperature) in DMEM medium containing 10% fetal bovine serum. They were plated at subconfluency and then incubated at 32.5° C., or 39.5° C. in either the absence or presence of glycerol, TMAO or D$_2$O. Two days later the cells were examined by phase-contrast microscopy (FIG. 16). In FIG. 16, equal numbers of cells expressing a temperature sensitive mutant of the E1 enzyme were incubated at 32.5° C. (permissive temp.), or at 39.5° C. (nonpermissive temp.) in either the presence or absence of the different protein stabilizing agents. After two days of incubation the cells were examined by phase-contrast microscopy. Panel A, cells incubated at 32.5° C. Panel B, cells incubated at 39.5° C. Panel C, cells incubated at 39.5° C. in medium prepared with 100% D2O. Panel D, cells incubated at 39.5° C. in the presence of 75 mM TMAO. Panel E, cells incubated at 39.5° C. in the presence of 0.75 M glycerol.

The untreated control cells maintained at 32.5° C. (where the E1 enzyme is active) had grown to near confluence and exhibited a well spread morphology (FIG. 16A). In contrast, when incubated at the nonpermissive temperature (i.e. 39.5° C. where E1 is inactive) the cells did not grow at all (FIG. 16B). Note the few cells that did survive at 39.5° C. exhibited a spindle-shaped morphology, markedly different than that observed for the cells grown at the permissive temperature. Interestingly, different morphological phenotypes and apparent growth rates were observed when the cells were incubated in the presence of the different protein stabilizing agents. For example, cells incubated at 39.5° C. in culture medium prepared with 100% D$_2$O exhibited an apparent growth rate only slightly higher than that observed for the untreated cells maintained at the nonpermissive temperature. In addition, the morphology of the cells appeared to reflect an "intermediate phenotype," with both spindle-shaped and well rounded cells being observed (FIG. 16C). Treatment of the ts20 cells with either TMAO (FIG. 16D) or glycerol (FIG. 16E) resulted in an apparent restoration of the wild type phenotype. Like the control cells maintained at 32.5° C., those cells incubated at 39.5° C. in the presence of TMAO or glycerol exhibited normal growth rates and a well-rounded morphology.

Figure 17:
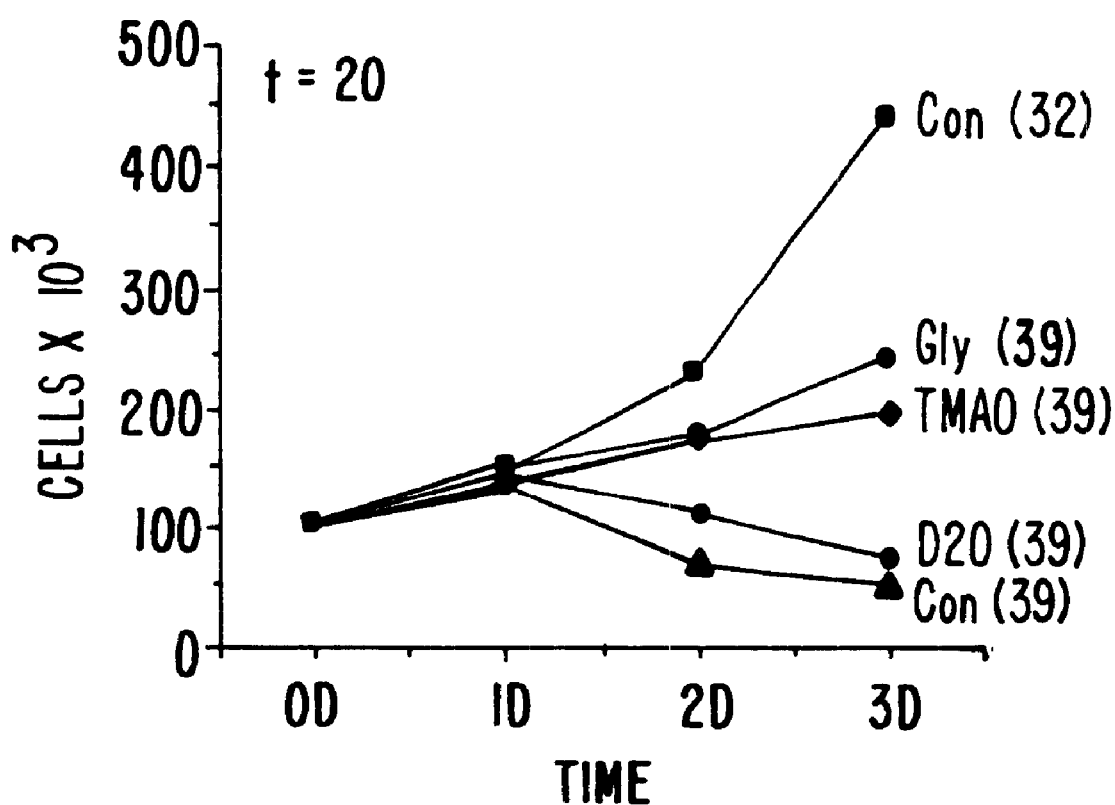
FIG. 17. ts20 cells incubated in the presence of the protein stabilizers proliferate at the nonpermissive temperature.

A more quantitative comparison of the growth rates of the cells incubated at 39.5° C. in the presence of the 3 protein stabilizing compounds is shown in FIG. 17. In FIG. 17, ts20 cells were plated on 60 mm dishes at low confluence and incubated for 24 hr at 32.5° C. Control cells (no added chemicals), were then placed at either 32.5° C. (permissive temp.) or 39.5° C. (nonpermissive temp.). In parallel, some of the cells were incubated in the presence of the 3 different compounds and then incubated at 39.5° C. After 1, 2, or 3 days of incubation, the cells were collected and cell number determined as described in the methods. Cell number as a function of the days (D) of incubation at either 32.5 or 39.5 are presented.

Cells incubated at 32.5° C. in regular culture medium displayed an exponential rate of growth, while those maintained at 39.5° C. failed to grow. The actual reduction in cell number found for the cells maintained at 39.5° C. was observed over the course of many experiments, and likely represents cell death (although the mechanism, necrosis versus apoptosis, remains unclear). Similar to our observations using phase-contrast microscopy, cells incubated at 39.5° C. in culture medium prepared with D$_2$O failed to exhibit any significant growth. Cells incubated with either glycerol or TMAO at 39.5° C. did exhibit a recovery of cell proliferation, albeit at rates less than that observed for the control cells incubated at 32.5° C.

Growth inhibition of the ts20 cells at the non-permissive temperature has been suggested to be due, at least in part, to the failure of the cells to ubiquitinate and therefore degrade the normally short-lived p53 tumor suppressor protein. Chowdary, D. R., et al., 1994, Mol. Cell. Biol. 14:1997–2003. To test this, ts20 cells were plated on coverslips and incubated at 32.5° C. (the permissive temperature). The next day some of the coverslips were maintained at 32.5° C., while the other coverslips were placed into media either lacking or containing glycerol or TMAO, and then incubated at 39.5° C. One day later the coverslips were fixed and the intracellular locale of p53 determined by indirect immunofluorescence analysis using the monoclonal antibody PAb 421. Shown in panels A, C, E, and G are phase-contrast micrographs, and in panels B, D, F, and H fluorescent micrographs. Panels A&B, cells grown at 32.5° C. Panels C & D, cells incubated at 39.5° C. Panels E&F, cells incubated at 39.5° C. in the presence of 75 mM TMAO. Panels G & H, cells incubated in the presence of 0.75 M glycerol.

Figure 18A:
FIG. 18. Protein stabilizing chemicals correct the temperature sensitive phenotype of ts20 cells, as demonstrated by a lack of nuclear p53 staining at the nonpermissive temperature.
Figure 18B:
Figure 18C:
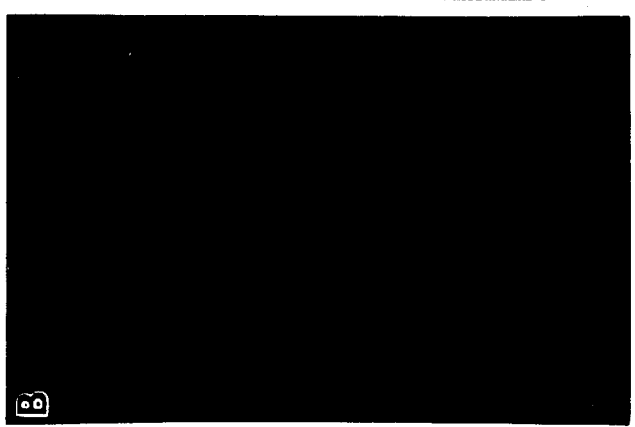
Figure 18D:
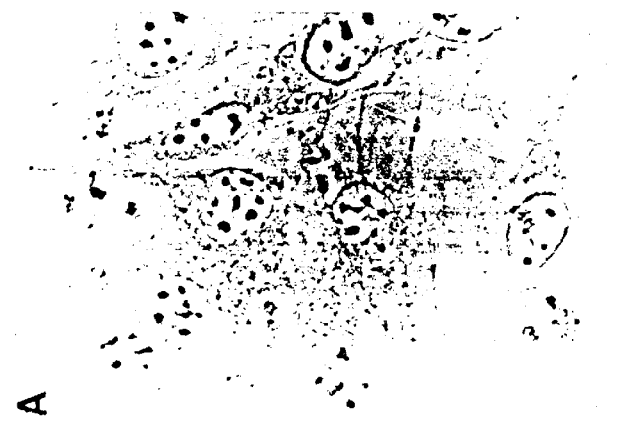

When the cells were maintained at the permissive temperature (at 32.5° C. where E1 is functional), p53 levels were undetectable as determined by indirect immunofluorescence analysis (FIG. 18B). In contrast, p53 easily was observed within the nucleus of those cells maintained at the non-permissive temperature of 39.5° C. (FIG. 18D). When the cells were incubated at 39.5° C. in the presence of either TMAO (FIG. 18F) or glycerol however (FIG. 18H), the levels of p53 nuclear staining was significantly reduced, approaching that observed for the cells maintained at the permissive temperature (FIG. 18B).

Figure 19A:
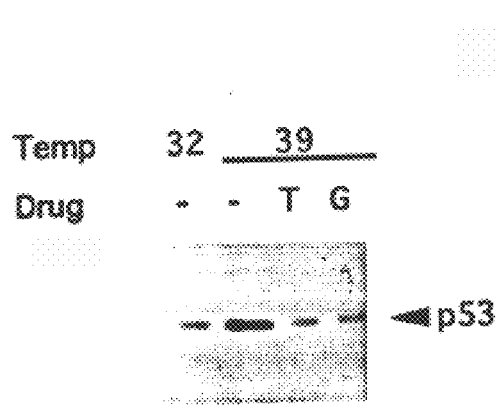
FIG. 19. ts20 cells incubated at 39.5° C. in the presence of protein stabilizing agents now exhibit low levels of the p53 protein as determined by Western blotting.

Similar results were obtained when the levels of p53 in the ts20 cells were determined by Western blotting (FIG. 19). In FIG. 19, ts20 cells were plated on 35 mm dishes and incubated at 32.5° C. for 1 day. One plate of cells was maintained at 32.5° C., while the other plates were incubated at 39.5° C. in the absence or presence of either TMAO (T) or glycerol (G). One day later the cells were harvested and the relative levels of p53 (Panel A) or the cytosolic chaperones hsp73/72 (Panel B) determined by Western blotting.

Figure 19B:
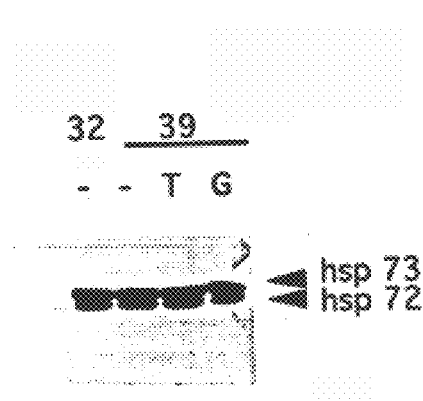

Cells incubated at 32.5° C. showed relatively low levels of p53 while those incubated at 39.5° C. had much higher levels of the protein. When the cells were incubated at 39.5° C. in the presence of either TMAO (T) or glycerol (G) (FIG. 19A), the levels of p53 were significantly reduced, now appearing similar to that observed for the cells maintained at 32.5° C. Again these observations are consistent with the idea that the different protein stabilizing agents are effective in restoring a functional ubiquitin pathway (thereby resulting in normal p53 degradation) even when the cells are maintained at the nonpermissive temperature. It should be noted that the chemical treatments did not have any obvious effects on general cellular metabolism, with the overall rates of protein synthesis, for example, being similar for each treatment (data not shown). Along these lines, we were also curious to know whether incubation of the ts20 cells with any of the different protein stabilizing agents might have an effect on the overall levels of the cytosolic hsp70 chaperones. As is shown in FIG. 19B the relative levels of hsp73 and hsp72 appeared identical in the cells regardless of the incubation temperature, or the inclusion of either glycerol or TMAO into the culture medium.

We next examined whether the mutant phenotype was reversible in cells expressing the ts E1 protein. For these experiments, we again used the appearance of p53 staining (or lack thereof) as an assay for E1 enzyme activity. ts20 cells were plated on coverslips and incubated for 1 day at 32.5° C. All of the coverslips then were placed at 39.5° C. for 1 day to induce the mutant phenotype. The next day, fresh media containing either 0.75M glycerol or 75 mM TMAO was added and the cells further incubated at 39.5° C. As a control, one of the coverslips was placed back at 32.5° C. following the 1 D incubation at 39.5° C. (no added chemicals). One day later all of the coverslips were collected and the distribution of p53 determined by indirect immunofluorescence as described earlier. Shown are the fluorescent micrographs. Panel A, cells maintained at 39.5° C. for 2 D. Panel B, cells incubated at 39.5° C. for one day, and then placed at 32.5° C. for one day. Panel C, cells incubated at 39.5° C. for one day, TMAO then added (to a final concentration of 75 mM) and the cells incubated further at 39.5° C. for one day. Panel D, cells incubated at 39.5° C. for one day, glycerol then added (to a final concentration of 0.75 M) and the cells incubated further at 39.5° C. for one day.

Figure 20A:
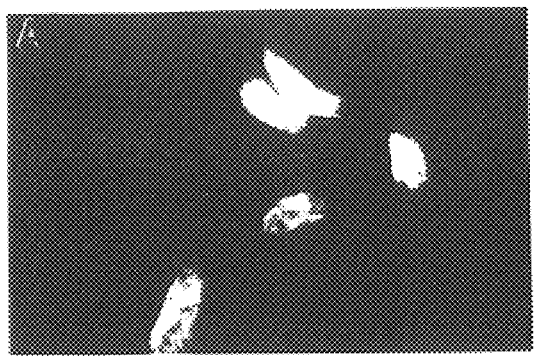
FIG. 20. Addition of protein stabilizing agents to cells already at the nonpermissive temperature is effective in restoring wild type E1 activities.
Figure 20B:
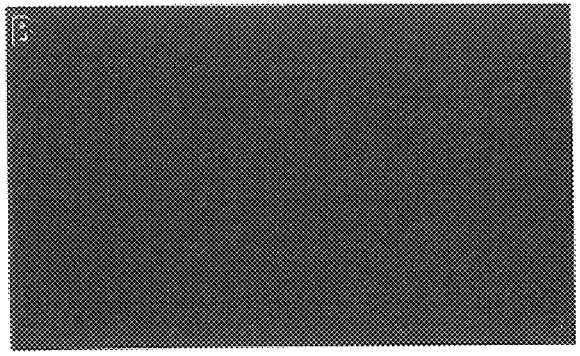
Figure 20C:
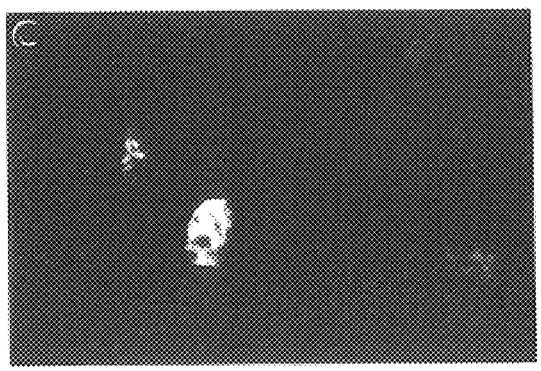
Figure 20D:
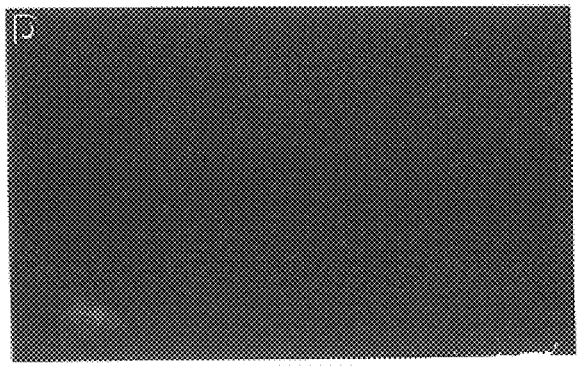
Figure 21A:
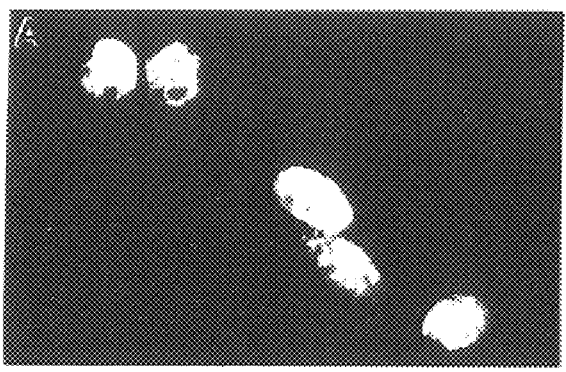
FIG. 21. Protein stabilizers correct the folding defect of the newly synthesized but not the mature form of the E1 enzyme.
Figure 21B:
Figure 21C:
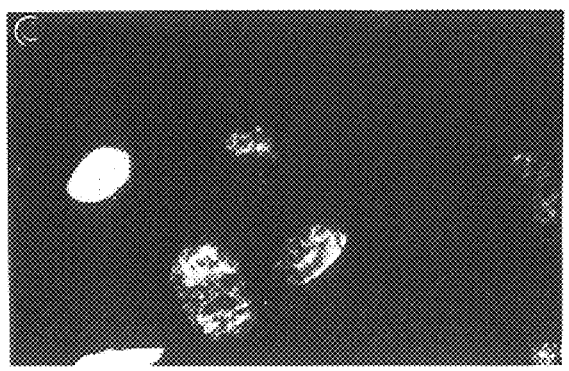
Figure 21D:
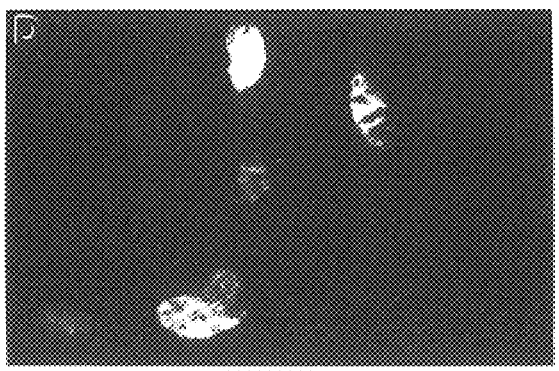

As shown in FIG. 20A, cells maintained at 39.5° C. for 2 days in the absence of protein stabilizers exhibited strong nuclear p53 staining, indicative that the E1 enzyme (and therefore the ubiquitin pathway) was inactive. Switching the 2-day/39.5° C. cells back to 32.5° C. for 1 day resulted in a disappearance of nuclear p53 staining (FIG. 20B), indicative of a restoration of the ubiquitin-dependent protein degradation pathway. In those cells incubated at 39.5° C. for 1 day in normal culture medium, and then transferred into culture medium containing either TMAO or glycerol for an additional day at 39.5° C., mixed results were obtained. Specifically, TMAO treatment resulted in a diminishment, but not complete abolition of nuclear p53 staining (FIG. 20C). In the case of glycerol treatment however, p53 staining no longer was observed (FIG. 20D).

Example 5A
Proper Folding of the Newly Synthesized, but not the Mature, Form of the E1 Protein is Corrected by the Chemical Treatments A set of experiments were performed to determine which population of the E1 enzyme was being corrected via treatment of the cells with the different chemicals. Specifically, were the chemical treatments correcting or "rescuing" the misfolding of the mature (already synthesized) E1 protein, or were they only efficacious as it pertained to the folding of the newly synthesized E1 protein? To address this question, the experiments presented in FIG. 20 were repeated. This time however, the protein synthesis inhibitor cycloheximide was added prior to shifting the cells (on day 2) into medium containing the different chemicals. In FIG. 21, ts20 cells were plated on coverslips and incubated at 39.5° C. for one day to induce the mutant phenotype. The cells then were incubated for an additional 24 h at 39.5° C. with fresh media containing either 0.75 M glycerol or 75 mM TMAO and supplemented with the protein synthesis inhibitor cycloheximide. As a positive control, one of the coverslips incubated at 39.5° C. for one day was returned to 32.5° C. and incubated for an additional 24 h in the presence of cycloheximide. Afterwards the cells were fixed and analyzed for the levels of p53 by indirect immunofluorescence. Panel A, cells incubated for 1 D at 39.5° C., and then for an additional day at 39.5° C. in the presence of cycloheximide. Panel B, cells incubated for 1 D at 39.5° C., and then for an additional day at 32.5° C. in the presence of cycloheximide. Panel C, cells incubated for 1 D at 39.5° C., and then for an additional day at 39.5° C. in the presence of cycloheximide and TMAO. Panel D, cells incubated for 1 D at 39.5° C., and then for an additional day at 39.5° C. in the presence of cycloheximide and glycerol.

Using this approach, the mature E1 enzyme could potentially be corrected in the presence of the protein stabilizing agents, especially considering the relatively long half life (~20 h) of this protein. Stephen, A. G., et al., 1996, *J. Biol. Chem.* 271:15608–15614. Instead, we observed that the addition of the protein synthesis inhibitor blocked the reversion of the cells back to the wild type phenotype. For example in each case, be it in the control cells returned to 32.5° C. (FIG. 21B), or the cells left at 39.5° C. in the presence of either TMAO (FIG. 21C) or glycerol (FIG. 21D) strong nuclear staining of p53 was still observed. This is in marked contrast to the results shown in FIG. 20 where the nuclear staining of p53 no longer was observed upon temperature shift-down, or the addition of the different chemicals to the cells maintained at 39.5° C. Therefore, we conclude that in the case of the E1 enzyme, the different protein stabilizing agents apparently do not correct the already misfolded, mature protein. Instead, we suspect that the chemical chaperones are only effective in influencing the folding pathway of the newly synthesized E1 protein. Presumably, when synthesized at 39.5° C. in the presence of the chemicals, at least a portion of the newly synthesized E1 enzyme now adopts its properly folded and biologically active conformation.

It should be noted that two types of temperature sensitive proteins folding defects have been described in the literature: Class 1, correctly folded (mature) proteins which are destabilized upon a temperature shift, thereby resulting in their loss of activity (Hawkes, R., et al., 1984, *J. Mol. Biol.* 175:195–212) or Class 2, newly synthesized proteins which are able to fold properly at the permissive temperature, but which fold incorrectly at the nonpermissive temperature (Sturtevant, J. M., et al., 1989, *J. Biol. Chem.* 264:10693–10698). The above results indicate that it is mainly this latter class of temperature sensitive mutants which are affected in the experiments presented here. For example, for each of the ts mutants examined above, the time needed to correct the mutant phenotype via exposure of the cells to the protein stabilizing agents was relatively long. Furthermore, at least for E1 enzyme, in the absence of ongoing protein synthesis, inclusion of the different chemicals into the culture medium did not result in the apparent restoration of mature E1 enzyme function (albeit as determined indirectly by monitoring p53 levels). This observation, along with a number of other unpublished findings, are consistent with the idea that mostly newly synthesized temperature sensitive protein folding mutants which are amenable to correction via the chemical chaperones. However, proteins do exist which manifest destabilizing temperature sensitive mutations (e.g., Class 1 mutants described above) and some of these may be amenable to correction via the strategies used here (currently under study).

In the case of the Class 2 mutants it seems that the chemical chaperones affect a critical step in the folding pathway of the newly synthesized, temperature sensitive protein folding mutant. For example, at the nonpermissive temperature, the chemical chaperones may help in lowering a critical "energy barrier" which is rate limiting in the folding pathway. Alternatively (or in addition), the chemical chaperones might act to reduce the propensity of the newly synthesized mutant protein to go "off pathway" and end up in a denatured or aggregated state.

Whatever the mechanism, the data herein indicate that once the particular temperature sensitive protein folding mutant successfully has acquired its properly folded and biologically active state, it remains correctly folded at the nonpermissive temperature, even when the chemical chaperon is subsequently removed.

The preceding examples are merely illustrative and are not intended to limit the invention in any way. All references cited herein are incorporated by reference in their entirety.

What is claimed is:

1. A method of improving a phenotypic defect in a mammalian cell that contains a conformationally defective target protein wherein the conformational defect causes the phenotypic defect, comprising contacting a first cell that expresses said conformationally defective target protein with an amount of a protein stabilizing agent that is effective to improve the conformational defect, thereby improving the phenotypic defect of the first cell in comparison with a second cell having the same conformationally defective target protein and phenotypic defect, wherein the second cell is not contacted with the protein stabilizing agent, with the proviso that the protein stabilizing agent is not congo red, DMSO or glycerol.

2. The method according to claim 1, wherein the defective target protein is the gene product of a naturally occurring mutant nucleic acid.

3. The method according to claim 1, wherein the defective target protein is the gene product of a heterologous nucleic acid.

4. The method according to claim 1, wherein the defective target protein is selected from the group consisting of the cystic fibrosis transmembrane conductance regulator (CFTR) protein, emphysema and chronic liver disease α-1 anti-trypsin inhibitor, LDL receptor (familial hypercholesterolinemia), β-hexylaminidase (Tay-sachs), fibrillin (Marfan syndrome) superoxide dismutase (amyotropic lateral sclerosis), collagen (scurvy), α-ketoacid dehydrogenase complex (maple syrup urine disease), p53 (cancer), type I procollagen pro-α (osteogenesis imperfecta), β-amyloid (Alzheimer's disease), crystallins (cataracts), rhodopsin (retinitis pigmentosa), and insulin receptor (leprechaunism).

5. The method according to claim 1, wherein the protein stabilizing agent is selected from the group consisting of deuterated water, polyols and sugars, including erytritol, inositol, trehalose isofluoroside, polyethylene glycol, amino acids and derivatives thereof, including glycine, alanine, proline, taurine, betaine, octopine, glutamate, sarcosine, gamma-aminobutyric acid, and trimethylamine N-oxide (TMAO).

6. The method according to claim 1, wherein the phenotypic defect is caused by a condition selected from the group consisting of improper folding, improper co- and post-translational modification, improper subcellular targeting, inability to bind biological ligands, aggregation, proteolytic degradation, temperature sensitive folding, and any combination thereof.

7. The method according to claim 6, wherein the condition that causes the phenotypic defect occurs in a part of the protein that is selected from the group consisting of pre-sequence, pro-sequence, and mature protein sequence.

8. A method of improving a phenotypic defect in a mammalian cell that contains a conformationally defective target protein wherein the conformational defect causes the phenotypic defect, and wherein the conformational defect is a temperature sensitive folding defect, comprising contacting a first cell that expresses said conformationally defective target protein with an amount of a protein stabilizing agent that is effective to improve the conformational defect, thereby improving the phenotypic defect of the first cell in comparison with a second cell having the same conformationally defective target protein and phenotypic defect, wherein the second cell is not contacted with the protein stabilizing agent, with the proviso that the protein stabilizing agent is not congo red, DMSO or glycerol.

9. A method of improving a phenotypic defect in a mammalian cell that contains a conformationally defective target protein wherein the conformational defect causes the phenotypic defect, and wherein the defective target protein is an enzyme, comprising contacting a first cell that expresses said conformationally defective target protein with an amount of a protein stabilizing agent that is effective to improve the conformational defect, thereby improving the phenotypic defect of the first cell in comparison with a second cell having the same conformationally defective target protein and phenotypic defect, wherein the second cell is not contacted with the protein stabilizing agent, with the proviso that the protein stabilizing agent is not congo red, DMSO or glycerol.

10. A method of improving a phenotypic defect in a mammalian cell that contains a conformationally defective target protein wherein the conformational defect causes the phenotypic defect, and wherein the conformational defect causes improper protein targeting, comprising contacting a first cell that expresses said conformationally defective target protein with an amount of a protein stabilizing agent that is effective to improve the conformational defect, thereby improving the phenotypic defect of the first cell in comparison with a second cell having the same conformationally defective target protein and phenotypic defect, wherein the second cell is not contacted with the protein stabilizing agent, with the proviso that the protein stabilizing agent is not congo red, DMSO or glycerol.

11. A method of improving a phenotypic defect in a mammalian cell that contains a conformationally defective target protein wherein the conformational defect causes the phenotypic defect, comprising contacting a first cell that expresses said conformationally defective target protein with an amount of a protein stabilizing agent that is effective to improve the conformational defect, thereby improving the phenotypic defect of the first cell in comparison with a second cell having the same conformationally defective target protein and phenotypic defect, wherein the second cell is not contacted with the protein stabilizing agent, and wherein the protein stabilizing agent is trimethylamine N-oxide.

12. A method of improving a phenotypic defect in a mammalian cell that contains a conformationally defective target protein wherein the conformational defect causes the phenotypic defect, comprising contacting a first cell that expresses said conformationally defective target protein with an amount of a protein stabilizing agent that is effective to improve the conformational defect, thereby improving the phenotypic defect of the first cell in comparison with a second cell having the same conformationally defective target protein and phenotypic defect, wherein the second cell is not contacted with the protein stabilizing agent, and wherein the protein stabilizing agent is an amino acid or derivative thereof, including glycine, alanine, proline, taurine, betaine, octopine, glutamate, sarcosine, gamma-aminobutyric acid, and trimethylamine N-oxide (TMAO).

* * * * *

(12) EX PARTE REEXAMINATION CERTIFICATE (6333rd)
United States Patent
Welch et al.

(10) Number: US 6,541,195 C1
(45) Certificate Issued: *Jul. 29, 2008

(54) CORRECTION OF GENETIC DEFECTS USING CHEMICAL CHAPERONES

(75) Inventors: William J. Welch, San Francisco, CA (US); C. Randell Brown, San Francisco, CA (US); Jörg Tatzelt, München (DE)

(73) Assignee: The Regents of the University of California, Oakland, CA (US)

Reexamination Request:
No. 90/008,745, Jul. 3, 2007

Reexamination Certificate for:
Patent No.: 6,541,195
Issued: Apr. 1, 2003
Appl. No.: 09/823,657
Filed: Mar. 30, 2001

( * ) Notice: This patent is subject to a terminal disclaimer.

Related U.S. Application Data

(63) Continuation of application No. 09/291,406, filed on Apr. 13, 1999, now Pat. No. 6,270,954, which is a continuation-in-part of application No. 08/838,691, filed on Apr. 9, 1997, now Pat. No. 5,900,360.

(60) Provisional application No. 60/015,155, filed on Apr. 10, 1996.

(51) Int. Cl.
*A61K 31/77* (2006.01)
*A61K 31/74* (2006.01)
*A61K 31/095* (2006.01)
*A61K 31/045* (2006.01)
*A61K 31/198* (2006.01)
*A61K 31/047* (2006.01)
*A61K 31/10* (2006.01)
*A61K 31/185* (2006.01)
*A61K 31/197* (2006.01)
*A61K 31/131* (2006.01)
*A61K 31/205* (2006.01)
*A61K 31/401* (2006.01)
C12Q 1/00 (2006.01)
C12Q 1/32 (2006.01)
C12Q 1/37 (2006.01)
G01N 33/50 (2006.01)

(52) U.S. Cl. .............................. 435/4; 435/23; 435/24; 435/26; 435/963

(58) Field of Classification Search ....................... None
See application file for complete search history.

(56) References Cited

U.S. PATENT DOCUMENTS

| | | | |
|---|---|---|---|
| 5,900,360 | A | 5/1999 | Welch et al. |
| 6,270,954 | B1 | 8/2001 | Welch et al. |
| 6,541,195 | B2 | 4/2003 | Welch et al. |

OTHER PUBLICATIONS

U.S. Appl. No. 60/015,155, filed Apr. 10, 1996, Welch et al.

Brown et al., 1996, Chemical chaperones correct the mutant phenotype of the ΔF508 cystic fibrosis transmembrane conductance regulator protein, Cell Stress Chaperones 1(2):117–125.

Brown et al., 1997, Correcting temperature–sensitive protein folding defects, J, Clin. Invest., 99:1432–1444.

Kulka et al., 1988, A chinese hamster cell cycle mutant arrested at G2 phase has a temperature–sensitive ubiquitin–activating enzyme, E1, J. Biol. Chem., 263:15726–15731.

*Primary Examiner*—Bennett Celsa

(57) ABSTRACT

A method of improving a phenotypic defect in a cell that contains a conformationally defective target protein wherein the conformational defect causes the phenotype defect, comprising contacting a first cell that expresses said conformationally defective target protein with an amount of a protein stabilizing agent that is effective to improve the conformational defect, thereby improving the phenotypic defect of the first cell in comparison with a second cell having the same conformationally defective target protein and phenotypic defect, wherein the second cell is not contacted with the protein stabilizing agent.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–9 and 10 are cancelled.

Claims 11 and 12 were not reexamined.

* * * * *